United States Patent
Cui et al.

(10) Patent No.: US 10,323,166 B2
(45) Date of Patent: Jun. 18, 2019

(54) RESIN ADDITIVE COMPOSITION AND ANTISTATIC THERMOPLASTIC RESIN COMPOSITION

(71) Applicant: ADEKA CORPORATION, Tokyo (JP)

(72) Inventors: Chun Cui, Saitama (JP); Tatsuhito Nakamura, Saitama (JP); Kazukiyo Nomura, Saitama (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 15/563,289

(22) PCT Filed: Mar. 8, 2016

(86) PCT No.: PCT/JP2016/057247
§ 371 (c)(1),
(2) Date: Sep. 29, 2017

(87) PCT Pub. No.: WO2016/158258
PCT Pub. Date: Oct. 6, 2016

(65) Prior Publication Data
US 2018/0072931 A1    Mar. 15, 2018

(30) Foreign Application Priority Data

Mar. 31, 2015 (JP) ................. 2015-071351
Dec. 8, 2015  (JP) ................. 2015-239438

(51) Int. Cl.
| | |
|---|---|
| *C09K 3/16* | (2006.01) |
| *C08K 5/521* | (2006.01) |
| *C08L 23/00* | (2006.01) |
| *C08L 67/02* | (2006.01) |
| *C07F 5/06* | (2006.01) |
| *C08K 5/527* | (2006.01) |
| *C08K 5/56* | (2006.01) |
| *C08L 23/02* | (2006.01) |
| *C08K 5/098* | (2006.01) |
| *C08K 5/00* | (2006.01) |

(52) U.S. Cl.
CPC ............... *C09K 3/16* (2013.01); *C07F 5/069* (2013.01); *C08K 5/521* (2013.01); *C08K 5/527* (2013.01); *C08K 5/56* (2013.01); *C08L 23/00* (2013.01); *C08L 23/02* (2013.01); *C08L 67/02* (2013.01); *C08K 5/0075* (2013.01); *C08K 5/098* (2013.01)

(58) Field of Classification Search
USPC ..................................................... 524/108
See application file for complete search history.

(56) References Cited

U.S. PATENT DOCUMENTS

| | | |
|---|---|---|
| 2015/0353796 A1 | 12/2015 | Nakamura et al. |
| 2016/0289375 A1 | 10/2016 | Nakamura et al. |
| 2017/0210959 A1 | 7/2017 | Nakamura et al. |

FOREIGN PATENT DOCUMENTS

| | | |
|---|---|---|
| EP | 3 173 454 A1 | 5/2017 |
| GB | 2 112 789 A | 7/1983 |

(Continued)

OTHER PUBLICATIONS

European Search Report for Application No. 16772142.2, dated Jan. 15, 2019.

(Continued)

*Primary Examiner* — Terressa Boykin
(74) *Attorney, Agent, or Firm* — Birch, Stewart, Kolasch & Birch, LLP

(57) ABSTRACT

Provided are: a resin additive composition capable of imparting excellent antistatic effect in a small amount, and an antistatic thermoplastic resin composition. The resin additive composition contains two or more selected from aromatic metal phosphates (H) represented by the following Formula (3) or (4) in an amount of 0.001 to 50 parts by mass with respect to 100 parts by mass of a polymer compound (E). The polymer compound (E) has a structure in which a diol, an aliphatic dicarboxylic acid, an aromatic dicarboxylic acid, a compound (B) which contains at least one group represented by the following Formula (1) and has hydroxyl groups at both ends, and an epoxy compound (D) having two or more epoxy groups are bound via ester bonds:

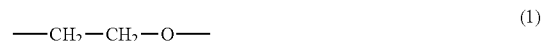

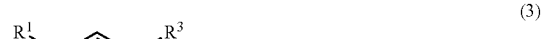

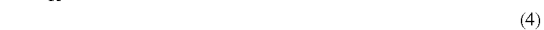

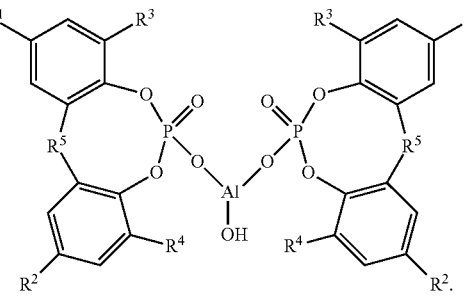

20 Claims, No Drawings

(56) References Cited

FOREIGN PATENT DOCUMENTS

| | | |
|---|---|---|
| JP | 58-118838 A | 7/1983 |
| JP | 59-184252 A | 10/1984 |
| JP | 2-073837 A | 3/1990 |
| JP | 3-290464 A | 12/1991 |
| JP | 6-067357 A | 3/1994 |
| JP | 8-183889 A | 7/1996 |
| JP | 2001-278985 A | 10/2001 |
| JP | 2005-187733 A | 7/2005 |
| JP | 2008-208236 A | 9/2008 |
| JP | 2009-256474 A | 11/2009 |
| JP | WO 2014/148454 A1 | 9/2014 |
| JP | 2014-227470 A | 12/2014 |
| WO | WO 2014/115745 A1 | 7/2014 |
| WO | WO 2016/013323 A1 | 1/2016 |

OTHER PUBLICATIONS

International Search Report (PCT/ISA/210) issued in PCT/JP2016/057247, dated Apr. 19, 2016.
Written Opinion (PCT/ISA/237) issued in PCT/JP2016/057247, dated Apr. 19, 2016.

RESIN ADDITIVE COMPOSITION AND ANTISTATIC THERMOPLASTIC RESIN
COMPOSITION

TECHNICAL FIELD

The present invention relates to a resin additive composition and an antistatic thermoplastic resin composition (hereinafter, also simply referred to as "additive composition" and "resin composition", respectively). More particularly, the present invention relates to: a resin additive composition which is capable of imparting excellent antistaticity to thermoplastic resins while inhibiting deterioration of their physical properties caused by an addition of an antistatic agent; and an antistatic thermoplastic resin composition which has a short molding cycle at the time of molding and can provide a molded article having excellent transparency, strength and long-lasting antistaticity.

BACKGROUND ART

Thermoplastic resins, particularly polyolefin resins, are advantageous for having not only excellent moldability, heat resistance, mechanical properties and the like but also a low specific gravity and are, therefore, widely utilized in a variety of molded articles such as films, sheets and structural components.

Meanwhile, although polyolefin resins also have excellent electrical insulation properties, they have a problem of being easily electrically charged by friction and the like. When a molded article composed of a polyolefin resin is electrically charged, its outer appearance may be deteriorated due to generation of static electricity and attraction of dust and dirt in the surroundings. When the molded article is an electronic product, an electric charge may interfere with normal circuit operation. Moreover, there are also problems caused by electric shock. An electric shock to a person from a resin not only causes discomfort but also potentially induces accidental explosion in the presence of flammable gas or dust.

In order to solve these problems, resins are conventionally subjected to an antistatic treatment. A common antistatic treatment is addition of an antistatic agent to a resin of interest. Examples of the antistatic agent include coating-type antistatic agents that are applied to the surface of a resin molded article and kneading-type antistatic agents that are added when a resin is molded; however, the coating-type antistatic agents have problems of not only having poor persistence but also being wiped off when an object comes into contact with the surface.

From this viewpoint, conventionally, kneading-type antistatic agents have been examined and, for example, the use of a polyether ester amide has been proposed for the purpose of imparting antistaticity to polyolefin-based resins (Patent Documents 1 and 2). In addition, a variety of kneading-type antistatic agents, such as a block polymer having a structure in which a polyolefin block and a hydrophilic polymer block are repeatedly and alternately bound with each other, have been proposed (Patent Documents 3 to 5).

Moreover, in polyolefin resins, in addition to the above-described problem that, since polyolefin resins have excellent electrical insulation properties but easily generate and accumulate static electricity, dust and the like are likely to adhere to the surface and this often leads to a reduction in their commercial values, there are also problems of a long molding cycle, which is attributed to their slow post-molding crystallization rate, and a reduction in transparency and strength, which is attributed to generation of large crystals inside the resulting molded articles caused by progress of crystallization after heat-molding.

In order to improve these problems, conventionally, a nucleator (also referred to as "nucleating agent", "crystallization accelerator", "crystallizer", "nucleophile" or "nucleus-forming agent") is added for the purpose of increasing the crystallization temperature of the subject polyolefin resin and thereby allowing fine crystals to be rapidly formed during molding, and a kneading-type antistatic agent is also added for the purpose of imparting the subject polyolefin resin with long-lasting antistaticity (Patent Documents 6 to 8).

RELATED ART DOCUMENTS

Patent Documents

Patent Document 1: Japanese Unexamined Patent Application Publication No. S58-118838
Patent Document 2: Japanese Unexamined Patent Application Publication No. H3-290464
Patent Document 3: Japanese Unexamined Patent Application Publication No. 2001-278985
Patent Document 4: WO 2014/115745
Patent Document 5: WO 2014/148454
Patent Document 6: Japanese Unexamined Patent Application Publication No. H6-67357
Patent Document 7: Japanese Unexamined Patent Application Publication No. H8-183889
Patent Document 8: Japanese Unexamined Patent Application Publication No. 2009-256474

SUMMARY OF THE INVENTION

Problems to be Solved by the Invention

However, the antistatic agents described in Patent Documents 1 to 3 do not exhibit sufficiently satisfactory antistatic performance, and there is a problem particularly in the persistence of their antistatic performances. Moreover, the antistatic agents described in Patent Documents 1 to 3 also have a problem of deteriorating the resin physical properties when added to polyolefin resins. The present applicant has proposed antistatic resin compositions comprising a polyether ester-based polymer-type antistatic agent in Patent Documents 4 and 5; however, since these compositions do not contain any aromatic dicarboxylic acid, their structures are different from that of the antistatic agent according to the present invention.

In view of the above, an object of the present invention is to provide a resin additive composition capable of imparting excellent antistatic effect in a small amount.

Further, those conventional antistatic agents that are described in Patent Documents 6 to 8 also do not exhibit sufficiently satisfactory antistatic performance, and there is a problem particularly in the persistence of their antistatic performances. Moreover, there is also a problem that addition of these antistatic agents to a polyolefin resin reduces the crystallization properties of the resin during molding.

In view of this, another object of the present invention is to provide an antistatic thermoplastic resin composition which exhibits long-lasting and sufficient antistaticity and crystallinity and has a short molding cycle at the time of molding. Yet another object of the present invention is to provide a thermoplastic resin molded article having excellent strength and excellent long-lasting antistaticity.

Means for Solving the Problems

The present inventors intensively studied to solve the above-described problems and discovered that the problems can be solved by using a combination of an antistatic polymer compound having a specific structure and a nucleator having a specific structure, thereby completing the present invention.

That is, the resin additive composition of the present invention is characterized by comprising two or more selected from aromatic metal phosphates (H) represented by the following Formula (3) or (4) in an amount of 0.001 to 50 parts by mass with respect to 100 parts by mass of a polymer compound (E), wherein the polymer compound (E) has a structure in which a diol, an aliphatic dicarboxylic acid, an aromatic dicarboxylic acid, a compound (B) which comprises at least one group represented by the following Formula (1) and has hydroxyl groups at both ends, and an epoxy compound (D) having two or more epoxy groups are bound via ester bonds:

$$—CH_2—CH_2—O— \quad (1)$$

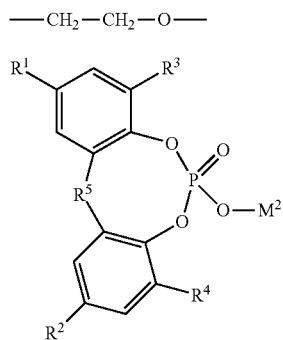

(3)

(wherein, $R^1$ to $R^4$ each independently represent a hydrogen atom or a linear or branched alkyl group having 1 to 9 carbon atoms; $R^5$ represents an alkylidene group having 1 to 4 carbon atoms; and $M^2$ represents an alkali metal)

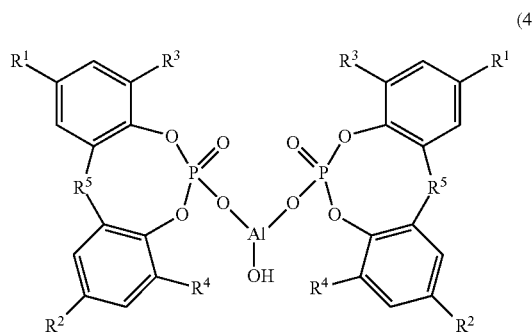

(4)

(wherein, $R^1$ to $R^4$ each independently represent a hydrogen atom or a linear or branched alkyl group having 1 to 9 carbon atoms; and $R^5$ represents an alkylidene group having 1 to 4 carbon atoms).

It is preferred that the additive composition of the present invention further comprises 10 to 50 parts by mass of a fatty acid metal salt (I) represented by the following Formula (5) with respect to a total of 100 parts by mass of two or more selected from the above-described aromatic metal phosphates (H):

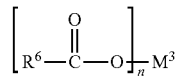

(5)

(wherein, $R^6$ represents an unsubstituted or hydroxy group-substituted aliphatic group having 1 to 40 carbon atoms; $M^3$ represents a metal atom; n is an integer of 1 to 4 and represents the valence of the metal atom $M^3$).

In the additive composition of the present invention, it is preferred that the above-described aromatic metal phosphates (H) are a mixture of a sodium salt compound represented by the Formula (3) wherein $M^2$ is sodium and a lithium salt compound represented by the Formula (3) wherein $M^2$ is lithium; and that the mass ratio of the sodium salt compound and the lithium salt compound (sodium salt compound/lithium salt compound) is in a range of 1/4 to 4/1.

In the additive composition of the present invention, it is also preferred that the polymer compound (E) has a structure in which a polyester (A), which is constituted by a diol, an aliphatic dicarboxylic acid and an aromatic dicarboxylic acid; the compound (B); and the epoxy compound (D), which are bound via ester bonds.

Further, in the additive composition of the present invention, it is preferred that the polymer compound (E) has a structure in which a block polymer (C) having carboxyl groups at both ends and the epoxy compound (D) are bound via an ester bond, the block polymer (C) comprising a block constituted by the polyester (A) and a block constituted by the compound (B) that are repeatedly and alternately bound via ester bonds.

Still further, in the additive composition of the present invention, it is preferred that the polyester (A) has a structure comprising carboxyl groups at both ends.

Yet still further, in the additive composition of the present invention, it is preferred that the block constituted by the polyester (A) has a number-average molecular weight of 800 to 8,000 in terms of polystyrene; the block constituted by the compound (B) has a number-average molecular weight of 400 to 6,000 in terms of polystyrene; and the block polymer (C) has a number-average molecular weight of 5,000 to 25,000 in terms of polystyrene.

Yet still further, in the additive composition of the present invention, it is preferred that the compound (B) is a polyethylene glycol.

The antistatic thermoplastic resin composition of the present invention is characterized by comprising, with respect to 100 parts by mass of a thermoplastic resin: 3 to 60 parts by mass of at least one polymer compound (E); and 0.001 to 10 parts by mass of at least one compound (F) represented by the following Formula (2), wherein the polymer compound (E) has a structure in which a diol, an aliphatic dicarboxylic acid, an aromatic dicarboxylic acid, a compound (B) which comprises at least one group represented by the following Formula (1) and has hydroxyl groups at both ends, and an epoxy compound (D) having two or more epoxy groups are bound via ester bonds:

—CH$_2$—CH$_2$—O— (1)

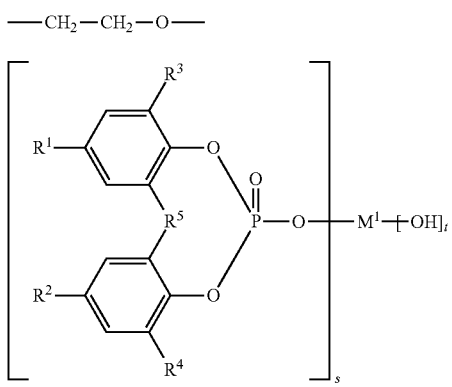

(2)

(wherein, R$^1$ to R$^4$ each independently represent a hydrogen atom or an alkyl group having 1 to 9 carbon atoms; R$^5$ represents an alkylidene group having 1 to 4 carbon atoms; M$^1$ represents an alkali metal atom, an alkaline earth metal atom, a beryllium atom, a magnesium atom or an aluminum atom; when M$^1$ is an alkali metal atom, s is 1 and t is 0; when M$^1$ is an alkaline earth metal atom, a beryllium atom or a magnesium atom, s is 2 and t is 0; and when M$^1$ is an aluminum atom, s is 1 or 2 and t is (3−s)).

In the resin composition of the present invention, it is preferred that the compound (F) is an aromatic metal phosphate (H) represented by the following Formula (3) or (4) and that two or more selected from such aromatic metal phosphates (H) are incorporated in an amount of 0.001 to 50 parts by mass with respect to 100 parts by mass of the polymer compound (E):

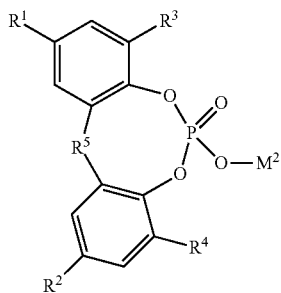

(3)

(wherein, R$^1$ to R$^4$ each independently represent the same as in the Formula (2); R$^5$ represents the same as in the Formula (2); and M$^2$ represents an alkali metal)

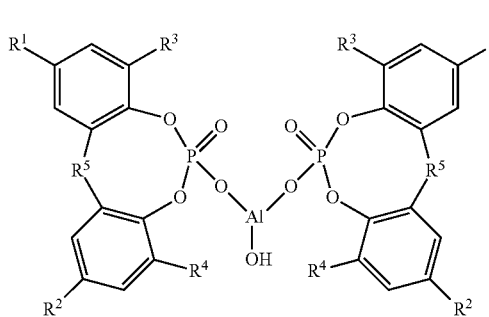

(4)

(wherein, R$^1$ to R$^5$ represent the same as in the Formula (3)).

It is also preferred that the resin composition of the present invention further comprises 10 to 50 parts by mass of a fatty acid metal salt (I) represented by the following Formula (5) with respect to a total of 100 parts by mass of two or more selected from the above-described aromatic metal phosphates (H):

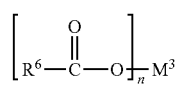

(5)

(wherein, R$^6$ represents an unsubstituted or hydroxy group-substituted aliphatic group having 1 to 40 carbon atoms; M$^3$ represents a metal atom; n is an integer of 1 to 4 and represents the valence of the metal atom M$^3$).

Further, in the resin composition of the present invention, it is preferred that the above-described aromatic metal phosphates (H) are a mixture of a sodium salt compound represented by the Formula (3) wherein M$^2$ is sodium and a lithium salt compound represented by the Formula (3) wherein M$^2$ is lithium; and that the mass ratio of the sodium salt compound and the lithium salt compound (sodium salt compound/lithium salt compound) is in a range of 1/4 to 4/1.

In the resin composition of the present invention, it is also preferred that the polymer compound (E) has a structure in which a polyester (A), which is constituted by a diol, an aliphatic dicarboxylic acid and an aromatic dicarboxylic acid, the compound (B) and the epoxy compound (D) are bound via ester bonds.

Further, in the resin composition of the present invention, it is preferred that the polymer compound (E) has a structure in which a block polymer (C) having carboxyl groups at both ends and the epoxy compound (D) are bound via an ester bond, the block polymer (C) comprising a block constituted by the polyester (A) and a block constituted by the compound (B) that are repeatedly and alternately bound via ester bonds.

Still further, in the resin composition of the present invention, it is preferred that the polyester (A) constituting the polymer compound (E) has a structure comprising carboxyl groups at both ends.

Yet still further, in the resin composition of the present invention, it is preferred that, in the polymer compound (E), the block constituted by the polyester (A) has a number-average molecular weight of 800 to 8,000 in terms of polystyrene; the block constituted by the compound (B) has a number-average molecular weight of 400 to 6,000 in terms of polystyrene; and the block polymer (C) has a number-average molecular weight of 5,000 to 25,000 in terms of polystyrene.

Yet still further, in the resin composition of the present invention, it is preferred that the compound (B) constituting the polymer compound (E) is a polyethylene glycol.

Yet still further, it is preferred that the resin composition of the present invention further comprises 0.01 to 5 parts by mass of at least one alkali metal salt (G) with respect to 100 parts by mass of the thermoplastic resin.

Yet still further, in the resin composition of the present invention, it is preferred that the thermoplastic resin is a polyolefin resin.

The molded article of the present invention is characterized in that it is obtained by molding the resin composition of the present invention.

EFFECTS OF THE INVENTION

According to the present invention, a resin additive composition capable of imparting resins, particularly polyolefin resins, with excellent antistaticity can be provided.

According to the present invention, an antistatic thermoplastic resin composition which exhibits long-lasting and sufficient antistaticity and crystallinity and has a short molding cycle at the time of molding can be provided. Moreover, according to the present invention, a thermoplastic resin molded article having excellent strength and excellent long-lasting antistaticity can be provided.

MODE FOR CARRYING OUT THE INVENTION

The present invention will now be described in detail.
[Resin Additive Composition and Antistatic Thermoplastic Resin Composition According to First Embodiment of the Present Invention]

First, the polymer compound (E) used in the present invention will be described.

The polymer compound (E) is an antistatic agent which is incorporated for the purpose of imparting antistaticity to a resin composition.

The polymer compound (E) used in the present invention can be produced by allowing a diol, an aliphatic dicarboxylic acid, an aromatic dicarboxylic acid, a compound (B) which comprises at least one group represented by the following Formula (1) and has hydroxyl groups at both ends, and an epoxy compound (D) having two or more epoxy groups to undergo an esterification reaction:

—CH$_2$—CH$_2$—O—       (1)

In the present invention, it is preferred that the polymer compound (E) has a structure in which a polyester (A), which is constituted by a diol, an aliphatic dicarboxylic acid and an aromatic dicarboxylic acid, the compound (B) and the epoxy compound (D) are bound via ester bonds.

The polyester (A) may be any polyester as long as it is composed of a diol, an aliphatic dicarboxylic acid and an aromatic dicarboxylic acid, and it is preferred that the polyester (A) has a structure in which a residue obtained by removing a hydroxyl group from the diol and a residue obtained by removing a carboxyl group from the aliphatic dicarboxylic acid are bound via an ester bond and the residue obtained by removing a hydroxyl group from the diol and a residue obtained by removing a carboxyl group from the aromatic dicarboxylic acid are bound via an ester bond.

It is also preferred that the polyester (A) has a structure comprising carboxyl groups at both ends and that the polymerization degree of the polyester (A) is in a range of 2 to 50.

Examples of the diol used in the present invention include aliphatic diols and aromatic group-containing diols. Two or more of these diols may be used in combination.

Examples of the aliphatic diols include 1,2-ethanediol (ethylene glycol), 1,2-propanediol (propylene glycol), 1,3-propanediol, 1,2-butanediol, 1,3-butanediol, 2-methyl-1,3-propanediol, 1,4-butanediol, 1,5-pentanediol, 2,2-dimethyl-1,3-propanediol (neopentyl glycol), 2,2-diethyl-1,3-propanediol (3,3-dimethylolpentane), 2-n-butyl-2-ethyl-1,3-propanediol (3,3-dimethylol heptane), 3-methyl-1,5-pentanediol, 1,6-hexanediol, 2,2,4-trimethyl-1,3-pentanediol, 2-ethyl-1,3-hexanediol, 2-methyl-1,8-octanediol, 1,9-nonanediol, 1,10-decanediol, 1,12-octadecanediol, 1,4-cyclohexane dimethanol, hydrogenated bisphenol A, 1.2-, 1,3- or 1,4-cyclohexanediol, cyclododecanediol, dimer diol, hydrogenated dimer diol, diethylene glycol, dipropylene glycol, triethylene glycol, and polyethylene glycol.

Among these aliphatic diols, 1,4-cyclohexane dimethanol and hydrogenated bisphenol A are preferred from the standpoint of the persistence of antistatic performance, and 1,4-cyclohexane dimethanol is more preferred.

The aliphatic diols are preferably hydrophobic; therefore, among aliphatic diols, a hydrophilic polyethylene glycol should not be used alone. This, however, does not apply to those cases where a hydrophilic polyethylene glycol is used in combination with a hydrophobic diol.

Examples of the aromatic group-containing diols include polyhydroxyethyl adducts of mononuclear dihydric phenol compounds, such as bisphenol A, 1,2-hydroxybenzene, 1,3-hydroxybenzene, 1,4-hydroxybenzene, 1,4-benzenedimethanol, bisphenol A-ethylene oxide adduct, bisphenol A-propylene oxide adduct, 1,4-bis(2-hydroxyethoxy)benzene, resorcin and pyrocatechol. Among these aromatic group-containing diols, from the standpoint of the persistence of antistatic performance, bisphenol A-ethylene oxide adduct and 1,4-bis(β-hydroxyethoxy)benzene are preferred.

Next, the aliphatic dicarboxylic acid used in the present invention will be described.

The aliphatic dicarboxylic acid may be a derivative (such as an acid anhydride, an alkyl ester, an alkali metal salt or an acid halide) of an aliphatic dicarboxylic acid and, in cases where the polyester (A) is produced using such a derivative, this polyester (A) may be subjected to reactions for eventually obtaining the block polymer (C) having a structure comprising carboxyl groups at both ends. Further, two or more aliphatic dicarboxylic acids and derivatives thereof may be used in combination.

The aliphatic dicarboxylic acid used in the present invention is preferably, for example, an aliphatic dicarboxylic acid having 2 to 20 carbon atoms, examples of which include oxalic acid, malonic acid, succinic acid, glutaric acid, adipic acid, pimelic acid, suberic acid, azelaic acid, sebacic acid, 1,10-decanedicarboxylic acid, 1,4-cyclohexanedicarboxylic acid, dimer acid, maleic acid, and fumaric acid. Among these aliphatic dicarboxylic acids, from the standpoints of the melting point and heat resistance, ones having 4 to 16 carbon atoms are preferred, and ones having 6 to 12 carbon atoms are more preferred.

Next, the aromatic dicarboxylic acid used in the present invention will be described.

The aromatic dicarboxylic acid may be a derivative (such as an acid anhydride, an alkyl ester, an alkali metal salt or an acid halide) of an aromatic dicarboxylic acid and, in cases where the polyester (A) is produced using such a derivative, this polyester (A) may be subjected to reactions for eventually obtaining the block polymer (C) having a structure comprising carboxyl groups at both ends. Further, two or more aromatic dicarboxylic acids and derivatives thereof may be used in combination.

The aromatic dicarboxylic acid used in the present invention is preferably, for example, an aromatic dicarboxylic acid having 8 to 20 carbon atoms, examples of which include terephthalic acid, isophthalic acid, phthalic acid, phenylmalonic acid, homophthalic acid, phenylsuccinic acid, β-phenylglutaric acid, α-phenyladipic acid, β-phenyladipic acid, biphenyl-2,2'-dicarboxylic acid, biphenyl-4, 4'-dicarboxylic acid, naphthalenedicarboxylic acid, sodium 3-sulfoisophthalate, and potassium 3-sulfoisophthalate.

Next, the compound (B) which comprises at least one group represented by the Formula (1) and has hydroxyl groups at both ends will be described.

The compound (B) is preferably a hydrophilic compound, particularly preferably a polyethylene glycol represented by the following Formula (6):

$$HO\text{---}[CH_2\text{---}CH_2\text{---}O]_m\text{---}H \qquad (6)$$

In the Formula (6), m represents an integer of 5 to 250. From the standpoints of the heat resistance and compatibility, m is preferably 20 to 150.

Examples of the compound (B) include polyethylene glycols obtained by addition reaction of ethylene oxide; and polyethers obtained by addition reaction of ethylene oxide and at least one other alkylene oxide (e.g., propylene oxide, or 1,2-, 1,4-, 2,3- or 1,3-butylene oxide), which polyethers may be random or block polyethers.

Examples of the compound (B) also include compounds having a structure in which ethylene oxide is added to an active hydrogen atom-containing compound; and compounds having a structure in which ethylene oxide and at least one other alkylene oxide (e.g., propylene oxide, or 1,2-, 1,4-, 2,3- or 1,3-butylene oxide) are added. The addition in these compounds may be random or block addition.

The active hydrogen atom-containing compound is, for example, a glycol, a dihydric phenol, a primary monoamine, a secondary diamine or a dicarboxylic acid.

As the glycol, for example, an aliphatic glycol having 2 to 20 carbon atoms, an alicyclic glycol having 5 to 12 carbon atoms or an aromatic glycol having 8 to 26 carbon atoms can be used.

Examples of the aliphatic glycol include ethylene glycol, 1,2-propylene glycol, 1,3-propanediol, 1,2-butanediol, 1,3-butanediol, 1,4-butanediol, 1,3-hexanediol, 1,4-hexanediol, 1,6-hexanediol, 2,5-hexanediol, 1,2-octanediol, 1,8-octanediol, 1,10-decanediol, 1,18-octadecanediol, 1,20-eicosanediol, diethylene glycol, triethylene glycol, and thiodiethylene glycol.

Examples of the alicyclic glycol include 1-hydroxymethyl-1-cyclobutanol, 1,2-cyclohexanediol, 1,3-cyclohexanediol, 1,4-cyclohexanediol, 1-methyl-3,4-cyclohexanediol, 2-hydroxymethylcyclohexanol, 4-hydroxymethylcyclohexanol, 1,4-cyclohexane dimethanol, and 1,1'-dihydroxy-1,1'-dicyclohexanol.

Examples of the aromatic glycol include dihydroxymethylbenzene, 1,4-bis(β-hydroxyethoxy)benzene, 2-phenyl-1,3-propanediol, 2-phenyl-1,4-butanediol, 2-benzyl-1,3-propanediol, triphenylethylene glycol, tetraphenylethylene glycol, and benzopinacol.

As the dihydric phenol, a phenol having 6 to 30 carbon atoms can be used, and examples thereof include catechol, resorcinol, 1,4-dihydroxybenzene, hydroquinone, bisphenol A, bisphenol F, bisphenol S, dihydroxydiphenyl ether, dihydroxydiphenyl thioether, binaphthol, and alkyl (C1 to C10) or halogen substitution products of these phenols.

Examples of the primary monoamine include aliphatic primary monoamines having 1 to 20 carbon atoms, such as methylamine, ethylamine, n-propylamine, isopropylamine, n-butylamine, s-butylamine, isobutylamine, n-amylamine, isoamylamine, n-hexylamine, n-heptylamine, n-octylamine, n-decylamine, n-octadecylamine and n-eicosylamine.

As the secondary diamine, for example, an aliphatic secondary diamine having 4 to 18 carbon atoms, a heterocyclic secondary diamine having 4 to 13 carbon atoms, an alicyclic secondary diamine having 6 to 14 carbon atoms, an aromatic secondary diamine having 8 to 14 carbon atoms or a secondary alkanoldiamine having 3 to 22 carbon atoms can be used.

Examples of the aliphatic secondary diamine include N,N'-dimethylethylenediamine, N,N'-diethylethylenediamine, N,N'-dibutylethylenediamine, N,N'-dimethylpropylenediamine, N,N'-diethylpropylenediamine, N,N'-dibutylpropylenediamine, N,N'-dimethyltetramethylenediamine, N,N'-diethyltetramethylenediamine, N,N'-dibutyltetramethylenediamine, N,N'-dimethylhexamethylenediamine, N,N'-diethylhexamethylenediamine, N,N'-dibutylhexamethylenediamine, N,N'-dimethyldecamethylenediamine, N,N'-diethyldecamethylenediamine, and N,N'-dibutyldecamethylenediamine.

Examples of the heterocyclic secondary diamine include piperazine and 1-aminopiperidine.

Examples of the alicyclic secondary diamine include N,N'-dimethyl-1,2-cyclobutanediamine, N,N'-diethyl-1,2-cyclobutanediamine, N,N'-dibutyl-1,2-cyclobutanediamine, N,N'-dimethyl-1,4-cyclohexanediamine, N,N'-diethyl-1,4-cyclohexanediamine, N,N'-dibutyl-1,4-cyclohexanediamine, N,N'-dimethyl-1,3-cyclohexanediamine, N,N'-diethyl-1,3-cyclohexanediamine, and N,N'-dibutyl-1,3-cyclohexanediamine.

Examples of the aromatic secondary diamine include N,N'-dimethyl-phenylenediamine, N,N'-dimethyl-xylylenediamine, N,N'-dimethyl-diphenylmethanediamine, N,N'-dimethyl-diphenyl ether diamine, N,N'-dimethyl-benzidine, and N,N'-dimethyl-1,4-naphthalenediamine.

Examples of the secondary alkanoldiamine include N-methyldiethanolamine, N-octyldiethanolamine, N-stearyldiethanolamine, and N-methyldipropanolamine.

As the dicarboxylic acid, a dicarboxylic acids having 2 to 20 carbon atoms can be used, and examples thereof include aliphatic dicarboxylic acids, aromatic dicarboxylic acids, and alicyclic dicarboxylic acids.

Examples of the aliphatic dicarboxylic acids include oxalic acid, malonic acid, succinic acid, glutaric acid, methylsuccinic acid, dimethylmalonic acid, β-methylglutaric acid, ethylsuccinic acid, isopropylmalonic acid, adipic acid, pimelic acid, suberic acid, azelaic acid, sebacic acid, undecanedicarboxylic acid, dodecanedicarboxylic acid, tridecanedicarboxylic acid, tetradecanedicarboxylic acid, hexadecanedicarboxylic acid, octadecanedicarboxylic acid, and eicosanedicarboxylic acid.

Examples of the aromatic dicarboxylic acids include terephthalic acid, isophthalic acid, phthalic acid, phenylmalonic acid, homophthalic acid, phenylsuccinic acid, β-phenylglutaric acid, α-phenyladipic acid, β-phenyladipic acid, biphenyl-2,2'-dicarboxylic acid, biphenyl-4,4'-dicarboxylic acid, naphthalenedicarboxylic acid, sodium 3-sulfoisophthalate, and potassium 3-sulfoisophthalate.

Examples of the alicyclic dicarboxylic acids include 1,3-cyclopentanedicarboxylic acid, 1,2-cyclopentanedicarboxylic acid, 1,4-cyclohexanedicarboxylic acid, 1,2-cyclohexanedicarboxylic acid, 1,3-cyclohexanedicarboxylic acid, 1,4-cyclohexanediacetic acid, 1,3-cyclohexanediacetic acid, 1,2-cyclohexanediacetic acid, and dicyclohexyl-4,4'-dicarboxylic acid.

These active hydrogen atom-containing compounds may be used individually, or two or more thereof may be used in combination.

Next, the epoxy compound (D) having two or more epoxy groups will be described.

The epoxy compound used in the present invention is not particularly restricted as long as it has two or more epoxy groups, and examples of such an epoxy compound include polyglycidyl ether compounds of mononuclear polyhydric phenol compounds, such as hydroquinone, resorcin, pyrocatechol and phloroglucinol; polyglycidyl ether compounds of polynuclear polyhydric phenol compounds, such as dihydroxynaphthalene, biphenyl, methylene bisphenol (bisphenol F), methylene bis(o-cresol), ethylidene bisphenol, isopropylidene bisphenol (bisphenol A), isopropylidene bis(o-cresol), tetrabromobisphenol A, 1,3-bis(4-hydroxycumylbenzene), 1,4-bis(4-hydroxycumylbenzene), 1,1,3-tris(4-hydroxyphenyl)butane, 1,1,2,2-tetra(4-hydroxyphenyl)ethane, thiobisphenol, sulfobisphenol, oxybisphenol, phenol novolac, o-cresol novolac, ethylphenol novolac, butylphenol novolac, octylphenol novolac, resorcin novolac and terpene phenol; polyglycidyl ethers of polyhydric alcohols, such as ethylene glycol, propylene glycol, butylene glycol, hexanediol, polyethylene glycol, polyglycol, thiodiglycol, glycerin, trimethylolpropane, pentaerythritol, sorbitol and bisphenol A-ethylene oxide adduct; homo- or co-polymers of glycidyl ester of an aliphatic, aromatic or alicyclic polybasic acid, such as maleic acid, fumaric acid, itaconic acid, succinic acid, glutaric acid, suberic acid, adipic acid, azelaic acid, sebacic acid, dimer acid, trimer acid, phthalic acid, isophthalic acid, terephthalic acid, trimellitic acid, trimesic acid, pyromellitic acid, tetrahydrophthalic acid, hexahydrophthalic acid or endomethylene tetrahydrophthalic acid, and glycidyl methacrylate; glycidylamino group-containing epoxy compounds, such as N,N-diglycidyl aniline, bis(4-(N-methyl-N-glycidylamino)phenyl)methane and diglycidyl o-toluidine; epoxidized cyclic olefin compounds, such as vinylcyclohexene diepoxide, dicyclopentadiene diepoxide, 3,4-epoxycyclohexylmethyl-3,4-epoxycyclohexane carboxylate, 3,4-epoxy-6-methylcyclohexylmethyl-6-methylcyclohexane carboxylate and bis(3,4-epoxy-6-methylcyclohexylmethyl)adipate; epoxidized conjugated diene polymers, such as epoxidized polybutadienes and epoxidized styrene-butadiene copolymers; heterocyclic compounds such as triglycidyl isocyanurate; and epoxidized soybean oil.

These epoxy compounds may be internally cross-linked by a prepolymer of terminal isocyanate, or may be allowed to have a high molecular weight using a multivalent active hydrogen compound (e.g., a polyhydric phenol, a polyamine, a carbonyl group-containing compound or a polyphosphoric acid ester). Such epoxy compounds may be used in a combination of two or more thereof.

From the standpoint of antistaticity, it is preferred that the polymer compound (E) has a structure in which a polyester (A), which is constituted by a diol, an aliphatic dicarboxylic acid and an aromatic dicarboxylic acid, the compound (B) and the epoxy compound (D) are bound via ester bonds.

Further, from the standpoint of antistaticity, it is preferred that the polymer compound (E) has a structure in which a block polymer (C) having carboxyl groups at both ends and the epoxy compound (D) are bound via an ester bond, the block polymer (C) comprising a block constituted by the polyester (A), which is constituted by a diol, an aliphatic dicarboxylic acid and an aromatic dicarboxylic acid, and a block constituted by the compound (B), which blocks are repeatedly and alternately bound via ester bonds.

The polyester (A) can be obtained by, for example, allowing the above-described aliphatic dicarboxylic acid and the above-described aromatic dicarboxylic acid to undergo a polycondensation reaction with the above-described diol.

The aliphatic dicarboxylic acid may be a derivative (such as an acid anhydride, an alkyl ester, an alkali metal salt or an acid halide) of an aliphatic dicarboxylic acid and, in cases where the polyester (A) is obtained using such a derivative, both ends of the polyester (A) can eventually be treated to be carboxyl groups, and the polyester (A) in this state may be directly subjected to the subsequent reaction for obtaining the block polymer (C) having a structure comprising carboxyl groups at both ends. Further, two or more aliphatic dicarboxylic acids and derivatives thereof may be used in combination.

The aromatic dicarboxylic acid may be a derivative (such as an acid anhydride, an alkyl ester, an alkali metal salt or an acid halide) of an aromatic dicarboxylic acid and, in cases where the polyester (A) is obtained using such a derivative, both ends of the polyester (A) can eventually be treated to be carboxyl groups, and the polyester (A) in this state may be directly subjected to the subsequent reaction for obtaining the block polymer (C) having a structure comprising carboxyl groups at both ends. Further, two or more aromatic dicarboxylic acids and derivatives thereof may be used in combination.

In the polyester (A), the molar ratio of a residue excluding the carboxyl groups of the aliphatic dicarboxylic acid and a residue excluding the carboxyl groups of the aromatic dicarboxylic acid is preferably 90:10 to 99.9:0.1, more preferably 93:7 to 99.9:0.1.

The polyester (A) can also be obtained by allowing the above-described aliphatic dicarboxylic acid or derivative thereof and the above-described aromatic dicarboxylic acid or derivative thereof to undergo a polycondensation reaction with the above-described diol.

As for the reaction ratio of the aliphatic dicarboxylic acid or derivative thereof and the aromatic dicarboxylic acid or derivative thereof with respect to the diol, it is preferred that the aliphatic dicarboxylic acid or derivative thereof and the aromatic dicarboxylic acid or derivative thereof are used in an excess amount, particularly in an excess of 1 mole in terms of molar ratio with respect to the diol, such that the resulting polyester has carboxyl groups at both ends.

In the polycondensation reaction, the compounding ratio of the aliphatic dicarboxylic acid or derivative thereof and the aromatic dicarboxylic acid or derivative thereof is, in terms of molar ratio, preferably 90:10 to 99.9:0.1, more preferably 93:7 to 99.9:0.1.

Depending on the compounding ratio and the reaction conditions, a polyester consisting of only the diol and the aliphatic dicarboxylic acid and a polyester consisting of only the diol and the aromatic dicarboxylic acid may be generated; however, in the present invention, the polyester (A) may contain such polyesters, or the block polymer (C) may be obtained by directly allowing such polyesters to react with the component (B).

In the polycondensation reaction, a catalyst which promotes esterification reaction may be used and, as the catalyst, a conventionally known catalyst, such as dibutyltin oxide, tetraalkyl titanate, zirconium acetate or zinc acetate, can be employed.

In cases where a derivative such as a carboxylic acid ester, metal carboxylate or carboxylic acid halide is used in place of the dicarboxylic acid of the aliphatic dicarboxylic acid and the aromatic dicarboxylic acid, after the derivative and the diol are allowed to react with each other, both ends of the resultant may be treated to be dicarboxylic acids, or the resultant may be directly subjected to the subsequent reaction for obtaining the block polymer (C) having a structure comprising carboxyl groups at both ends.

A preferred polyester (A), which is composed of a diol, an aliphatic dicarboxylic acid and an aromatic dicarboxylic acid, may be any polyester as long as it reacts with the component (B) to form an ester bond and thereby constitutes the structure of the block polymer (C). Further, the polyester (A) may have carboxyl groups at both ends, and the carboxyl groups may be protected or modified, or may be in a precursor form. Moreover, in order to inhibit oxidation of the product during the reaction, an antioxidant such as a phenolic antioxidant may be added to the reaction system.

The compound (B) may be any compound as long as it reacts with the polyester (A) to form an ester bond and thereby constitutes the structure of the block polymer (C), and the hydroxyl groups at both ends of the compound (B) may be protected or modified, or may be in a precursor form.

The block polymer (C) according to the present invention, which has a structure comprising carboxyl groups at both ends, contains a block constituted by the polyester (A) and a block constituted by the compound (B) and has a structure in which these blocks are repeatedly and alternately bound via polyester bonds formed by carboxyl groups and hydroxyl groups. One example of the block polymer (C) is a block polymer having a structure represented by the following Formula (7):

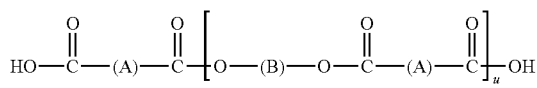

(7)

In the Formula (7), (A) represents a block constituted by the polyester (A) having carboxyl groups at both ends; (B) represents a block constituted by the compound (B) having at least one ethylene oxide group and hydroxyl groups at both ends; and u represents the number of repeating units, which is preferably 1 to 10, more preferably 1 to 7, most preferably 1 to 5.

In the block polymer (C), the block constituted by the polyester (A) may be partially replaced with a block constituted by a polyester consisting of only a diol and an aliphatic dicarboxylic acid or a block constituted by a polyester consisting of only a diol and an aromatic dicarboxylic acid.

The block polymer (C) having a structure comprising carboxyl groups at both ends can be obtained by allowing the polyester (A) and the compound (B) having hydroxyl groups at both ends to undergo a polycondensation reaction; however, as long as the block polymer (C) has a structure that is equivalent to the one in which the polyester (A) and the compound (B) are repeatedly and alternately bound via ester bonds formed by carboxyl groups and hydroxyl groups, it is not necessarily required that the block polymer (C) be synthesized from the polyester (A) and the compound (B).

As for the reaction ratio between the polyester (A) and the compound (B), by adjusting the amount of the polyester (A) to be (X+1) mol with respect to X mol of the compound (B), the block polymer (C) having carboxyl groups at both ends can be preferably obtained.

As for the reaction, after the completion of the synthesis reaction of the polyester (A) and without the thus synthesized polyester (A) being isolated, the compound (B) may be added to the reaction system and allowed to react with the polyester (A) as is.

In the polycondensation reaction, a catalyst which promotes esterification reaction may be used and, as the catalyst, a conventionally known catalyst, such as dibutyltin oxide, tetraalkyl titanate, zirconium acetate or zinc acetate, can be employed. Moreover, in order to inhibit oxidation of the product during the reaction, an antioxidant such as a phenolic antioxidant may be added to the reaction system.

Further, the polyester (A) may contain a polyester consisting of only a diol and an aliphatic dicarboxylic acid and/or a polyester consisting of only a diol and an aromatic dicarboxylic acid, and these polyesters may be directly allowed to react with the compound (B) to obtain the block polymer (C).

In addition to the block constituted by the polyester (A) and the block constituted by the compound (B), the block polymer (C) may also contain, in its structure, a block constituted by a polyester consisting of only a diol and an aliphatic dicarboxylic acid and/or a block constituted by a polyester consisting of only a diol and an aromatic dicarboxylic acid.

The polymer compound (E) according to the present invention has a structure in which the block polymer (C) having a structure comprising carboxyl groups at both ends and the epoxy compound (D) having two or more epoxy groups are bound via an ester bond formed by a terminal carboxyl group of the block polymer (C) and an epoxy group of the epoxy compound. The polymer compound (E) may further contain an ester bond formed by a carboxyl group of the polyester (A) and an epoxy group of the epoxy compound.

In order to obtain the polymer compound (E), the carboxyl groups of the block polymer (C) and the epoxy groups of the epoxy compound can be allowed to react with each other.

The number of the epoxy groups of the epoxy compound (D) is preferably 0.5 to 5 equivalents, more preferably 0.5 to 1.5 equivalents, with respect to the number of the carboxyl groups of the block polymer (C) to be reacted.

The amount of the epoxy compound (D) having two or more epoxy groups to be used in the reaction is preferably 0.1 to 2.0 equivalents, more preferably 0.2 to 1.5 equivalents, with respect to the carboxyl groups of the block polymer (C) to be reacted.

As for the reaction, after the completion of the synthesis reaction of the block polymer (C) and without the thus synthesized block polymer (C) being isolated, the epoxy compound (D) may be added to the reaction system and allowed to react with the block polymer (C) as is. In that case, unreacted carboxyl groups of the polyester (A) used in an excess amount in the synthesis of the block polymer (C) may react with some of the epoxy groups of the epoxy compound (D) to form ester bonds.

It is not necessarily restricted that a preferred polymer compound (E) of the present invention be synthesized from the block polymer (C) and the epoxy compound (D), as long as the polymer compound (E) has a structure that is equivalent to the one in which the block polymer (C) having a structure comprising carboxyl groups at both ends and the epoxy compound (D) are bound via an ester bond.

In the polymer compound (E) of the present invention, the block constituted by the polyester (A) has a number-average molecular weight of preferably 800 to 8,000, more preferably 1,000 to 6,000, still more preferably 2,000 to 4,000, in terms of polystyrene. Further, in the polymer compound (E), the block constituted by the compound (B) having hydroxyl groups at both ends has a number-average molecular weight of preferably 400 to 6,000, more preferably 1,000 to 5,000, still more preferably 2,000 to 4,000, in terms of polystyrene.

Moreover, in the polymer compound (E), the block constituted by the block polymer (C) having a structure comprising carboxyl groups at both ends has a number-average molecular weight of preferably 5,000 to 25,000, more preferably 7,000 to 17,000, still more preferably 9,000 to 13,000, in terms of polystyrene.

The polymer compound (E) of the present invention may also be obtained by preparing the polyester (A) from a diol, an aliphatic dicarboxylic acid and an aromatic dicarboxylic acid and then allowing the polyester (A) to react with the compound (B) and/or the epoxy compound (D) without isolating the polyester (A).

In cases where the polymer compound (E) is incorporated into a thermoplastic resin, the amount of the polymer compound (E) is 3 to 60 parts by mass with respect to 100 parts by mass of the thermoplastic resin and, from the standpoint of antistaticity, it is preferably 5 to 20 parts by mass, more preferably 7 to 15 parts by mass. When the amount of the polymer compound (E) is less than 3 parts by mass, sufficient antistaticity cannot be obtained, whereas when the amount is greater than 60 parts by mass, the physical properties of the resulting molded article may be adversely affected.

Next, the aromatic metal phosphates (H) used in the present invention will be described.

As the aromatic metal phosphates (H), two or more selected from the group consisting of compounds represented by the following Formula (3) or (4) are used:

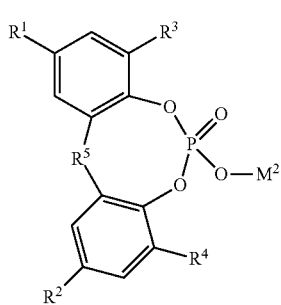

(3)

(wherein, $R^1$ to $R^4$ each independently represent a hydrogen atom or a linear or branched alkyl group having 1 to 9 carbon atoms; $R^5$ represents an alkylidene group having 1 to 4 carbon atoms; and $M^2$ represents an alkali metal)

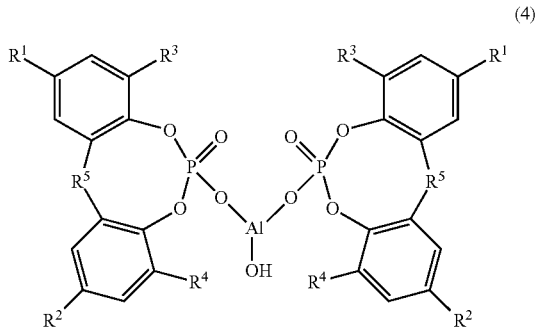

(4)

(wherein, $R^1$ to $R^4$ each independently represent a hydrogen atom or a linear or branched alkyl group having 1 to 9 carbon atoms; and $R^5$ represents an alkylidene group having 1 to 4 carbon atoms).

Examples of the linear or branched alkyl group having 1 to 9 carbon atoms which is represented by $R^1$ to $R^4$ in the Formula (3) include a methyl group, an ethyl group, a propyl group, an isopropyl group, a butyl group, a sec-butyl group, a tert-butyl group, an isobutyl group, an amyl group, a tert-amyl group, a hexyl group, a heptyl group, an octyl group, an isooctyl group, a tert-octyl group, a 2-ethylhexyl group, a nonyl group and an isononyl group, and $R^1$ to $R^4$ are preferably tert-butyl groups.

Examples of the alkylidene group having 1 to 4 carbon atoms which is represented by $R^5$ in the Formula (3) include a methylene group, an ethylidene group, a propylidene group and a butylidene group, and a methylene group is preferred in the present invention.

Examples of the alkali metal represented by $M^2$ in the Formula (3) include lithium, sodium and potassium, and lithium and sodium are preferred in the present invention.

Examples of a method of producing the aromatic metal phosphates (H) represented by the Formula (3) or (4) include a method of allowing a cyclic phosphoric acid having a corresponding structure to react with a metal compound (e.g., a metal hydroxide, a metal oxide, a metal halide, a metal sulfate, a metal nitrate or a metal alkoxide compound) using a reaction agent that is used as required, such as a basic compound; a method of allowing an alkali metal salt of a cyclic phosphoric acid ester having a corresponding structure to undergo a salt exchange reaction with a metal compound (e.g., a metal hydroxide, a metal oxide, a metal halide, a metal sulfate, a metal nitrate or a metal alkoxide compound) using a reaction agent that is used as required; and a method of generating a cyclic phosphoric acid by hydrolysis using cyclic phosphorus oxychloride as a starting substance and subsequently allowing the thus generated cyclic phosphoric acid to react with a metal compound.

In the resin composition of the present invention, it is preferred that the aromatic metal phosphates (H) are a mixture of an aromatic sodium phosphate compound represented by the Formula (3) wherein $M^2$ is sodium and an aromatic lithium phosphate compound represented by the Formula (3) wherein $M^2$ is lithium.

The ratio of the aromatic sodium phosphate compound and the aromatic lithium phosphate compound (aromatic sodium phosphate compound/aromatic lithium phosphate compound) is preferably in a range of 1/4 to 4/1 in terms of mass ratio.

When the ratio is outside the above-described range, the effects of the present invention may not be attained.

Specific examples of the compound represented by the Formula (3) include the following compounds. It is noted here, however, that the present invention is not restricted thereto.

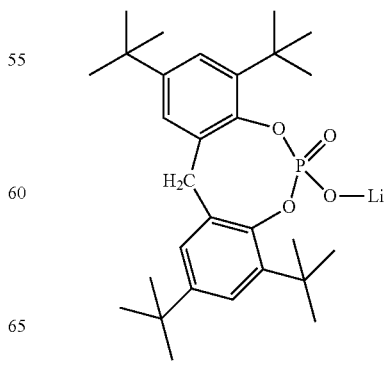

-continued

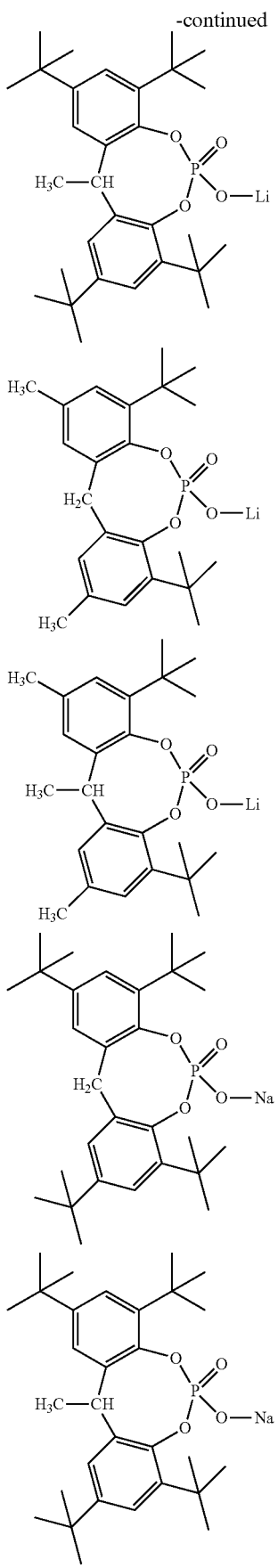

-continued

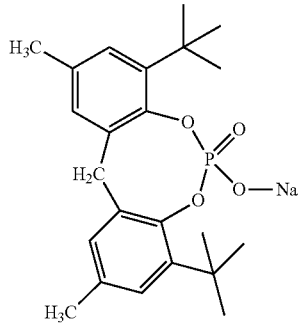

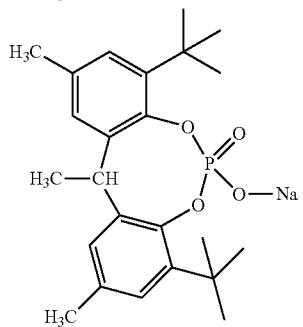

Specific examples of the compound represented by the Formula (4) include the following compounds. It is noted here, however, that the present invention is not restricted thereto.

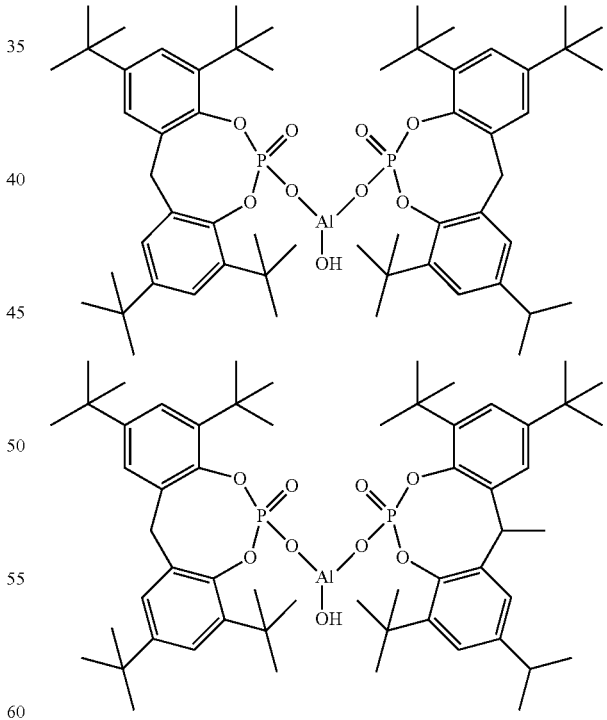

The two or more compounds selected from the group of the aromatic metal phosphates (H) represented by the Formula (3) or (4) are incorporated in an amount of 0.001 to 50 parts by mass, more preferably 0.01 to 10 parts by mass, with respect to 100 parts by mass of the polymer compound (E). When the amount is less than 0.001 parts by mass, the effects of the present invention may not be attained, whereas when the amount is greater than 50 parts by mass, it is difficult to disperse the compounds into the thermoplastic resin and this may adversely affect the physical properties and outer appearance of the resulting molded article.

Further, in the present invention, it is preferred to further incorporate 10 to 50 parts by mass of a fatty acid metal salt (I) represented by the following Formula (5) with respect to a total of 100 parts by mass of the two or more compounds selected from aromatic metal phosphates (H) represented by the Formula (3) or (4):

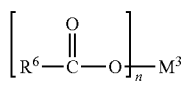
(5)

(wherein, $R^6$ represents an unsubstituted or hydroxy group-substituted aliphatic group having 1 to 40 carbon atoms; $M^3$ represents a metal atom; n is an integer of 1 to 4 and represents the valence of the metal atom $M^3$).

Examples of the aliphatic group having 1 to 40 carbon atoms that is represented by $R^6$ in the Formula (5) include hydrocarbon groups, such as alkyl groups, alkenyl groups and alkyl groups to which two or more unsaturated bonds are introduced, and the aliphatic group is optionally substituted with a hydroxyl group and/or branched.

Specific examples of the fatty acid include saturated fatty acids, such as acetic acid, propionic acid, butyric acid, valeric acid, isovaleric acid caproic acid, enanthic acid, caprylic acid, pelargonic acid, capric acid, 2-ethylhexanoic acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, cerotinic acid, montanoic acid and melissic acid, linear unsaturated fatty acids, such as 4-decenoic acid, 4-dodecenoic acid, palmitoleic acid, α-linolenic acid, linoleic acid, γ-linolenic acid, stearidonic acid, petroselinic acid, oleic acid, elaidic acid, vaccenic acid, eicosapentaenoic acid, docosapentaenoic acid and docosahexaenoic acid; and aromatic fatty acids such as trimesic acid.

In the present invention, aliphatic groups having 7 to 21 carbon atoms are preferred, and saturated fatty acids such as myristic acid, stearic acid and 12-hydroxystearic acid are particularly preferred.

Examples of the metal atom that is represented by $M^3$ in the Formula (5) include alkali metals, magnesium, calcium, strontium, barium, titanium, manganese, iron, zinc, silicon, zirconium, yttrium, and hafnium. Thereamong, alkali metals such as sodium, lithium and potassium can be particularly preferably used.

In the present invention, from the standpoints of performance and relative availability, the fatty acid metal salt (I) is, for example, preferably lithium stearate, sodium stearate, magnesium stearate, zinc stearate, aluminum stearate, lithium myristate, magnesium behenate or lithium 12-hydroxystearate, more preferably lithium myristate, lithium stearate or lithium 12-hydroxystearate.

The above-exemplified fatty acid metal salts can be produced by a synthesis method in which a carboxylic acid compound and a metal hydroxide are allowed to react with each other and the resultant is subsequently washed with water, dehydrated and dried (double decomposition method), or a synthesis method in which materials are allowed to directly react with each other without the use of water (direct method).

The amount of the fatty acid metal salt (I) to be incorporated is preferably in a range of 10 to 50 parts by mass with respect to a total of 100 parts by mass of the aromatic metal phosphates (H) represented by the Formula (3) or (4). When the amount is less than 10 parts by mass, the effects of the fatty acid metal salt (I) as a dispersant may not be obtained, whereas when the amount is greater than 50 parts by mass, the fatty acid metal salt (I) may adversely affect the nucleating effect of the aromatic metal phosphates.

Next, the antistatic thermoplastic resin composition of the present invention will be described.

As the thermoplastic resin in the thermoplastic resin composition of the present invention, any thermoplastic resin may be used, and examples thereof include polyolefin resins, styrene resins, polyester resins, polyether resins, polycarbonate resins, polyamide resins and halogen-containing resins, among which polyolefin resins are preferred. Examples of the polyolefin resins include α-olefin polymers, such as polyethylenes, low-density polyethylenes, linear low-density polyethylenes, high-density polyethylenes, polypropylenes, homopolypropylenes, random copolymer polypropylenes, block copolymer polypropylenes, isotactic polypropylenes, syndiotactic polypropylenes, hemi-isotactic polypropylenes, polybutenes, cycloolefin polymers, stereo block polypropylenes, poly-3-methyl-1-butene, poly-3-methyl-1-pentene and poly-4-methyl-1-pentene; α-olefin copolymers, such as ethylene-propylene block or random copolymers, impact copolymer polypropylenes, ethylene-methyl methacrylate copolymers, ethylene-methyl acrylate copolymers, ethylene-ethyl acrylate copolymers, ethylene-butyl acrylate copolymers and ethylene-vinyl acetate copolymers; and polyolefin-based thermoplastic elastomers, and these polyolefin resins may each be a copolymer of two or more polymers/elastomers.

Examples of the styrene resins include copolymers of vinyl group-containing aromatic hydrocarbon homopolymers, and copolymers of a vinyl group-containing aromatic hydrocarbon and other monomer(s) (e.g., maleic anhydride, phenylmaleimide, (meth)acrylate, butadiene and/or (meth)acrylonitrile), for example, thermoplastic resins such as polystyrene (PS) resins, high-impact polystyrenes (HIPS), acrylonitrile-styrene (AS) resins, acrylonitrile-butadiene-styrene (ABS) resins, methyl methacrylate-butadiene-styrene (MBS) resins, heat-resistant ABS resins, acrylonitrile-acylate-styrene (AAS) resins, styrene-maleic anhydride (SMA) resins, methacrylate-styrene (MS) resins, styrene-isoprene-styrene (SIS) resins, acrylonitrile-ethylene-propylene rubber-styrene (AES) resins, styrene-butadiene-butylene-styrene (SBBS) resins and methyl methacrylate-acrylonitrile-butadiene-styrene (MABS) resins; and hydrogenated styrene-based elastomer resins obtained by hydrogenation of the double bond of butadiene or isoprene in the above-described resins, such as styrene-ethylene-butylene-styrene (SEBS) resins, styrene-ethylene-propylene-styrene (SEPS) resins, styrene-ethylene-propylene (SEP) resins and styrene-ethylene-ethylene-propylene-styrene (SEEPS) resins.

Examples of the polyester resins include aromatic polyesters such as polyalkylene terephthalates (e.g., polyethylene terephthalate, polybutylene terephthalate and polycyclohexane dimethylene terephthalate) and polyalkylene naphthalates (e.g., polyethylene naphthalate and polybutylene naphthalate), and linear polyesters such as polytetramethylene terephthalate; and degradable aliphatic polyesters, such as polyhydroxy butyrate, polycaprolactone, polybutylene succinate, polyethylene succinate, polylactic acid, polymalic acid, polyglycolic acid, polydioxane and poly(2-oxetanone).

Examples of the polyether resins include polyacetal, polyphenylene ether, polyether ketone, polyether ether ketone, polyether ketone ketone, polyether ether ketone ketone, polyether sulfone, and polyether imide.

Examples of the polycarbonate resins include polycarbonates, polycarbonate/ABS resins, and branched polycarbonates.

Examples of the polyamide resins include polymers of ε-caprolactam (nylon 6), undecane lactam (nylon 11), lauryl lactam (nylon 12), aminocaproic acid, enanthlactam, 7-aminoheptanoic acid, 11-aminoundecanoic acid, 9-aminononanoic acid, α-pyrrolidone, α-piperidone and the like; copolymers obtained by copolymerization of a diamine (e.g., hexamethylenediamine, nonanediamine, nonanemethylenediamine, methylpentadiamine, undecanemethylenediamine, dodecanemethylenediamine or m-xylenediamine) and a carboxylic acid compound (e.g., a dicarboxylic acid such as adipic acid, sebacic acid, terephthalic acid, isophthalic acid, dodecanedicarboxylic acid or glutaric acid); and mixtures of these polymers and/or copolymers. Examples of the polyamide resins also include aramid resins such as "KEVLAR®" (trade name) manufactured by DuPont, "NOMEX®" (trade name) manufactured by DuPont, and "TWARON®" (trade name) and "CONEX®" (trade name) which are manufactured by TEIJIN Ltd.

Examples of the halogen-containing resins include polyvinyl chloride, polyvinylidene chloride, chlorinated polyethylene, chlorinated polypropylene, polyvinylidene fluoride, chlorinated rubbers, vinyl chloride-vinyl acetate copolymers, vinyl chloride-ethylene copolymers, vinyl chloride-vinylidene chloride copolymers, vinyl chloride-vinylidene chloride-vinyl acetate ternary copolymers, vinyl chloride-acrylate copolymers, vinyl chloride-maleate copolymers, and vinyl chloride-cyclohexylmaleimide copolymers.

Examples of the thermoplastic resin that can be used also include petroleum resins, coumarone resins, polyvinyl acetates, acrylic resins, polymethyl methacrylates, polyvinyl alcohols, polyvinyl formals, polyvinyl butyrals, polyphenylene oxides, polyphenylene sulfides, polyurethanes, cellulose-based resins, polyimide resins, polysulfones, liquid crystal polymers, and blends thereof.

Further, as the thermoplastic resin, an elastomer such as an isoprene rubber, a butadiene rubber, an acrylonitrile-butadiene copolymer rubber, a styrene-butadiene copolymer rubber, a fluorocarbon rubber, a silicone rubber, a polyester-based elastomer, a nitrile-based elastomer, a nylon-based elastomer, a vinyl chloride-based elastomer, a polyamide-based elastomer or a polyurethane-based elastomer may also be used.

In the resin composition of the present invention, these thermoplastic resins may be used individually, or two or more thereof may be used in combination. Further, these thermoplastic resins may be alloyed as well. These thermoplastic resins can be used regardless of molecular weight, polymerization degree, density, softening point, ratio of solvent-insoluble component(s), degree of stereoregularity, presence or absence of catalyst residue, type and blend ratio of each material monomer, type of polymerization catalyst (e.g., a Ziegler catalyst or a metallocene catalyst).

From the standpoint of improving the antistaticity and persistence thereof as well as the crystallization properties, it is preferred to incorporate at least one alkali metal salt (G) in the thermoplastic resin composition of the present invention.

Examples of the alkali metal salt (G) include salts of organic acids and inorganic acids.

Examples of the alkali metal include lithium, sodium, potassium, cesium and rubidium.

Examples of the organic acids include aliphatic monocarboxylic acids having 1 to 18 carbon atoms, such as formic acid, acetic acid, propionic acid, butyric acid, lactic acid, pentanoic acid, caproic acid, heptanoic acid, caprylic acid, pelargonic acid, capric acid, lauric acid, myristic acid, pentadecylic acid, palmitic acid, margaric acid, stearic acid and 12-hydroxystearic acid; aliphatic dicarboxylic acids having 1 to 12 carbon atoms, such as oxalic acid, malonic acid, succinic acid, fumaric acid, maleic acid and adipic acid; aromatic carboxylic acids, such as benzoic acid, phthalic acid, isophthalic acid, terephthalic acid and salicylic acid; and sulfonic acids having 1 to 20 carbon atoms, such as methanesulfonic acid, p-toluenesulfonic acid, dodecylbenzenesulfonic acid and trifluoromethanesulfonic acid.

Examples of the inorganic acids include hydrochloric acid, hydrobromic acid, sulfuric acid, sulfurous acid, phosphoric acid, phosphorous acid, polyphosphoric acid, nitric acid, and perchloric acid. Thereamong, from the standpoint of the antistaticity, lithium, sodium and potassium are more preferred, and lithium and sodium are most preferred. Further, from the standpoint of the antistaticity, acetates, perchlorates, p-toluenesulfonates and dodecylbenzenesulfonates are preferred.

Specific examples of the alkali metal salt (G) include lithium acetate, sodium acetate, potassium acetate, lithium butyrate, sodium butyrate, potassium butyrate, lithium laurate, sodium laurate, potassium laurate, lithium myristate, sodium myristate, potassium myristate, lithium palmitate, sodium palmitate, potassium palmitate, lithium stearate, sodium stearate, potassium stearate, lithium 12-hydroxystearate, sodium 12-hydroxystearate, potassium 12-hydroxystearate, lithium chloride, sodium chloride, potassium chloride, lithium phosphate, sodium phosphate, potassium phosphate, lithium sulfate, sodium sulfate, lithium perchlorate, sodium perchlorate, potassium perchlorate, lithium p-toluenesulfonate, sodium p-toluenesulfonate, potassium p-toluenesulfonate, lithium dodecylbenzenesulfonate, sodium dodecylbenzenesulfonate, and potassium dodecylbenzenesulfonate. Thereamong, for example, lithium acetate, potassium acetate, lithium p-toluenesulfonate, sodium p-toluenesulfonate, lithium dodecylbenzenesulfonate, sodium dodecylbenzenesulfonate and lithium chloride are preferred.

In the thermoplastic resin composition of the present invention, from the standpoints of the persistence of anti-static performance and the crystallization properties, the alkali metal salt (G) can be incorporated in an amount of 0.01 to 5.0 parts by mass, preferably 0.3 to 2.0 parts by mass, more preferably 0.4 to 1.0 part by mass, with respect to 100 parts by mass of the thermoplastic resin. When the amount of the alkali metal salt (G) is less than 0.01 parts by mass, satisfactory antistatic performance may not be attained, whereas when the amount is greater than 5.0 parts by mass, the alkali metal salt (G) may affect the physical properties of the thermoplastic resin.

In the thermoplastic resin composition of the present invention, a Group II element salt may further be incorporated in such a range that does not impair the effects of the present invention.

Examples of the Group II element salt include those of organic acids and inorganic acids, and examples of the Group II element include beryllium, magnesium, calcium, strontium and barium.

Examples of the organic acids include aliphatic monocarboxylic acids having 1 to 18 carbon atoms, such as formic acid, acetic acid, propionic acid, butyric acid and lactic acid: aliphatic dicarboxylic acids having 1 to 12 carbon atoms, such as oxalic acid, malonic acid, succinic acid, fumaric acid, maleic acid and adipic acid; aromatic carboxylic acids, such as benzoic acid, phthalic acid, isophthalic acid, terephthalic acid and salicylic acid; and sulfonic acids having 1 to 20 carbon atoms, such as methanesulfonic acid, p-toluenesulfonic acid, dodecylbenzenesulfonic acid and trifluoromethanesulfonic acid.

Examples of the inorganic acids include hydrochloric acid, hydrobromic acid, sulfuric acid, sulfurous acid, phosphoric acid, phosphorous acid, polyphosphoric acid, nitric acid, and perchloric acid.

In the thermoplastic resin composition of the present invention, a surfactant may also be incorporated in such a range that does not impair the effects of the present invention. As the surfactant, a nonionic, anionic, cationic or amphoteric surfactant can be used.

Examples of the nonionic surfactant include polyethylene glycol-type nonionic surfactants, such as higher alcohol ethylene oxide adducts, fatty acid ethylene oxide adducts, higher alkylamine ethylene oxide adducts and polypropylene glycol ethylene oxide adducts; and polyhydric alcohol-type nonionic surfactants, such as polyethylene oxides, glycerin fatty acid esters, pentaerythritol fatty acid esters, sorbitol or sorbitan fatty acid esters, polyhydric alcohol alkyl ethers and alkanolamine aliphatic amides.

Examples of the anionic surfactant include carboxylates, such as alkali metal salts of higher fatty acids; sulfates, such as higher alcohol sulfates and higher alkyl ether sulfates; sulfonates, such as alkylbenzenesulfonates, alkylsulfonates and paraffin sulfonates; and phosphates such as higher alcohol phosphates.

Examples of the cationic surfactant include quaternary ammonium salts such as alkyltrimethylammonium salts.

Examples of the amphoteric surfactant include amino acid-type amphoteric surfactants such as higher alkylaminopropionates; and betaine-type amphoteric surfactants, such as higher alkyl dimethylbetaines and higher alkyl dihydroxyethylbetaines. These surfactants may be used individually, or two or more thereof may be used in combination.

When a surfactant is incorporated, the amount thereof is preferably 0.1 to 5 parts by mass, more preferably 0.5 to 2 parts by mass, with respect to 100 parts by mass of the thermoplastic resin.

Further, in the thermoplastic resin composition of the present invention, a polymer-type antistatic agent may also be incorporated in such a range that does not impair the effects of the present invention. As the polymer-type antistatic agent, for example, a known polymer-type antistatic agent such as a polyether ester amide can be used, and examples thereof include the polyether ester amide disclosed in Japanese Unexamined Patent Application Publication No. H7-10989 which comprises a polyoxyalkylene adduct of bisphenol A. Further, a block polymer having 2 to 50 repeating structures each composed of a polyolefin block and a hydrophilic polymer block can be used as well, and examples thereof include the block polymer disclosed in the specification of U.S. Pat. No. 6,552,131.

When a polymer-type antistatic agent is incorporated, the amount thereof is preferably 0.1 to 10 parts by mass, more preferably 0.5 to 5 parts by mass, with respect to 100 parts by mass of the thermoplastic resin.

Still further, in the thermoplastic resin composition of the present invention, an ionic liquid may also be incorporated in such a range that does not impair the effects of the present invention. The ionic liquid is, for example, a normal temperature-molten salt having a melting point of not higher than room temperature and an initial electrical conductivity of 1 to 200 ms/cm preferably 10 to 200 ms/cm, in which at least one cation or anion constituting the ionic liquid is an organic ion. Examples of such a normal temperature-molten salt include the one disclosed in WO 95/15572.

The cation constituting the ionic liquid is, for example, one selected from the group consisting of amidinium, pyridinium, pyrazolium and guanidinium cations.

Examples of the amidinium cation include the followings:
(1) imidazolinium cations
  those having 5 to 15 carbon atoms, such as 1,2,3,4-tetramethylimidazolinium and 1,3-dimethylimidazolinium;
(2) imidazolium cations
  those having 5 to 15 carbon atoms, such as 1,3-dimethylimidazolium and 1-ethyl-3-methylimidazolium;
(3) tetrahydropyrimidinium cations
  those having 6 to 15 carbon atoms, such as 1,3-dimethyl-1,4,5,6-tetrahydropyrimidinium and 1,2,3,4-tetramethyl-1,4,5,6-tetrahydropyrimidinium; and
(4) dihydropyrimidinium cations
  those having 6 to 20 carbon atoms, such as 1,3-dimethyl-1,4-dihydropyrimidinium, 1,3-dimethyl-1,6-dihydropyrimidinium, 8-methyl-1,8-diazabicyclo[5,4,0]-7,9-undecadienium and 8-methyl-1,8-diazabicyclo[5,4,0]-7,10-undecadienium.

Examples of the pyridinium cation include those having 6 to 20 carbon atoms, such as 3-methyl-1-propylpyridinium and 1-butyl-3,4-dimethylpyridinium.

Examples of the pyrazolium cation include those having 5 to 15 carbon atoms, such as 1,2-dimethylpyrazolium and 1-n-butyl-2-methylpyrazolium.

Examples of the guanidinium cation include the followings:
(1) guanidinium cations having an imidazolinium skeleton
  those having 8 to 15 carbon atoms, such as 2-dimethylamino-1,3,4-trimethylimidazolinium and 2-diethylamino-1,3,4-trimethylimidazolinium;
(2) guanidinium cations having an imidazolium skeleton
  those having 8 to 15 carbon atoms, such as 2-dimethylamino-1,3,4-trimethylimidazolium and 2-diethyl amino-1,3,4-trimethylimidazolium;
(3) guanidinium cations having a tetrahydropyrimidinium skeleton
  those having 10 to 20 carbon atoms, such as 2-dimethylamino-1,3,4-trimethyl-1,4,5,6-tetrahydropyrimidinium and 2-diethyl amino-1,3-dimethyl-4-ethyl-1,4,5,6-tetrahydropyrimidinium; and
(4) guanidinium cations having a dihydropyrimidinium skeleton
  those having 10 to 20 carbon atoms, such as 2-dimethylamino-1,3,4-trimethyl-1,4-dihydropyrimidinium, 2-dimethylamino-1,3,4-trimethyl-1,6-dihydropyrimidinium, 2-diethylamino-1,3-dimethyl-4-ethyl-1,4-dihydropyrimidinium and 2-diethylamino-1,3-dimethyl-4-ethyl-1,6-dihydropyrimidinium.

The above-described cations may be used individually, or two or more thereof may be used in combination. Thereamong, from the standpoint of the antistaticity, amidinium cations are preferred, imidazolium cations are more preferred, and 1-ethyl-3-methylimidazolium cation is particularly preferred.

In the ionic liquid, examples of the organic or inorganic acid constituting the anion include the followings. Examples of the organic acid include carboxylic acid, sulfuric acid ester, sulfonic acid and phosphoric acid ester, and examples of the inorganic acid include superacids (such as fluoroboric acid, tetrafluoroboric acid, perchloric acid, hexafluorophosphoric acid, hexafluoroantimonic acid and hexafluoroarsenic acid), phosphoric acid and boric acid. These organic and inorganic acids may be used individually, or two or more thereof may be used in combination.

Among these organic and inorganic acids, from the standpoint of the antistaticity of the ionic liquid, acids forming a conjugate base of superacid or an anion other than a conjugate base of super acid, which allow the anion constituting the ionic liquid to have a Hammett acidity function ($-H_0$) of 12 to 100, and mixtures of such acids are preferred.

Examples of the anion other than a conjugate base of superacid include halogen (such as fluorine, chlorine and bromine) ions, alkyl (C1-C12) benzenesulfonic acid (such as p-toluenesulfonic acid and dodecylbenzenesulfonic acid) ions, and poly (n=1 to 25) fluoroalkanesulfonic acid (such as undecafluoropentanesulfonic acid) ions.

Examples of the superacid include those derived from a protonic acid or a combination of a protonic acid and a Lewis acid, and mixtures thereof. Examples of the protonic acid used as the superacid include bis(trifluoromethylsulfonyl)imidic acid, bis(pentafluoroethylsulfonyl)imidic acid, tris(trifluoromethylsulfonyl)methane, perchloric acid, fluorosulfonic acid, alkane (C1 to C30) sulfonic acids (such as methanesulfonic acid and dodecanesulfonic acid), poly (n=1 to 30) fluoroalkane (C1 to C30) sulfonic acid (such as trifluoromethanesulfonic acid, pentafluoroethanesulfonic acid, heptafluoropropanesulfonic acid, nonafluorobutanesulfonic acid, undecafluoropentanesulfonic acid and tridecafluorohexanesulfonic acid), fluoroboric acid, and tetrafluoroboric acid. Thereamong, from the standpoint of the ease of synthesis, fluoroboric acid, trifluoromethanesulfonic acid, bis(trifluoromethanesulfonyl)imidic acid and bis(pentafluoroethylsulfonyl)imidic acid are preferred.

Examples of the protonic acid used in combination with a Lewis acid include hydrogen halides (such as hydrogen fluoride, hydrogen chloride, hydrogen bromide and hydrogen iodide), perchloric acid, fluorosulfonic acid, methanesulfonic acid, trifluoromethanesulfonic acid, pentafluoroethanesulfonic acid, nonafluorobutanesulfonic acid, undecafluoropentanesulfonic acid, tridecafluorohexanesulfonic acid, and mixtures thereof. Thereamong, from the standpoint of the initial electrical conductivity of the ionic liquid, hydrogen fluoride is preferred.

Examples of the Lewis acid include boron trifluoride, phosphorus pentafluoride, antimony pentafluoride, arsenic pentafluoride, tantalum pentafluoride, and mixtures thereof. Thereamong, from the standpoint of the initial electrical conductivity of the ionic liquid, boron trifluoride and phosphorus pentafluoride are preferred.

The combination of a protonic acid and a Lewis acid may be any combination, and examples of a superacid derived therefrom include tetrafluoroboric acid, hexafluorophosphoric acid, hexafluorotantalic acid, hexafluoroantimonic acid, hexafluorotantalum sulfonic acid, tetrafluoroboric acid, hexafluorophosphoric acid, chlorotrifluoroboric acid, hexafluoroarsenic acid, and mixtures thereof.

Among the above-described anions, from the standpoint of the antistaticity of the ionic liquid, conjugate bases of superacids (superacids derived from a protonic acid and superacids derived from a combination of a protonic acid and a Lewis acid) are preferred, and superacids derived from a protonic acid and conjugate bases of superacids derived from a protonic acid, boron trifluoride and/or phosphorus pentafluoride are more preferred.

Among the above-described ionic liquids, from the standpoint of the antistaticity, amidinium cation-containing ionic liquids are preferred, 1-ethyl-3-methylimidazolium cation-containing ionic liquids are more preferred, and 1-ethyl-3-methylimidazolium-bis(trifluoromethanesulfonyl)imide is particularly preferred.

When an ionic liquid is incorporated, the amount thereof is preferably 0.01 to 5 parts by mass, more preferably 0.1 to 3 parts by mass, with respect to 100 parts by mass of the thermoplastic resin.

Yet still further, in the antistatic thermoplastic resin composition of the present invention, a compatibilizer may also be incorporated in such a range that does not impair the effects of the present invention. By incorporating a compatibilizer, the compatibility of the antistatic component with other components and the resin component can be improved. Examples of the compatibilizer include modified vinyl polymers having at least one functional group (polar group) selected from the group consisting of a carboxyl group, an epoxy group, an amino group, a hydroxyl group and a polyoxyalkylene group, such as the polymer disclosed in Japanese Unexamined Patent Application Publication No. H3-258850, the sulfonyl group-containing modified vinyl polymer disclosed in Japanese Unexamined Patent Application Publication No. H6-345927 and block polymers comprising a polyolefin moiety and an aromatic vinyl polymer moiety.

When a compatibilizer is incorporated, the amount thereof is preferably 0.01 to 5 parts by mass, more preferably 0.1 to 3 parts by mass, with respect to 100 parts by mass of the thermoplastic resin.

Moreover, in the antistatic thermoplastic resin composition of the present invention, any known resin additive(s) (e.g., a phenolic antioxidant, a phosphorus-based antioxidant, a thioether-based antioxidant, an ultraviolet absorber, a hindered amine compound, a nucleator different from the aromatic metal phosphates represented by the Formula (3) or (4), a flame retardant, a flame retardant aid, a lubricant, a filler, a hydrotalcite, an antistatic agent, a pigment and/or a dye) may also be incorporated in such a range that does not impair the effects of the present invention. These known resin additives may be incorporated into a thermoplastic resin separately from the resin additive composition of the present invention.

Examples of the phenolic antioxidant include 2,6-di-tert-butyl-4-ethylphenol, 2-tert-butyl-4,6-dimethylphenol, styrenated phenol, 2,2'-methylenebis(4-ethyl-6-tert-butylphenol), 2,2'-thiobis-(6-tert-butyl-4-methylphenol), 2,2'-thiodiethylenebis[3-(3,5-di-tert-butyl-4-hydroxyphenyl) propionate], 2-methyl-4,6-bis(octylsulfanylmethyl)phenol, 2,2'-isobutylidenebis(4,6-dimethylphenol), isooctyl-3-(3,5-di-tert-butyl-4-hydroxyphenyl)propionate, N,N'-hexane-1,6-diylbis[3-(3,5-di-tert-butyl-4-hydroxyphenyl)propionamide, 2,2'-oxamide-bis[ethyl-3-(3,5-di-tert-butyl-4-hydroxyphenyl)propionate], 2-ethylhexyl-3-(3',5'-di-tert-butyl-4'-hydroxyphenyl)propionate, 2,2'-ethylenebis(4,6-di-tert-butylphenol), esters of 3,5-di-tert-butyl-4-hydroxy-benzenepropanoic acid and a C13-15 alkyl, 2,5-di-tert-amylhydroquinone, hindered phenol polymer (AO.OH.998 (trade name), manufactured by ADEKA Palmarole), 2,2'-methylenebis[6-(1-methylcyclohexyl)-p-cresol], 2-tert-butyl-6-(3-tert-butyl-2-hydroxy-5-methylbenzyl)-4-methylphenyl acrylate, 2-[1-(2-hydroxy-3,5-di-tert-pentylphenyl)ethyl]-4,6-di-tert-pentylphenyl acrylate, 6-[3-(3-tert-butyl-4-hydroxy-5-methyl)propoxy]-2,4,8,10-tetra-tert-butylbenzo[d,f][1,3,2]-dioxaphosphepin, hexamethylene-bis[3-(3,5-di-tert-butyl-4-hydroxyphenyl)propionate calcium bis[monoethyl(3,5-di-tert-butyl-4-hydroxybenzyl)phosphonate, a reaction product between 5,7-bis(1,1-dimethylethyl)-3-hydroxy-2(3H)-benzofuranone and o-xylene, 2,6-di-tert-butyl-4-(4,6-bis(octylthio)-1,3,5-triazane-2-ylamino)phenol, DL-α-tocophenol (vitamin E), 2,6-bis(α-methylbenzyl)-4-methylphenol, bis[3,3-bis-(4'-hydroxy-3'-tert-butyl-phenyl)butyric acid]glycol ester, 2,6-di-tert-butyl-p-cresol, 2,6-diphenyl-4-octadecyloxyphenol, stearyl(3,5-di-tert-butyl-4-hydroxyphenyl)propionate, di stearyl(3,5-di-tert-butyl-4-hydroxybenzyl)phosphonate, tridecyl-3,5-di-ter-butyl-4-hydroxybenzyl thioacetate, thiodiethylene-bis[(3,5-di-tert-butyl-4-hydroxyphenyl)propionate], 4,4'-thiobis(6-ter-butyl-m-cresol), 2-octyl thio-4,6-di(3,5-di-tert-butyl-4-hydroxyphenoxy)-s-triazine, 2,2'-methylenebis(4-methyl-6-tert-butylphenol), bis[3,3-bis(4-hydroxy-3-tert-butylphenyl)butyric acid]glycol ester 4,4'-butylidenebis(2,6-di-tert-butylphenol), 4,4'-butylidenebis((6-tert-butyl-3-methylphenol), 2,2'-ethylidenebis(4,6-di-ter-butylphenol), 1,1,3-tris(2-methyl-4-hydroxy-5-tert-butylphenyl)butane, bis[2-tert-butyl-4-methyl-6-(2-hydroxy-3-ter-butyl-5-methylbenzyl)phenyl]terephthalate, 1,3,5-tris(2,6-dimethyl-3-hydroxy-4-tert-butylbenzyl)isocyanurate, 1,3,5-tris(3,5-di-tert-butyl-4-hydroxybenzyl)isocyanurate, 1,3,5-tris(3,5-di-tert-butyl-4-hydroxybenzyl)-2,4,6-trimethylbenzene, 1,3,5-tris[(3,5-di-tert-butyl-4-hydroxyphenyl)propionyloxyethyl] isocyanurate, tetrakis[methylene-3-(3',5'-di-tert-butyl-4'-hydroxyphenyl)propionate]methane, 2-tert-butyl-4-methyl-6-(2-acryloyloxy-3-tert-butyl-5-methylbenzyl)phenol, 3,9-bis[2-(3-tert-butyl-4-hydroxy-5-methylhydrocinnamoyloxy)-1,1-dimethylethyl]-2,4,8,10-tetraoxaspiro[5.5]undecane, triethylene glycol-bis[β-(3-tert-butyl-4-hydroxy-5-methylphenyl)propionate], and 3-(3,5-dialkyl-4-hydroxyphenyl)propionic acid derivatives such as stearyl-3-(3,5-di-tert-butyl-4-hydroxyphenyl)propionic acid amide, palmityl-3-(3,5-di-tert-butyl-4-hydroxyphenyl)propionic acid amide, myristyl-3-(3,5-di-tert-butyl-4-hydroxyphenyl)propionic acid amide and lauryl-3-(3,5-di-tert-butyl-4-hydroxyphenyl) propionic acid amide.

When a phenolic antioxidant is incorporated, the amount thereof is preferably 0.001 to 5 parts by mass, more preferably 0.03 to 3 parts by mass, with respect to 100 parts by mass of the thermoplastic resin.

Examples of the phosphorus-based antioxidant include triphenyl phosphite, diisooctyl phosphite, heptakis(dipropylene glycol)triphosphite, triisodecyl phosphite, diphenylisooctyl phosphite, diisooctylphenyl phosphite, diphenyltridecyl phosphite, triisooctyl phosphite, trilauryl phosphite, diphenyl phosphite, tris(dipropylene glycol) phosphite, diisodecylpentaerythritol diphosphite, dioleyl hydrogen phosphite, trilauryl trithiophosphite, bis(tridecyl) phosphite, tris(isodecyl)phosphite, tris(tridecyl)phosphite, diphenyldecyl phosphite, dinonylphenyl-bis(nonylphenyl) phosphite, poly(dipropylene glycol)phenyl phosphite, tetraphenyl dipropyl glycol diphosphite, trisnonylphenyl phosphite, tris(2,4-di-tert-butylphenyl)phosphite, tris(2,4-di-tert-butyl-5-methylphenyl)phosphite, tris[2-tert-butyl-4-(3-tert-butyl-4-hydroxy-5-methylphenylthio)-5-methylphenyl] phosphite, tri(decyl) phosphite, octyldiphenyl phosphite, di(decyl)monophenyl phosphite, distearyl pentaerythritol diphosphite, a mixture of distearyl pentaerythritol and calcium stearate, alkyl(C10) bisphenol-A phosphite, di(tridecyl)pentaerythritol diphosphite, di(nonylphenyl)pentaerythritol diphosphite, bis(2,4-di-tert-butylphenyl)pentaerythritol diphosphite, bis(2,6-di-tert-butyl-4-methylphenyl)pentaerythritol diphosphite, bis(2,4,6-tri-tert-butylphenyl)pentaerythritol diphosphite, bis(2,4-dicumylphenyl)pentaerythritol diphosphite, tetraphenyl-tetra(tridecyl)pentaerythritol tetraphosphite, bis(2,4-di-tert-butyl-6-methylphenyl)ethyl phosphite, tetra(tridecyl)isopropylidene diphenol diphosphite, tetra(tridecyl)-4,4'-n-butylidene-bis(2-tert-butyl-5-methylphenol)diphosphite, hexa(tridecyl)-1,1,3-tris(2-methyl-4-hydroxy-5-tert-butylphenyl)butane triphosphite, tetrakis(2,4-di-tert-butylphenyl)biphenylene diphosphonite, 9,10-dihydro-9-oxa-10-phosphaphenanthrene-10-oxide, (1-methyl-1-propanyl-3-ylidene)-tris(1,1-dimethylethyl)-5-methyl-4, 1-phenylene)hexatridecyl phosphite, 2,2'-methylene-bis(4,6-di-tert-butylphenyl)-2-ethylhexyl phosphite, 2,2'-methylene-bis(4,6-di-tert-butylphenyl)-octadecyl phosphite, 2,2'-ethylidene-bis(4,6-di-tert-butylphenyl)fluorophosphite, 4,4'-butylidene-bis(3-methyl-6-tert-butylphenylditridecyl)phosphite, tris(2-[(2,4,8,10-tetrakis-tert-butyldibenzo[d,f][1,3,2]dioxaphosphepin-6-yl)oxy]ethyl)amine, 3,9-bis(4-nonylphenoxy)-2,4,8,10-tetraoxa-3,9-diphosphaspiro[5,5]undecane, 2,4,6-tri-tert-butylphenyl-2-butyl-2-ethyl-1,3-propanediol phosphite, and poly-4,4'-isopropylidene diphenol C12-15 alcohol phosphite.

When a phosphorus-based antioxidant is incorporated, the amount thereof is preferably 0.001 to 10 parts by mass, more preferably 0.01 to 0.5 parts by mass, with respect to 100 parts by mass of the thermoplastic resin.

Examples of the thioether-based antioxidant include tetrakis[methylene-3-(laurylthio)propionate]methane, bis (methyl-4-[3-n-alkyl(C12/C14)thiopropionyloxy]-5-tert-butylphenyl)sulfide, ditridecyl-3,3'-thiodipropionate, dilauryl-3,3'-thiodipropionate, dimyristyl-3,3'-thiodipropionate, distearyl-3,3'-thiodipropionate, lauryl/stearyl thiodipropionate, 4,4'-thiobis(6-tert-butyl-m-cresol), 2,2'-thiobis(6-tert-butyl-p-cresol), and distearyl disulfide.

When a thioether-based antioxidant is incorporated, the amount thereof is preferably 0.001 to 10 parts by mass, more preferably 0.01 to 0.5 parts by mass, with respect to 100 parts by mass of the thermoplastic resin.

Examples of the ultraviolet absorber include 2-hydroxybenzophenones, such as 2,4-dihydroxybenzophenone and 5,5'-methylene-bis(2-hydroxy-4-methoxybenzophenone), 2-(2-hydroxyphenyl)benzotriazoles, such as 2-(2-hydroxy-5-methylphenyl)benzotriazole, 2-(2-hydroxy-5-tert-octylphenyl) benzotriazole, 2-(2-hydroxy-3,5-di-tert-butylphenyl)-5-chlorobenzotriazole, 2-(2-hydroxy-3-tert-butyl-5-methylphenyl)-5-chlorobenzotriazole, 2-(2-hydroxy-3,5-dicumylphenyl)benzotriazole, 2,2'-methylene-bis(4-tert-octyl-6-benzotriazolylphenol), polyethylene glycol esters of 2-(2-hydroxy-3-tert-butyl-5-carboxyphenyl)benzotriazole, 2-[2-hydroxy-3-(2-acryloyloxyethyl)-5-methylphenyl]benzotriazole, 2-[2-hydroxy-3-(2-methacryloyloxyethyl)-5-tert-butylphenyl]benzotriazole, 2-[2-hydroxy-3-(2-methacryloyloxyethyl)-5-tert-octylphenyl]benzotriazole, 2-[2-hydroxy-3-(2-methacryloyloxyethyl)-5-tert-butylphenyl]-5-chlorobenzotriazole, 2-[2-hydroxy-5-(2-methacryloyloxyethyl)phenyl]benzotriazole, 2-[2-hydroxy-3-tert-butyl-5-(2-methacryloyloxyethyl)phenyl]benzotriazole, 2-[2-hydroxy-3-tert-amyl-5-(2-methacrloyloxyethyl)phenyl]benzotriazole, 2-[2-hydroxy-3-tert-butyl-5-(3-methacryloyloxypropyl)phenyl]-5-chlorobenzotriazole, 2-[2-hydroxy-4-(2-methacryloyloxymethyl)phenyl]benzotriazole, 2-[2-hydroxy-4-(3-methacryloyloxy-2-hydroxypropyl)phenyl]benzotriazole and 2-[2-hydroxy-4-(3-methacryloyloxypropyl)phenyl]benzotriazole; benzoates, such as phenyl salicylate, resorcinol monobenzoate, 2,4-di-tert-butylphenyl-3,5-di-tert-butyl-4-hydroxybenzoate, octyl(3,5-di-tert-butyl-4-hydroxy)benzoate dodecyl(3,5-di-tert-butyl-4-hydroxy)benzoate, tetradecyl(3,5-di-tert-butyl-4-hydroxy)benzoate, hexadecyl(3,5-di-tert-butyl-4-hydroxy)benzoate, octadecyl(3,5-di-tert-butyl-4-hydroxy)benzoate and behenyl(3,5-di-tert-butyl-4-hydroxy)benzoate; substituted oxanilides such as 2-ethyl-2'-ethoxyoxanilide and 2-ethoxy-4'-dodecyloxanilide; cyanoacrylates, such as ethyl-α-cyano-β,β-diphenylacrylate and methyl-2-cyano-3-methyl-3-(p-methoxyphenyl)acrylate; and a variety of metal salts and metal chelates, particularly salts and chelates of nickel and chromium.

When any of the above-described ultraviolet absorbers is incorporated, the amount thereof is preferably 0.001 to 10 parts by mass, more preferably 0.005 to 0.5 parts by mass, with respect to 100 parts by mass of the thermoplastic resin.

Examples of the hindered amine compound include 2,2,6,6-tetramethyl-4-piperidyl stearate, 1,2,2,6,6-pentamethyl-4-piperidyl stearate, 2,2,6,6-tetramethyl-4-piperidyl benzoate, bis(2,2,6,6-tetramethyl-4-piperidyl)sebacate, tetrakis(2,2,6,6-tetramethyl-4-piperidyl)-1,2,3,4-butanetetracarboxylate, tetrakis(1,2,2,6,6-pentamethyl-4-piperidyl)-1,2,3,4-butanetetracarboxylate, bis(2,2,6,6-tetramethyl-4-piperidyl).di(tridecyl)-1,2,3,4-butanetetracarboxylate, bis(1,2,2,6,6-pentamethyl-4-piperidyl).di(tridecyl)-1,2,3,4-butanetetracarboxylate, bis(1,2,2,4,4-pentamethyl-4-piperidyl)-2-butyl-2-(3,5-di-tert-butyl-4-hydroxybenzyl)malonate, 1-(2-hydroxyethyl)-2,2,6,6-tetramethyl-4-piperidinol/diethyl succinate polycondensate, 1,6-bis(2,2,6,6-tetramethyl-4-piperidylamino)hexane/2,4-dichloro-6-morpholino-s-triazine polycondensate, 1,6-bis(2,2,6,6-tetramethyl-4-piperidylamino)hexane/2,4-dichloro-6-tert-octylamino-s-triazine polycondensate, 1,5,8,12-tetrakis[2,4-bis(N-butyl-N-(2,2,6,6-tetramethyl-4-piperidyl)amino)-s-triazine-6-yl]-1, 5,8,12-tetraazadodecane, 1,5,8,12-tetrakis[2,4-bis(N-butyl-N-(1,2,2,6,6-pentamethyl-4-piperidyl)amino)-s-triazine-6-yl]-1,5,8,12-tetraazadodecane, 1,6,11-tris[2,4-bis(N-butyl-N-(2,2,6,6-tetramethyl-4-piperidyl)amino)-s-triazine-6-yl]aminoun decane, 1,6,11-tris[2,4-bis(N-butyl-N-(1,2,2,6,6-pentamethyl-4-piperidyl)amino)-s-triazine-6-yl]amino undecane, bis{4-(1-octyloxy-2,2,6,6-tetramethyl) piperidyl}decanedionate, bis{4-(2,2,6,6-tetramethyl-1-undecyloxy)piperidyl)carbonate, and TINUVIN® NOR™ 371 manufactured by Ciba Specialty Chemicals K.K.

When any of the above-described hindered amine compounds is incorporated, the amount thereof is preferably 0.001 to 5 parts by mass, more preferably 0.005 to 0.5 parts by mass, with respect to 100 parts by mass of the thermoplastic resin.

Examples of the nucleator different from the aromatic metal phosphates represented by the Formula (3) or (4) include metal carboxylates, such as sodium benzoate, aluminum 4-tert-butylbenzoate, sodium adipate and 2-sodium-bicyclo[2.2.1]heptane-2,3-dicarboxylate; polyhydric alcohol derivatives, such as dibenzylidene sorbitol, bis (methylbenzylidene)sorbitol, bis(3,4-dimethylbenzylidene) sorbitol, bis(p-ethylbenzylidene)sorbitol and bis (dimethylbenzylidene)sorbitol; and amide compounds, such as N,N',N''-tris[2-methylcyclohexyl]-1,2,3-propane tricarboxamide, N,N',N''-tricyclohexyl-1,3,5-benzene tricarboxamide, N,N'-dicyclohexylnaphthalene dicarboxamide and 1,3,5-tri(dimethylisopropoylamino)benzene.

When any of the above-described nucleators is incorporated, the total amount of the nucleator and the aromatic metal phosphates (H) is preferably 0.001 to 5 parts by mass, more preferably 0.005 to 0.5 parts by mass, with respect to 100 parts by mass of the thermoplastic resin.

Examples of the flame retardant include aromatic phosphates, such as triphenyl phosphate, tricresyl phosphate, trixylenyl phosphate, cresyldiphenyl phosphate, cresyl-2,6-dixylenyl phosphate, resorcinol-bis(diphenylphosphate); (1-methylethylidene)-4,1-phenylene tetraphenyldiphosphate, 1,3-phenylene-tetrakis(2,6-dimethylphenyl)phosphate, ADK STAB FP-500 (manufactured by ADEKA Corporation), ADK STAB FP-600 (manufactured by ADEKA Corporation) and ADK STAB FP-800 (manufactured by ADEKA Corporation); phosphonates, such as divinyl phenylphosphonate, diallyl phenylphosphonate and (1-butenyl) phenylphosphonate; phosphinates, such as phenyl diphenylphosphinate, methyl diphenylphosphinate and 9,10-dihydro-9-oxa-10-phosphaphenanthlene-10-oxide derivatives; phosphazene compounds, such as bis(2-allylphenoxy)phosphazene and dicresylphosphazene; phosphorus-based flame retardants, such as melamine phosphate, melamine pyrophosphate, melamine polyphosphate, melam polyphosphate, ammonium polyphosphate, piperazine phosphate, piperazine pyrophosphate, piperazine polyphosphate, phosphorus-containing vinylbenzyl compounds and red phosphorus; metal hydroxides, such as magnesium hydroxide and aluminum hydroxide; and bromine-based flame retardants, such as brominated bisphenol A-type epoxy resins, brominated phenol novolac-type epoxy resins, hexabromobenzene, pentabromotoluene, ethylene-bis(pentabromophenyl), ethylene-bis-tetrabromophthalimide, 1,2-dibromo-4-(1,2-dibromoethyl)cyclohexane, tetrabromocyclooctane, hexabromocyclododecane, bis(tribromophenoxy)ethane, brominated polyphenylene ether, brominated polystyrene, 2,4,6-tris(tribromophenoxy)-1,3,5-triazine, tribromophenyl maleimide, tribromophenyl acrylate, tribromophenyl methacrylate, tetrabromobisphenol A-type dimethacrylate, pentabromobenzyl acrylate and brominated styrene. These flame retardants are preferably used in combination with a drip inhibitor such as a fluorocarbon resin and/or a flame retardant aid such as a polyhydric alcohol or hydrotalcite.

When any of the above-described flame retardants is incorporated, the amount thereof is preferably 1 to 50 parts by mass, more preferably 10 to 30 parts by mass, with respect to 100 parts by mass of the thermoplastic resin.

The lubricant is added for the purposes of imparting the surface of the resulting molded article with lubricity and improving the damage-preventing effect. Examples of the lubricant include unsaturated fatty acid amides, such as oleic acid amide and erucic acid amide; saturated fatty acid amides, such as behenic acid amide and stearic acid amide; butyl stearate; stearyl alcohols; stearic acid monoglyceride; sorbitan monopalmitate; sorbitan monostearate; mannitol; stearic acid; hardened castor oil; stearic acid amide; oleic acid amide; and ethylenebis stearic acid amide. These lubricants may be used individually, or two or more thereof may be used in combination.

When any of the above-described lubricants is incorporated, the amount thereof is preferably 0.01 to 2 parts by mass, more preferably 0.03 to 0.5 parts by mass, with respect to 100 parts by mass of the thermoplastic resin.

Examples of the filler include talc, mica, calcium carbonate, calcium oxide, calcium hydroxide, magnesium carbonate, magnesium hydroxide, magnesium oxide, magnesium sulfate, aluminum hydroxide, barium sulfate, glass powder, glass fibers, clays, dolomite, mica, silica, alumina, potassium titanate whiskers, wollastonite and fibrous magnesium oxysulfate, and any of these fillers can used by appropriately selecting the particle size (the fiber diameter, fiber length and aspect ratio in the case of a fibrous filler). Further, the filler to be used can be subjected to a surface treatment as required.

When any of the above-described fillers is incorporated, the amount thereof is preferably 0.01 to 80 parts by mass, more preferably 1 to 50 parts by mass, with respect to 100 parts by mass of the thermoplastic resin.

As the metallic soap, salts formed by a metal, such as magnesium, calcium, aluminum or zinc, and a saturated or unsaturated fatty acid, such as lauric acid, myristic acid, palmitic acid, stearic acid, behenic acid or oleic acid, can be used.

When any of these metallic soaps is incorporated, the amount thereof is preferably 0.001 to 10 parts by mass, more preferably 0.01 to 5 parts by mass, with respect to 100 parts by mass of the thermoplastic resin.

The hydrotalcite is a complex salt compound which is known as a natural or synthetic product and composed of magnesium, aluminum, hydroxyl groups, a carbonate group and arbitrary crystal water, and examples thereof include hydrotalcites in which some of the magnesium or aluminum atoms are substituted with other metal such as an alkali metal or zinc; and hydrotalcites in which the hydroxyl group(s) and/or carbonate group is/are substituted with other anionic group(s), specifically, hydrotalcites represented by the following Formula (8) in which a metal is substituted with an alkali metal. In addition, as an Al—Li hydrotalcite, a compound represented by the following Formula (9) can be used as well.

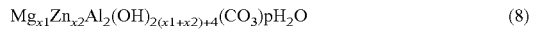

$$Mg_{x1}Zn_{x2}Al_2(OH)_{2(x1+x2)+4}(CO_3)pH_2O \qquad (8)$$

(wherein, x1 and x2 each represent a number that satisfies the conditions represented by the following equations; and p represents 0 or a positive number: $0 \leq x2/x1 < 10$, $2 \leq (x1+x2) \leq 20$)

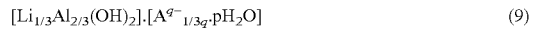

$$[Li_{1/3}Al_{2/3}(OH)_2] \cdot [A^{q-}{}_{1/3q} \cdot pH_2O] \qquad (9)$$

(wherein, $A^{q-}$ represents an anion having a valence of q; and p represents 0 or a positive number)

Further, the carbonate anion in the above-described hydrotalcites may be partially substituted with other anion.

In these hydrotalcites, the crystal water may be dehydrated, and the hydrotalcites may be coated with, for example, a higher fatty acid such as stearic acid, a higher fatty acid metal salt such as alkali metal oleate, a metal organic sulfonate such as alkali metal dodecylbenzenesulfonate, a higher fatty acid amide, a higher fatty acid ester, or a wax.

The hydrotalcite may be a naturally-occurring or synthetic hydrotalcite. Examples of a method of synthesizing such a compound include known methods that are described in Japanese Patent Publication (Kokoku) No. S46-2280, Japanese Patent Publication (Kokoku) No. S50-30039, Japanese Patent Publication (Kokoku) No. S51-29129, Japanese Patent Publication (Kokoku) No. H3-36839, Japanese Unexamined Patent Application Publication No. S61-174270, Japanese Unexamined Patent Application Publication No. H5-179052 and the like. Further, the above-exemplified hydrotalcites can be used without any restriction on the crystal structure, crystal particle and the like.

When any of the above-described hydrotalcites is incorporated, the amount thereof is preferably 0.001 to 5 parts by mass, more preferably 0.05 to 3 parts by mass, with respect to 100 parts by mass of the thermoplastic resin.

As the above-described pigment, a commercially available pigment can be used, and examples thereof include PIGMENT RED 1, 2, 3, 9, 10, 17, 22, 23, 31, 38, 41, 48, 49, 88, 90, 97, 112, 119, 122, 123, 144, 149, 166, 168, 169, 170, 171, 177, 179, 180, 184, 185, 192, 200, 202, 209, 215, 216, 217, 220, 223, 224, 226, 227, 228, 240 and 254; PIGMENT ORANGE 13, 31, 34, 36, 38, 43, 46, 48, 49, 51, 52, 55, 59, 60, 61, 62, 64, 65 and 71, PIGMENT YELLOW 1, 3, 12, 13, 14, 16, 17, 20, 24, 55, 60, 73, 81, 83, 86, 93, 95, 97, 98, 100, 109, 110, 113, 114, 117, 120, 125, 126, 127, 129, 137, 138, 139, 147, 148, 150, 151, 152, 153, 154, 166, 168, 175, 180 and 185; PIGMENT GREEN 7, 10 and 36; PIGMENT BLUE 15, 15:1, 15:2, 15:3, 15:4, 15:5, 15:6, 22, 24, 56, 60, 61, 62 and 64; and PIGMENT VIOLET 1, 19, 23, 27, 29, 30, 32, 37, 40 and 50.

Examples of the above-described dye include azo dyes, anthraquinone dyes, indigoid dyes, triarylmethane dyes, xanthene dyes, alizarin dyes, acridine dyes, stilbene dyes, thiazole dyes, naphthol dyes, quinoline dyes, nitro dyes, indamine dyes, oxazine dyes, phthalocyanine dyes and cyanine dyes, and a plurality of these dyes may be used in combination.

The method of producing the resin composition of the present invention is not particularly restricted, and any commonly used method can be employed as long as the polymer compound (E), the aromatic metal phosphates (H) represented by the Formula (3) or (4) and, as required, the alkali metal salt (G) and other arbitrary component(s) are incorporated into the thermoplastic resin. For example, such components can be mixed and kneaded into the thermoplastic resin by roll kneading or bumper kneading, or using an extruder, a kneader or the like.

The polymer compound (E) may be directly added; however, as required, the polymer compound (E) may be impregnated into a carrier before the addition. In order to impregnate the polymer compound (E) into a carrier, the polymer compound (E) and the carrier can be directly heat-mixed, or a method in which the polymer compound (E) is diluted with an organic solvent before being impregnated into the carrier and the solvent is subsequently removed can be employed as required.

As the carrier, one which is known as a filler or bulking agent of a thermoplastic resin, or a flame retardant or light stabilizer that is solid at normal temperature can be employed, and examples of such a carrier include calcium silicate powder, silica powder, talc powder, alumina powder, titanium oxide powder, and these carriers having chemically modified surface, as well as the below-described flame retardants and antioxidants that are solid. Thereamong, those carriers having chemically modified surface are preferred, and silica powder having a chemically modified surface is more preferred. These carriers have an average particle size of preferably 0.1 to 100 μm, more preferably 0.5 to 50 μm.

As a method of incorporating the polymer compound (E) into a thermoplastic resin component, the block polymer (C), the polymer compound (E) and the aromatic metal phosphates (H) represented by the Formula (3) or (4) may be blended together or separately.

Further, the polymer compound (E) may be synthesized while kneading the block polymer (C) and the epoxy compound (D) having epoxy groups into the resin component and, in this process, the alkali metal salt (G) may also be kneaded at the same time. Alternatively, the polymer compound (E) may be incorporated using a method of obtaining a molded article by mixing the polymer compound (E), the alkali metal salt (G) and the resin component at the time of molding such as injection molding, or a masterbatch of the aromatic metal phosphates (H) represented by the Formula (3) or (4) and/or the alkali metal salt (G) and the thermoplastic resin, which has been produced in advance, may be incorporated.

Moreover, the polymer compound (E) and the alkali metal salt (G) may be mixed in advance and then incorporated into the thermoplastic resin, or the polymer compound (E) synthesized with an addition of the alkali metal salt (G) during reaction may be incorporated into the thermoplastic resin.

Next, the molded article of the present invention will be described.

The molded article of the present invention is obtained by molding the thermoplastic resin composition of the present invention. By molding the resin composition of the present invention, an antistatic resin molded article can be obtained. The molding method is not particularly restricted, and examples thereof include extrusion processing, calender processing, injection molding, rolling, compression molding, blow molding, and rotational molding. Molded articles of various shapes, such as resin plates, sheets, films, bottles, fibers and special shape articles, can be produced by these methods.

Generally, incorporation of an antistatic agent often causes reduction in the physical properties; however, the molded article of the present invention not only exhibits excellent antistatic performance with excellent persistence but also shows limited reduction in the physical properties. Further, the surface of the molded article of the present invention has wiping resistance.

The thermoplastic resin composition of the present invention and molded articles thereof can be used in a wide range of industrial fields, including the fields of electricity/electronics/communication, agriculture/forestry/fisheries, mining, construction, foods, fibers, clothings, health care, coal, petroleum, rubbers, leathers, automobiles, precision instruments, wood materials, building materials, civil engineering, furnitures, printing and musical instruments.

More specific examples of applications where the thermoplastic resin composition of the present invention and molded articles thereof can be used include office work automation equipments, such as printers, personal computers, word processors, keyboards, PDA (Personal Digital Assistant) devices, phones, copy machines, facsimiles, ECRs (electronic cash registers), electronic calculators, electronic organizers, cards, holders and stationeries; household electric appliances, such as laundry machines, refrigerators, vacuum cleaners, microwave ovens, lighting equipments, game machines, irons and kotatsu; audio and visual devices, such as televisions, video tape recorders, video cameras, radio-cassette players, tape recorders, mini discs, CD players, speakers and liquid crystal displays; electric/electronic components and communication devices, such as connectors, relays, capacitors, switches, printed circuit boards, coil bobbins, semiconductor sealing materials, LED sealing materials, electric wires, cables, transformers, deflection yokes, distribution boards and clocks; automobile interior and exterior materials; platemaking films; adhesive films; bottles; food containers; food packaging films; pharmaceutical and medical wrapping films; product packaging films; agricultural films; agricultural sheets; and greenhouse films.

Moreover, the thermoplastic resin composition of the present invention and molded articles thereof can also be used in other various applications, including materials of cars, vehicles, ships, airplanes, buildings and houses as well as construction and civil engineering materials, such as seats (e.g., stuffing and cover materials), belts, ceiling covers, convertible tops, armrests, door trims, rear package trays, carpets, mats, sun visors, wheel covers, mattress covers, air-bags, insulating materials, straps, strap belts, wire coating materials, electric insulating materials, paints, coating materials, veneer materials, floor materials, baffle walls, carpets, wallpapers, wall decorating materials, exterior materials, interior materials, roof materials, deck materials, wall materials, pillar materials, floor boards, fence materials, framing and moulding materials, window and door-shaping materials, shingle boards, sidings, terraces, balconies, soundproof boards, heat insulating boards and window materials; and household articles and sporting goods, such as clothing materials, curtains, sheets, non-woven fabrics, plywood boards, synthetic fiber boards, rugs, doormats, leisure sheets, buckets, hoses, containers, eye glasses, bags, casings, goggles, ski boards, rackets, tents and musical instruments.

[Antistatic Thermoplastic Resin Composition According to Second Embodiment of the Present Invention]

The present invention will now be further described in detail.

First, the antistatic thermoplastic resin composition of the present invention will be described. The resin composition of the present invention comprises, with respect to 100 parts by mass of a thermoplastic resin: 3 to 60 parts by mass of at least one polymer compound (E); and 0.001 to 10 parts by mass of at least one compound (F) represented by the following Formula (2). In the resin composition of the present invention, the polymer compound (E) has a structure in which a diol, an aliphatic dicarboxylic acid, an aromatic dicarboxylic acid, a compound (B) which comprises at least one group represented by the following Formula (1) and has hydroxyl groups at both ends, and an epoxy compound (D) having two or more epoxy groups are bound via ester bonds:

$$—CH_2—CH_2—O— \quad (1)$$

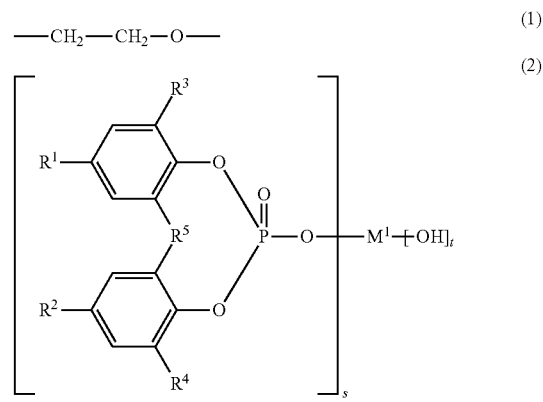

(2)

(wherein, $R^1$ to $R^4$ each independently represent a hydrogen atom or an alkyl group having 1 to 9 carbon atoms; $R^5$ represents an alkylidene group having 1 to 4 carbon atoms; $M^1$ represents an alkali metal atom, an alkaline earth metal atom, a beryllium atom, a magnesium atom or an aluminum atom; when $M^1$ is an alkali metal atom, s is 1 and t is 0; when $M^1$ is an alkaline earth metal atom, a beryllium atom or a magnesium atom, s is 2 and t is 0; and when $M^1$ is an aluminum atom, s is 1 or 2 and t is (3−s)).

The thermoplastic resin used in the present invention will now be described.

Examples of thermoplastic resins that can be used in the resin composition of the present invention include the same ones as those exemplified above for the first embodiment.

In the resin composition of the present invention, these thermoplastic resins may be used individually, or two or more thereof may be used in combination. Further, these thermoplastic resins may be alloyed as well. These thermoplastic resins can be used regardless of molecular weight, polymerization degree, density, softening point, ratio of solvent-insoluble component(s), degree of stereoregularity, presence or absence of catalyst residue, type and blend ratio of each material monomer, type of polymerization catalyst (e.g., a Ziegler catalyst or a metallocene catalyst).

Next, the polymer compound (E) used in the present invention will be described. The polymer compound (E) is incorporated for the purpose of imparting antistaticity to the resin composition of the present invention.

As described above, the polymer compound (E) used in the present invention has a structure in which a diol, an aliphatic dicarboxylic acid, an aromatic dicarboxylic acid, a compound (B) which comprises at least one group represented by the following Formula (1) and has hydroxyl groups at both ends, and an epoxy compound (D) having two or more epoxy groups are bound via ester bonds:

(1)

The polymer compound (E) can be obtained by allowing a diol, an aliphatic dicarboxylic acid, an aromatic dicarboxylic acid, a compound (B) which comprises at least one group represented by the Formula (1) and has hydroxyl groups at both ends, and an epoxy compound (D) having two or more epoxy groups to undergo an esterification reaction.

First, the diol used in the present invention will be described.

Examples of the diol used in the present invention include aliphatic diols and aromatic group-containing diols. Two or more of these diols may be used as a mixture. Examples of aliphatic diols that can be used include the same ones as those exemplified above for the first embodiment.

The aliphatic diols are preferably hydrophobic; therefore, among aliphatic diols, hydrophilic polyethylene glycols are not preferred. This, however, does not apply to those cases where a hydrophilic polyethylene glycol is used in combination with other diol.

Examples of aromatic group-containing diols that can be used include the same ones as those exemplified above for the first embodiment.

Next, the aliphatic dicarboxylic acid used in the present invention will be described.

The aliphatic dicarboxylic acid used in the present invention may be a derivative (such as an acid anhydride, an alkyl ester, an alkali metal salt or an acid halide) of an aliphatic dicarboxylic acid. Further, two or more aliphatic dicarboxylic acids and derivatives thereof may be used as a mixture.

Examples of aliphatic dicarboxylic acids that can be used include the same ones as those exemplified above for the first embodiment.

Next, the aromatic dicarboxylic acid used in the present invention will be described.

The aromatic dicarboxylic acid used in the present invention may be a derivative (such as an acid anhydride, an alkyl ester, an alkali metal salt or an acid halide) of an aromatic dicarboxylic acid. Further, two or more aromatic dicarboxylic acids and derivatives thereof may be used as a mixture.

Examples of aromatic dicarboxylic acids that can be used include the same ones as those exemplified above for the first embodiment.

Next, the compound (B) used in the present invention, which comprises at least one group represented by the Formula (1) and has hydroxyl groups at both ends, will be described.

The compound (B) which comprises at least one group represented by the Formula (1) and has hydroxyl groups at both ends is preferably a hydrophilic compound, more preferably a polyether having the group represented by the Formula (1), particularly preferably a polyethylene glycol represented by the following Formula (6):

(6)

In the Formula (6), m represents a number of 5 to 250. From the standpoints of the heat resistance and compatibility, m is preferably 20 to 150.

As the compound (B), the same compounds as those exemplified above for the first embodiment can be used.

Next, the epoxy compound (D) used in the present invention, which has two or more epoxy groups, will be described. As the epoxy compound (D) in the present invention, the same compounds as those exemplified above for the first embodiment can be used.

From the standpoint of the persistence of antistatic performance, it is preferred that the polymer compound (E) has a structure in which a polyester (A), which is constituted by a diol, an aliphatic dicarboxylic acid and an aromatic dicarboxylic acid, the compound (B) and the epoxy compound (D) are bound via ester bonds.

Further, from the standpoint of the persistence of antistatic performance, it is also preferred that the polymer compound (E) has a structure in which a block polymer (C) having carboxyl groups at both ends and the epoxy compound (D) are bound via an ester bond, the block polymer (C) comprising a block constituted by the polyester (A) constituted by a diol, an aliphatic dicarboxylic acid and an aromatic dicarboxylic acid and a block constituted by the compound (B), which blocks are repeatedly and alternately bound via ester bonds.

The polyester (A) according to the present invention may be any polyester as long as it is composed of a diol, an aliphatic dicarboxylic acid and an aromatic dicarboxylic acid, and it is preferred that the polyester (A) has a structure in which a residue obtained by removing a hydroxyl group from the diol and a residue obtained by removing a carboxyl group from the aliphatic dicarboxylic acid are bound via an ester bond and the residue obtained by removing a hydroxyl group from the diol and a residue obtained by removing a carboxyl group from the aromatic dicarboxylic acid are bound via an ester bond.

It is also preferred that the polyester (A) has a structure comprising carboxyl groups at both ends. Further, the polymerization degree of the polyester (A) is preferably in a range of 2 to 50.

The polyester (A) having carboxyl groups at both ends can be obtained by, for example, allowing the above-described aliphatic dicarboxylic acid and the above-described aromatic dicarboxylic acid to undergo a polycondensation reaction with the above-described diol.

The aliphatic dicarboxylic acid may be a derivative (such as an acid anhydride, an alkyl ester, an alkali metal salt or an acid halide) of an aliphatic dicarboxylic acid and, in cases where the polyester (A) is obtained using such a derivative, both ends of the polyester (A) can eventually be treated to be carboxyl groups, and the polyester (A) in this state may be directly subjected to the subsequent reaction for obtaining the block polymer (C) having a structure comprising carboxyl groups at both ends. Further, two or more aliphatic dicarboxylic acids and derivatives thereof may be used in combination.

The aromatic dicarboxylic acid may be a derivative (such as an acid anhydride, an alkyl ester, an alkali metal salt or an acid halide) of an aromatic dicarboxylic acid, and in cases where the polyester is obtained using such a derivative, both ends of the polyester can eventually be treated to be carboxyl groups, and the polyester in this state may be directly subjected to the subsequent reaction for obtaining the block polymer (C) having a structure comprising carboxyl groups at both ends. Further, two or more aromatic dicarboxylic acids and derivatives thereof may be used in combination.

In the polyester (A), the molar ratio of a residue excluding the carboxyl groups of the aliphatic dicarboxylic acid and the residue excluding the carboxyl groups of the aromatic dicarboxylic acid is preferably 90:10 to 99.9:0.1, more preferably 93:7 to 99.9:0.1.

The polyester (A) having carboxyl groups at both ends can be obtained by, for example, allowing the above-described aliphatic dicarboxylic acid or derivative thereof and the above-described aromatic dicarboxylic acid or derivative thereof to undergo a polycondensation reaction with the above-described diol.

As for the reaction ratio of the aliphatic dicarboxylic acid or derivative thereof and the aromatic dicarboxylic acid or derivative thereof with respect to the diol, it is preferred that the aliphatic dicarboxylic acid or derivative thereof and the aromatic dicarboxylic acid or derivative thereof are used in an excess amount, particularly in an excess of 1 mole in terms of molar ratio with respect to the diol, such that the resulting polyester has carboxyl groups at both ends.

In the polycondensation reaction, the compounding ratio of the aliphatic dicarboxylic acid or derivative thereof and the aromatic dicarboxylic acid or derivative thereof is, in terms of molar ratio, preferably 90:10 to 99.9:0.1, more preferably 93:7 to 99.9:0.1.

Depending on the compounding ratio and the reaction conditions, a polyester consisting of only the diol and the aliphatic dicarboxylic acid and a polyester consisting of only the diol and the aromatic dicarboxylic acid may be generated; however, in the present invention, the polyester (A) may contain such polyesters, or the block polymer (C) may be obtained by directly allowing such polyesters to react with the component (B).

In the polycondensation reaction, a catalyst which promotes esterification reaction may be used and, as such a catalyst, a conventionally known catalyst such as dibutyltin oxide, tetraalkyl titanate, zirconium acetate or zinc acetate can be employed.

In cases where a derivative such as a carboxylic acid ester, metal carboxylate or carboxylic acid halide is used in place of the dicarboxylic acid of the aliphatic dicarboxylic acid and the aromatic dicarboxylic acid, after the derivative and the diol are allowed to react with each other, both ends of the resultant may be treated to be dicarboxylic acids, or the resultant may be directly subjected to the subsequent reaction for obtaining the block polymer (C) having a structure comprising carboxyl groups at both ends.

A preferred polyester (A), which is composed of a diol, an aliphatic dicarboxylic acid and an aromatic dicarboxylic acid and has carboxyl groups at both ends, may be any polyester as long as it reacts with the component (B) to form an ester bond and thereby constitutes the structure of the block polymer (C), and the carboxyl groups at both ends may be protected or modified, or may be in a precursor form. Further, in order to inhibit oxidation of the product during the reaction, an antioxidant such as a phenolic antioxidant may also be added to the reaction system.

The compound (B) having hydroxyl groups at both ends may be any compound as long as it reacts with the component (A) to form an ester bond and thereby constitutes the structure of the block polymer (C), and the hydroxyl groups at both ends may be protected or modified, or may be in a precursor form.

The block polymer (C) according to the present invention, which has a structure comprising carboxyl groups at both ends, contains a block constituted by the polyester (A) and a block constituted by the compound (B) and has a structure in which these blocks are repeatedly and alternately bound via ester bonds formed by carboxyl groups and hydroxyl groups. One example of the block polymer (C) is a block polymer having a structure represented by the following Formula (7):

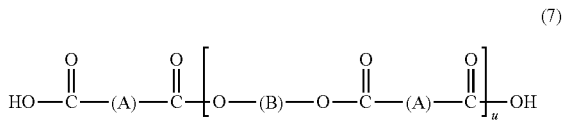

In the Formula (7), (A) represents a block constituted by the polyester (A) having carboxyl groups at both ends; (B) represents a block constituted by the compound (B) having hydroxyl groups at both ends; and u represents the number of repeating units, which is preferably 1 to 10, more preferably 1 to 7, most preferably 1 to 5.

In the block polymer (C), the block constituted by the polyester (A) may be partially replaced with a block constituted by a polyester consisting of only a diol and an aliphatic dicarboxylic acid or a block constituted by a polyester consisting of only a diol and an aromatic dicarboxylic acid.

The block polymer (C) having a structure comprising carboxyl groups at both ends can be obtained by allowing the polyester (A) having carboxyl groups at both ends and the compound (B) having hydroxyl groups at both ends to undergo a polycondensation reaction; however, as long as the block polymer (C) has a structure that is equivalent to the one in which the polyester (A) and the compound (B) are repeatedly and alternately bound via ester bonds formed by carboxyl groups and hydroxyl groups, it is not necessarily required that the block polymer (C) be synthesized from the polyester (A) and the compound (B).

As for the reaction ratio between the polyester (A) and the compound (B), by adjusting the amount of the polyester (A) to be (X+1) mol with respect to X mol of the compound (B), the block polymer (C) having carboxyl groups at both ends can be preferably obtained.

As for the reaction, after the completion of the synthesis reaction of the polyester (A), without the thus synthesized polyester (A) being isolated, the compound (B) may be added to the reaction system and allowed to react with the polyester (A) as is.

In the polycondensation reaction, a catalyst which promotes esterification reaction may be used and, as such a catalyst, a conventionally known catalyst such as dibutyltin oxide, tetraalkyl titanate, zirconium acetate or zinc acetate can be employed. Further, in order to inhibit oxidation of the product during the reaction, an antioxidant such as a phenolic antioxidant may also be added to the reaction system.

Further, the polyester (A) may contain a polyester consisting of only a diol and an aliphatic dicarboxylic acid and/or a polyester consisting of only a diol and an aromatic dicarboxylic acid, and these polyesters may be directly allowed to react with the compound (B) to obtain the block polymer (C).

In addition to the block constituted by the polyester (A) and the block constituted by the compound (B), the block polymer (C) may also contain, in its structure, a block constituted by a polyester consisting of only a diol and an aliphatic dicarboxylic acid and/or a block constituted by a polyester consisting of only a diol and an aromatic dicarboxylic acid.

It is preferred that the polymer compound (E) according to the present invention has a structure in which the block polymer (C) having a structure comprising carboxyl groups at both ends and the epoxy compound (D) having two or more epoxy groups are bound via an ester bond formed by a terminal carboxyl group of the block polymer (C) and an epoxy group of the epoxy compound (D). The polymer compound (E) may further comprise an ester bond formed by a carboxyl group of the polyester (A) and an epoxy group of the epoxy compound (D).

In order to obtain the polymer compound (E), the carboxyl groups of the block polymer (C) and the epoxy groups of the epoxy compound (D) can be allowed to react with each other. The number of the epoxy groups of the epoxy compound is preferably 0.5 to 5 equivalents, more preferably 0.5 to 1.5 equivalents, with respect to the number of the carboxyl groups of the block polymer (C) to be reacted. Further, the reaction can be performed in a variety of solvents, or it may be performed in a molten state.

The amount of the epoxy compound (D) having two or more epoxy groups to be used in the reaction is preferably 0.1 to 2.0 equivalents, more preferably 0.2 to 1.5 equivalents, with respect to the number of the carboxyl groups of the block polymer (C) to be reacted.

As for the reaction, after the completion of the synthesis reaction of the block polymer (C), without the thus synthesized block polymer (C) being isolated, the epoxy compound (D) may be added to the reaction system and allowed to react with the block polymer (C) as is. In this case, unreacted carboxyl groups of the polyester (A) used in an excess amount in the synthesis of the block polymer (C) may react with some of the epoxy groups of the epoxy compound (D) to form ester bonds.

It is not necessarily required that a preferred polymer compound (E) of the present invention be synthesized from the block polymer (C) and the epoxy compound (D), as long as the polymer compound (E) has a structure that is equivalent to the one in which the block polymer (C) having a structure comprising carboxyl groups at both ends and the epoxy compound (D) having two or more epoxy groups are bound via an ester bond formed by a carboxyl group of the block polymer (C) and an epoxy group of the epoxy compound (D).

In the polymer compound (E) of the present invention, the block constituted by the polyester (A) has a number-average molecular weight of preferably 800 to 8,000, more preferably 1,000 to 6,000, still more preferably 2,000 to 4,000, in terms of polystyrene. Further, in the polymer compound (E), the block constituted by the compound (B) having hydroxyl groups at both ends has a number-average molecular weight of preferably 400 to 6,000, more preferably 1,000 to 5,000, still more preferably 2,000 to 4,000, in terms of polystyrene. Moreover, in the polymer compound (E), the block constituted by the block polymer (C) having a structure comprising carboxyl groups at both ends has a number-average molecular weight of preferably 5,000 to 25,000, more preferably 7,000 to 17,000, still more preferably 9,000 to 13,000, in terms of polystyrene.

The polymer compound (E) of the present invention may also be obtained by preparing the polyester (A) from a diol, an aliphatic dicarboxylic acid and an aromatic dicarboxylic acid and subsequently allowing the polyester (A) to react with the compound (B) and/or the epoxy compound (D), without isolating the polyester (A).

The amount of the polymer compound (E) to be incorporated is 3 to 60 parts by mass with respect to 100 parts by mass of the thermoplastic resin and, from the standpoints of the persistence of antistatic performance and the organic solvent resistance, it is preferably 5 to 50 parts by mass, more preferably 7 to 40 parts by mass. When the amount of the polymer compound (E) is less than 3 parts by mass, sufficient antistaticity cannot be obtained, whereas when the amount is greater than 60 parts by mass, the mechanical properties of the resin may be adversely affected.

Next, the at least one compound (F) used in the present invention, which is represented by the following Formula (2), will be described. The compound (F) represented by the Formula (2) is incorporated into the resin composition of the present invention as a nucleator.

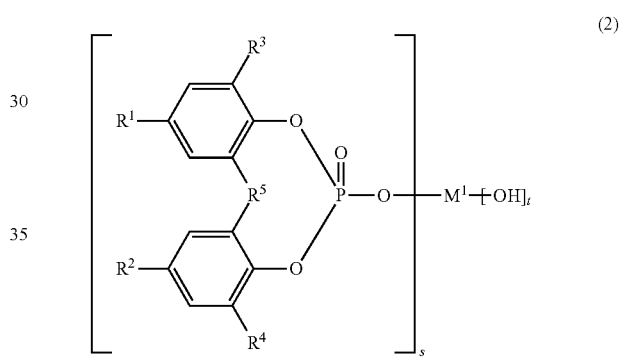

The compound represented by the Formula (2) is a metal salt compound of an aromatic phosphoric acid ester and, in the Formula (2), $R^1$ to $R^4$ each independently represent a hydrogen atom or an alkyl group having 1 to 9 carbon atoms; $R^5$ represents an alkylidene group having 1 to 4 carbon atoms; and $M^1$ represents an alkali metal atom, an alkaline earth metal atom, a beryllium atom, a magnesium atom or an aluminum atom.

Further, when $M^1$ is an alkali metal atom, s is 1 and t is 0; when $M^1$ is an alkaline earth metal atom, a beryllium atom or a magnesium atom, s is 2 and t is 0; and when $M^1$ is an aluminum atom, s is 1 or 2 and t is (3−s).

Examples of the alkyl group having 1 to 9 carbon atoms include a methyl group, an ethyl group, a propyl group, an isopropyl group, a butyl group, a sec-butyl group, a tert-butyl group, an isobutyl group, an amyl group, a tert-amyl group, a hexyl group, a heptyl group, an octyl group, an isooctyl group, a tert-octyl group, a 2-ethylhexyl group, a nonyl group and an isononyl group, and $R^1$ to $R^4$ are preferably tert-butyl groups.

Examples of the alkylidene group having 1 to 4 carbon atoms include a methylene group, an ethylidene group, a propylidene group and a butylidene group.

Examples of the alkali metal include lithium, sodium and potassium, and examples of the alkaline earth metal include calcium and barium.

Particularly, M¹ is preferably an alkali metal atom since an excellent effect as a nucleator can be obtained.

Examples of a method of producing the compound represented by the Formula (2) include a method of allowing a cyclic phosphoric acid having a corresponding structure to react with a metal compound (e.g., a metal hydroxide, a metal oxide, a metal halide, a metal sulfate, a metal nitrate or a metal alkoxide compound) using a reaction agent that is used as required, such as a basic compound; a method of allowing an alkali metal salt of a cyclic phosphoric acid ester having a corresponding structure to undergo a salt exchange reaction with a metal compound (e.g., a metal hydroxide, a metal oxide, a metal halide, a metal sulfate, a metal nitrate or a metal alkoxide compound) using a reaction agent that is used as required; and a method of generating a cyclic phosphoric acid by hydrolysis using cyclic phosphorus oxychloride as a starting substance and subsequently allowing the thus generated cyclic phosphoric acid to react with a metal compound.

Preferred examples of the compound (F) represented by the Formula (2) include aromatic metal phosphates (H) represented by the following Formula (3) or (4):

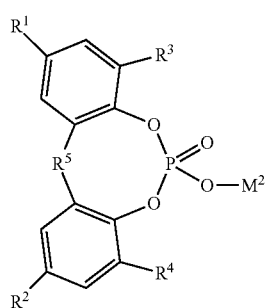

(3)

(wherein, R¹ to R⁴ each independently represent the same as in the Formula (2); R⁵ represents the same as in the Formula (2); and M² represents an alkali metal)

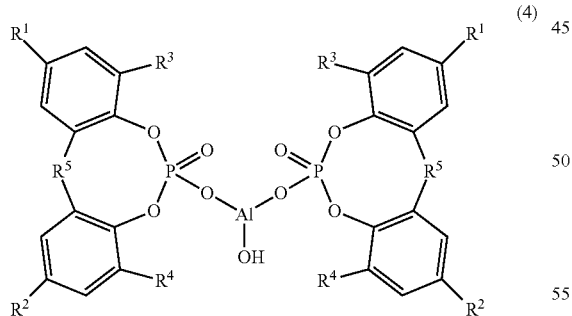

(4)

(wherein, R¹ to R⁵ represent the same as in the Formula (3)).

In the resin composition of the present invention, it is preferred that the aromatic metal phosphates (H) are a mixture of an aromatic sodium phosphate compound represented by the Formula (3) wherein M² is sodium and an aromatic lithium phosphate compound represented by the Formula (3) wherein M² is lithium.

The ratio of the aromatic sodium phosphate compound and the aromatic lithium phosphate compound (aromatic sodium phosphate compound/aromatic lithium phosphate compound) is preferably in a range of 1/4 to 4/1 in terms of mass ratio.

When the ratio is outside the above-described range, the effects of the present invention may not be attained.

Specific examples of the compound represented by the Formula (2) include the following compound Nos. 1 to 18. It is noted here, however, that the present invention is not restricted thereto.

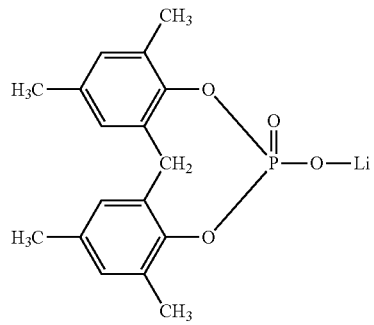

Compound No. 1

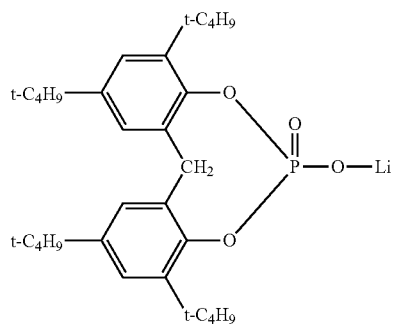

Compound No. 2

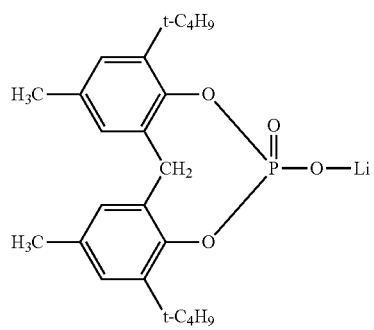

Compound No. 3

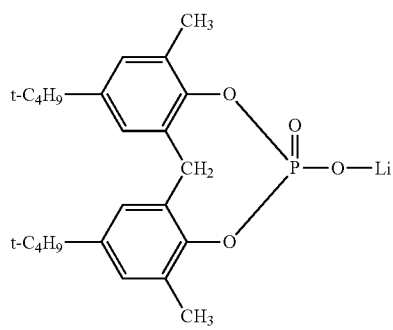

compound No. 4 compound No. 5
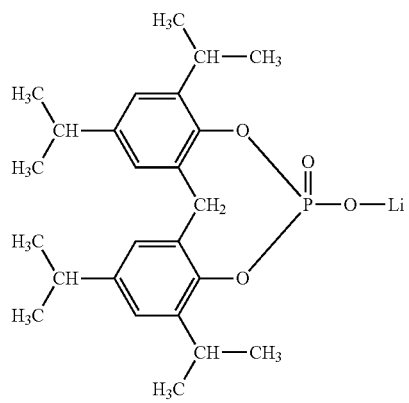
compound No. 6
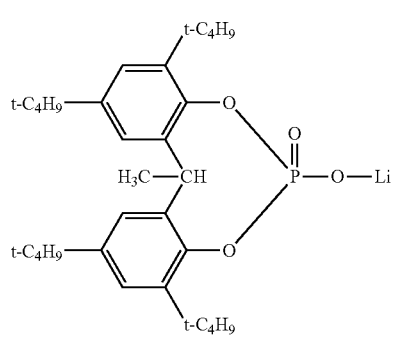
compound No. 7
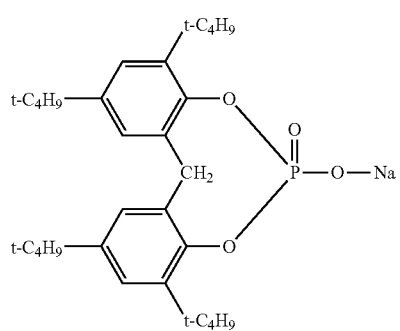
compound No. 8
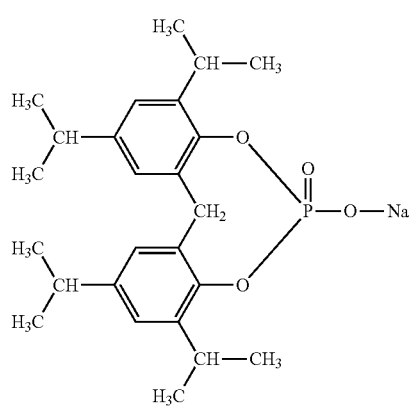
compound No. 9
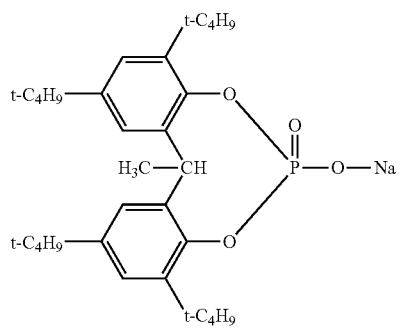
compound No. 10
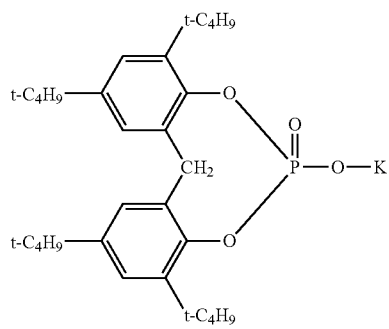
compound No. 11
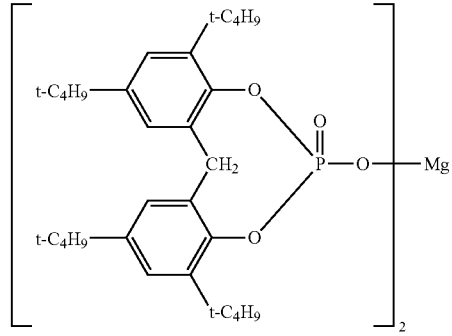
compound No. 12
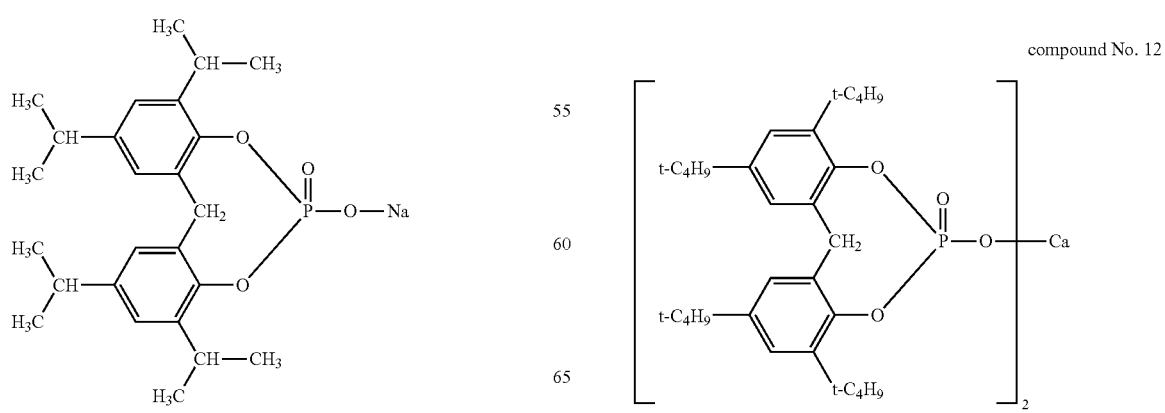

compound No. 13

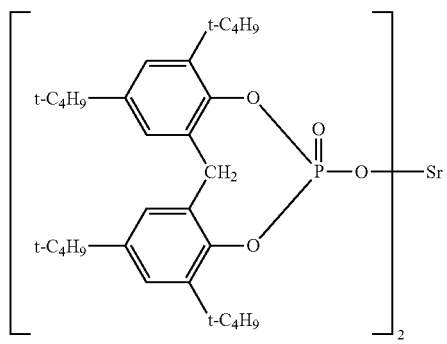

compound No. 14

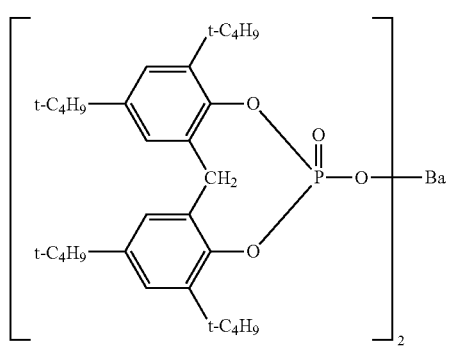

compound No. 15

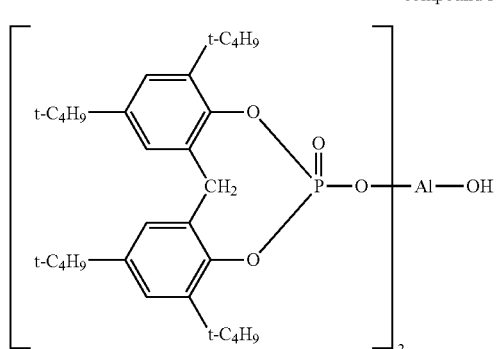

compound No. 16

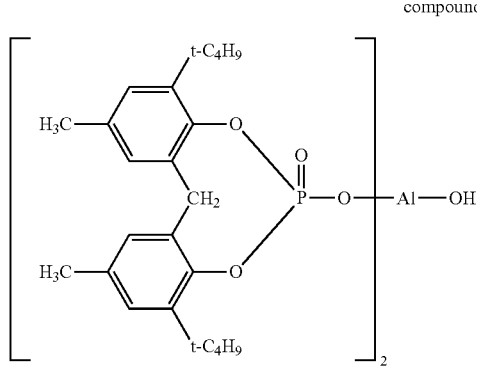

compound No. 17

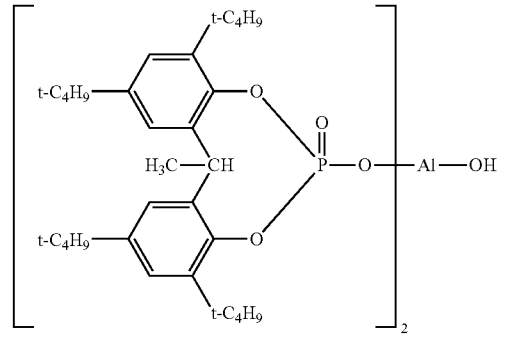

compound No. 18

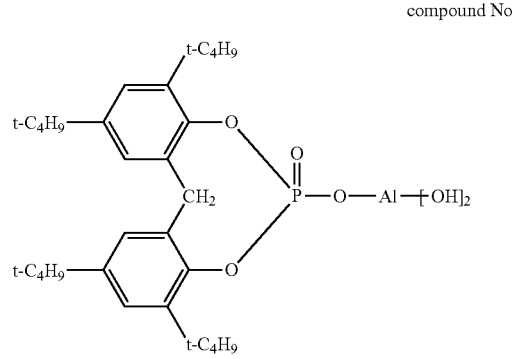

The compound (F) represented by the Formula (2) is incorporated in an amount of 0.001 to 10 parts by mass and, from the standpoint of the crystallization properties, preferably 0.005 to 5.0 parts by mass, more preferably 0.01 to 3.0 parts by mass, with respect to 100 parts by mass of the thermoplastic resin. When the amount is less than 0.001 parts by mass, a sufficient effect as a nucleator may not be attained, whereas when the amount is greater than 10 parts by mass, the physical properties of the resin may be deteriorated. Further, in cases where an aromatic metal phosphate (H) represented the Formula (3) or (4) is used as the compound (F), it is preferred to incorporate two or more selected from such aromatic metal phosphates (H) in an amount of 0.001 to 50 parts by mass, more preferably 0.01 to 10 parts by mass, with respect to 100 parts by mass of the polymer compound (E). When the amount is less than 0.001 parts by mass, the effects of the present invention may not be attained, whereas when the amount is greater than 50 parts by mass, it is difficult to disperse the aromatic metal phosphates into the thermoplastic resin and this may adversely affect the physical properties and outer appearance of the resulting molded article.

In this case, in the present invention, it is preferred to further incorporate 10 to 50 parts by mass of a fatty acid metal salt (I) represented by the following Formula (5) with respect to a total of 100 parts by mass of the two or more selected from aromatic metal phosphates (H):

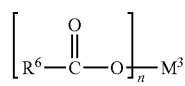

(5)

(wherein, $R^6$ represents an unsubstituted or hydroxy group-substituted aliphatic group having 1 to 40 carbon atoms; $M^3$ represents a metal atom; n is an integer of 1 to 4 and represents the valence of the metal atom $M^3$).

Examples of the aliphatic group having 1 to 40 carbon atoms that is represented by $R^6$ in the Formula (5) include hydrocarbon groups, such as alkyl groups, alkenyl groups and alkyl groups to which two or more unsaturated bonds are introduced, and the aliphatic group is optionally substituted with a hydroxyl group and/or branched.

Specific examples of the fatty acid include saturated fatty acids, such as acetic acid, propionic acid, butyric acid, valeric acid, isovaleric acid, caproic acid, enanthic acid, caprylic acid, pelargonic acid, capric acid, 2-ethylhexanoic acid, undecylic acid, lauric acid tridecylic acid, myristic acid, pentadecylic acid, palmitic acid, margaric acid, stearic acid, nonadecylic acid, arachidic acid, heneicosylic acid, behenic acid, tricosylic acid, lignoceric acid cerotic acid, montanoic acid and melissic acid; linear unsaturated fatty acids, such as 4-decenoic acid, 4-dodecenoic acid, palmitoleic acid, α-linolenic acid, linoleic acid, γ-linolenic acid, stearidonic acid, petroselinic acid, oleic acid, elaidic acid, vaccenic acid, eicosapentaenoic acid, docosapentaenoic acid and docosahexaenoic acid; and aromatic fatty acids such as trimesic acid.

In the present invention, aliphatic groups having 7 to 21 carbon atoms are preferred, and saturated fatty acids such as myristic acid, stearic acid and 12-hydroxystearic acid are particularly preferred.

Examples of the metal atom that is represented by $M^3$ in the Formula (5) include alkali metals, magnesium, calcium, strontium, barium, titanium, manganese, iron, zinc, silicon, zirconium, yttrium, barium, and hafnium. Thereamong, alkali metals such as sodium, lithium and potassium can be particularly preferably used.

In the present invention, from the standpoints of performance and relative availability, the fatty acid metal salt (I) is, for example, preferably lithium stearate, sodium stearate, magnesium stearate, zinc stearate, aluminum stearate, lithium myristate, magnesium behenate or lithium 12-hydroxystearate, more preferably lithium myristate, lithium stearate or lithium 12-hydroxystearate.

The above-exemplified fatty acid metal salts can be produced by a synthesis method in which a carboxylic acid compound and a metal hydroxide are allowed to react with each other and the resultant is subsequently washed with water, dehydrated and dried (double decomposition method), or a synthesis method in which materials are allowed to directly react with each other without the use of water (direct method).

The amount of the fatty acid metal salt (I) to be incorporated is preferably in a range of 10 to 50 parts by mass with respect to a total of 100 parts by mass of the aromatic metal phosphates (H) represented by the Formula (3) or (4). When the amount is less than 10 parts by mass, the effects of the fatty acid metal salt (I) as a dispersant may not be obtained, whereas when the amount is greater than 50 parts by mass, the fatty acid metal salt (I) may adversely affect the nucleating effect of the aromatic metal phosphates.

In the resin composition of the present invention, from the standpoints of the persistence of antistaticity and the crystallization properties, it is also preferred to incorporate at least one alkali metal salt (G).

Examples of the alkali metal salt (G) include salts of organic acids and inorganic acids.

Specific examples of alkali metals and alkali metal salts that can be used include the same ones as those exemplified above for the first embodiment.

From the standpoints of the persistence of antistatic performance and the crystallization properties, the alkali metal salt (G) can be incorporated in an amount of 0.01 to 5.0 parts by mass, preferably 0.3 to 2.0 parts by mass, more preferably 0.4 to 1.0 part by mass, with respect to 100 parts by mass of the thermoplastic resin. When the amount of the alkali metal salt is less than 0.01 parts by mass, satisfactory antistaticity may not be attained, whereas when the amount is greater than 5.0 parts by mass, the alkali metal salt may affect the physical properties of the resin.

In the resin composition of the present invention, a Group II element salt may further be incorporated in such a range that does not impair the effects of the present invention.

Examples of the Group II element salt include those of organic acids and inorganic acids, and examples of the Group II element, organic acids and inorganic acids include the same ones as those exemplified above for the first embodiment.

In the resin composition of the present invention, a surfactant may also be incorporated in such a range that does not impair the effects of the present invention. As the surfactant, a nonionic, anionic, cationic or amphoteric surfactant can be used.

Examples of the nonionic surfactant, anionic surfactant, cationic surfactant and amphoteric surfactant include the same ones as those exemplified above for the first embodiment, and such surfactants may be used individually, or two or more thereof may be used in combination.

When a surfactant is incorporated, the amount thereof is preferably 0.1 to 5 parts by mass, more preferably 0.5 to 2 parts by mass, with respect to 100 parts by mass of the thermoplastic resin.

Further, in the resin composition of the present invention, a polymer-type antistatic agent may also be incorporated. As the polymer-type antistatic agent, the same ones as those exemplified above for the first embodiment can be used.

When a polymer-type antistatic agent is incorporated, the amount thereof is preferably 0.1 to 10 parts by mass, more preferably 0.5 to 5 parts by mass, with respect to 100 parts by mass of the thermoplastic resin.

Still further, in the resin composition of the present invention, an ionic liquid may also be incorporated in such a range that does not impair the effects of the present invention. As the ionic liquid, for example, the same ones as those exemplified above for the first embodiment can be used.

When an ionic liquid is incorporated, the amount thereof is preferably 0.01 to 5 parts by mass, more preferably 0.1 to 3 parts by mass, with respect to 100 parts by mass of the thermoplastic resin.

Yet still further, in the resin composition of the present invention, a compatibilizer may also be incorporated in such a range that does not impair the effects of the present invention. By incorporating a compatibilizer, the compatibility of the antistatic component with other components and the resin component can be improved. As the compatibilizer, the same ones as those exemplified above for the first embodiment can be used.

When a compatibilizer is incorporated, the amount thereof is preferably 0.01 to 5 parts by mass, more preferably 0.1 to 3 parts by mass, with respect to 100 parts by mass of the thermoplastic resin.

Moreover, in the resin composition of the present invention, as required, a variety of additives such as a phenolic antioxidant, a phosphorus-based antioxidant, a thioether-based antioxidant, an ultraviolet absorber and a hindered amine-based light stabilizer may also be added in such a range that does not impair the effects of the present invention. By this, the resin composition of the present invention can be stabilized.

Examples of the phenolic antioxidant include 2,6-di-tert-butyl-p-cresol, 2,6-diphenyl-4-octadecyloxyphenol, distearyl(3,5-di-tert-butyl-4-hydroxybenzyl)phosphonate, 1,6-hexamethylene-bis[(3,5-di-tert-butyl-4-hydroxyphenyl) propionic acid amide], 4,4'-thiobis(6-tert-butyl-m-cresol), 2,2'-methylene-bis(4-methyl-6-tert-butyl phenol), 2,2'-methylene-bis(4-ethyl-6-tert-butylphenol), 4,4'-butylidene-bis(6-tert-butyl-m-cresol), 2,2'-ethylidene-bis(4,6-di-tert-butylphenol), 2,2'-ethylidene-bis(4-sec-butyl-6-tert-butylphenol), 1,1,3-tris(2-methyl-4-hydroxy-5-tert-butylphenyl) butane, 1,3,5-tris(2,6-dimethyl-3-hydroxy-4-tert-butylbenzyl)isocyanurate, 1,3,5-tris(3,5-di-tert-butyl-4-hydroxybenzyl)isocyanurate, 1,3,5-tris(3,5-di-tert-butyl-4-hydroxybenzyl)-2,4,6-trimethyl benzene, 2-tert-butyl-4-methyl-6-(2-acryloyloxy-3-tert-butyl-5-methylbenzyl)phenol, stearyl (3,5-di-tert-butyl-4-hydroxyphenyl)propionate, tetrakis[3-(3,5-di-tert-butyl-4-hydroxyphenyl)propionic acid methyl] methane, thiodiethylene glycol-bis[(3,5-di-tert-butyl-4-hydroxyphenyl)propionate], 1,6-hexamethylene-bis[(3,5-di-tert-butyl-4-hydroxyphenyl)propionate], bis[3,3-bis(4-hydroxy-3-tert-butylphenyl)butyric acid]glycol ester, bis[2-tert-butyl-4-methyl-6-(2-hydroxy-3-tert-butyl-5-methylbenzyl) phenyl]terephthalate, 1,3,5-tris[(3,5-di-tert-butyl-4-hydroxyphenyl)propionyloxyethyl]isocyanurate, 3,9-bis[1,1-dimethyl-2-{(3-tert-butyl-4-hydroxy-5-methylphenyl) propionyloxy}ethyl]-2,4,8,10-tetraoxaspiro[5,5]undecane, and triethylene glycol-bis[(3-tert-butyl-4-hydroxy-5-methylphenyl)propionate]. These phenolic antioxidants are added in an amount of preferably 0.001 to 10 parts by mass, more preferably 0.05 to 5 parts by mass, with respect to 100 parts by mass of the thermoplastic resin.

Examples of the phosphorus-based antioxidant include trisnonylphenyl phosphite, tris[2-tert-butyl-4-(3-tert-butyl-4-hydroxy-5-methylphenylthio)-5-methylphenyl]phosphite, tridecyl phosphite, octyldiphenyl phosphite, di(decyl)monophenyl phosphite, di(tridecyl)pentaerythritol diphosphite, di(nonylphenyl)pentaerythritol diphosphite, bis(2,4-di-tert-butylphenyl)pentaerythritol diphosphite, bis(2,6-di-tert-butyl-4-methylphenyl)pentaerythritol diphosphite, bis(2,4,6-tri-tert-butylphenyl)pentaerythritol diphosphite, bis(2,4-dicumylphenyl)pentaerythritol diphosphite, tetra(tridecyl) isopropylidenediphenol diphosphite, tetra(tridecyl)-4,4'-n-butylidene-bis(2-tert-butyl-5-methylphenol)diphosphite, hexa(tridecyl)-1,1,3-tris(2-methyl-4-hydroxy-5-tert-butylphenyl)butane triphosphite, tetrakis(2,4-di-tert-butylphenyl) biphenylene diphosphonite, 9,10-dihydro-9-oxa-10-phosphaphenanthrene-10-oxide, 2,2'-methylene-bis(4,6-tert-butylphenyl)-2-ethylhexyl phosphite, 2,2'-methylene-bis(4,6-tert-butylphenyl)-octadecyl phosphite, 2,2'-ethylidene-bis (4,6-di-tert-butylphenyl)fluorophosphite, tris(2-[(2,4,8,10-tetrakis-tert-butyldibenzo[d,f][1,3,2]dioxaphosphepin-6-yl) oxy]ethyl)amine, and phosphite of 2-ethyl-2-butylpropylene glycol and 2,4,6-tri-tert-butylphenol. These phosphorus-based antioxidants are added in an amount of preferably 0.001 to 10 parts by mass, more preferably 0.05 to 5 parts by mass, with respect to 100 parts by mass of the thermoplastic resin.

Examples of the thioether-based antioxidant include dialkyl thiodipropionates, such as dilauryl thiodipropionate, dimyristyl thiodipropionate and distearyl thiodipropionate; and pentaerythritol-tetra(β-alkylthiopropionic acid)esters. These thioether-based antioxidants are added in an amount of preferably 0.001 to 10 parts by mass, more preferably 0.05 to 5 parts by mass, with respect to 100 parts by mass of the thermoplastic resin.

Examples of the ultraviolet absorber include 2-hydroxybenzophenones, such as 2,4-dihydroxybenzophenone, 2-hydroxy-4-methoxybenzophenone, 2-hydroxy-4-octoxybenzophenone and 5,5'-methylene-bis(2-hydroxy-4-methoxybenzophenone); 2-(2'-hydroxyphenyl)benzotriazoles, such as 2-(2'-hydroxy-5'-methylphenyl)benzotriazole, 2-(2'-hydroxy-3',5'-di-tert-butylphenyl)-5-chlorobenzotriazole, 2-(2'-hydroxy-3'-tert-butyl-5'-methylphenyl)-5-chlorobenzotriazole, 2-(2'-hydroxy-5'-tert-octylphenyl)benzotriazole, 2-(2'-hydroxy-3',5'-dicumylphenyl)benzotriazole, 2,2'-methylene-bis(4-tert-octyl-6-(benzotriazolyl)phenol) and 2-(2'-hydroxy-3'-tert-butyl-5'-carboxyphenyl)benzotriazole; benzoates, such as phenyl salicylate, resorcinol monobenzoate, 2,4-di-tert-butylphenyl-3,5-di-tert-butyl-4-hydroxybenzoate, 2,4-di-tert-amylphenyl-3,5-di-tert-butyl-4-hydroxybenzoate and hexadecyl-3,5-di-tert-butyl-4-hydroxybenzoate; substituted oxanilides, such as 2-ethyl-2'-ethoxyoxanilide and 2-ethoxy-4'-dodecyloxanilide; cyanoacrylates, such as ethyl-α-cyano-β,β-diphenyl acrylate and methyl-2-cyano-3-methyl-3-(p-methoxyphenyl)acrylate; and triaryl triazines, such as 2-(2-hydroxy-4-octoxyphenyl)-4,6-bis(2,4-di-tert-butylphenyl)-s-triazine, 2-(2-hydroxy-4-methoxyphenyl)-4,6-diphenyl-s-triazine and 2-(2-hydroxy-4-propoxy-5-methylphenyl)-4,6-bis(2,4-di-tert-butylphenyl)-s-triazine. These ultraviolet absorbers are added in an amount of preferably 0.001 to 30 parts by mass, more preferably 0.05 to 10 parts by mass, with respect to 100 parts by mass of the thermoplastic resin.

Examples of the hindered amine-based light stabilizer include hindered amine compounds, such as 2,2,6,6-tetramethyl-4-piperidyl stearate, 1,2,2,6,6-pentamethyl-4-piperidyl stearate, 2,2,6,6-tetramethyl-4-piperidyl benzoate, bis (2,2,6,6-tetramethyl-4-piperidyl)sebacate, bis(1,2,2,6,6-pentamethyl-4-piperidyl)sebacate, bis(1-oxtoxy-2,2,6,6-tetramethyl-4-piperidyl)sebacate, tetrakis(2,2,6,6-tetramethyl-4-piperidyl)-1,2,3,4-butanetetracarboxylate, tetrakis(1,2,2,6,6-pentamethyl-4-piperidyl)-1,2,3,4-butanetetracarboxylate, bis(2,2,6,6-tetramethyl-4-piperidyl).di(tridecyl)-1,2,3,4-butanetetracarboxylate, bis(1,2,2,6,6-pentamethyl-4-piperidyl) .di(tridecyl)-1,2,3,4-butanetetracarboxylate, bis(1,2,2,4,4-pentamethyl-4-piperidyl)-2-butyl-2-(3,5-di-tert-butyl-4-hydroxybenzyl)malonate 1-(2-hydroxyethyl)-2,2,6,6-tetramethyl-4-piperidinol/diethyl succinate polycondensate, 1,6-bis(2,2,6,6-tetramethyl-4-piperidylamino)hexane/2,4-dichloro-6-morpholino-s-triazine polycondensate, 1,6-bis(2, 2,6,6-tetramethyl-4-piperidyl amino)hexane/2,4-dichloro-6-tert-octylamino-s-triazine polycondensate, 1,5,8,12-tetrakis [2,4-bis(N-butyl-N-(2,2,6,6-tetramethyl-4-piperidyl) amino)-s-triazine-6-yl]-1, 5,8,12-tetraazadodecane, 1,5,8, 12-tetrakis[2,4-bis(N-butyl-N-(1,2,2,6,6-pentamethyl-4-piperidyl)amino)-s-triazine-6-yl]-1,5,8,12-tetraazadodecane, 1,6,11-tris[2,4-bis(N-butyl-N-(2,2,6,6-tetramethyl-4-piperidyl)amino)-s-triazine-6-yl]aminoun decane and 1,6, 11-tris[2,4-bis(N-butyl-N-(1,2,2,6,6-pentamethyl-4-piperidyl)amino)-s-triazine-6-yl]amino undecane. These hindered amine-based light stabilizers are added in an amount of preferably 0.001 to 30 parts by mass, more preferably 0.05 to 10 parts by mass, with respect to 100 parts by mass of the thermoplastic resin.

It is preferred to further add a known neutralizer as required for the purpose of neutralizing residual catalyst contained in the thermoplastic resin. Examples of the neutralizer include fatty acid metal salts, such as calcium stearate, lithium stearate and sodium stearate; and fatty acid amide compounds, such as ethylene-bis(stearamide), ethylene-bis(12-hydroxystearamide) and stearic acid amide, and these neutralizers may be used in the form of a mixture.

Still further, in the resin composition of the present invention, as required, for example, a nucleator other than the compound (F) represented by the Formula (2) (e.g., an aromatic metal carboxylate, an alicyclic metal alkylcarboxylate, aluminum p-tert-butylbenzoate, or a kind of dibenzylidene sorbitol), a metallic soap, a hydrotalcite, a triazine ring-containing compound, a metal hydroxide, a phosphoric acid ester-based flame retardant, a condensed phosphoric acid ester-based flame retardant, a phosphate-based flame retardant, an inorganic phosphorus-based flame retardant, a (poly)phosphate-based flame retardant, a halogen-based flame retardant, a silicon-based flame retardant, an antimony oxide such as antimony trioxide, other inorganic flame retardant aid, other organic flame retardant aid, a filler, a pigment, a lubricant, and/or a foaming agent, may also be added.

Examples of the triazine ring-containing compound include melamine, ammeline, benzoguanamine, acetoguanamine, phthalodiguanamine, melamine cyanurate, melamine pyrophosphate, butylene diguanamine, norbornene diguanamine, methylene diguanamine, ethylene dimelamine, trimethylene dimelamine, tetramethylene dimelamine, hexamethylene dimelamine, and 1,3-hexylene dimelamine.

Examples of the metal hydroxide include magnesium hydroxide, aluminum hydroxide, calcium hydroxide, barium hydroxide, zinc hydroxide and KISUMA® 5A (magnesium hydroxide, manufactured by Kyowa Chemical Industry Co., Ltd.).

Examples of the phosphate-based flame retardant include trimethyl phosphate, triethyl phosphate, tributyl phosphate, tributoxyethyl phosphate, trischloroethyl phosphate, trisdichloropropyl phosphate, triphenyl phosphate, tricresyl phosphate, cresyldiphenyl phosphate, trixylenyl phosphate, octyldiphenyl phosphate, xylenyldiphenyl phosphate, tris (isopropylphenyl) phosphate, 2-ethylhexyldiphenyl phosphate, t-butylphenyldiphenyl phosphate, bis(t-butylphenyl) phenyl phosphate, tris(t-butylphenyl)phosphate, isopropylphenyldiphenyl phosphate, bis(isopropylphenyl) diphenyl phosphate, and tris(isopropylphenyl)phosphate.

Examples of the condensed phosphoric acid ester-based flame retardant include 1,3-phenylene-bis(diphenylphosphate), 1,3-phenylene-bis(dixylenylphosphate), and bisphenol A-bis(diphenylphosphate).

Examples of the (poly)phosphate-based flame retardant include ammonium salts and amine salts of (poly)phosphoric acid, such as ammonium polyphosphate, melamine polyphosphate, piperazine polyphosphate, melamine pyrophosphate and piperazine pyrophosphate.

Examples of the above-described other inorganic flame retardant aid include inorganic compounds such as titanium oxide, aluminum oxide, magnesium oxide, hydrotalcites, talc and montmorillonite, and surface-treated products thereof. For example, a variety of commercially available products, such as TIPAQUE® R-680 (titanium oxide: manufactured by Ishihara Sangyo Kaisha, Ltd.), KYOWAMAG® 150 (magnesium oxide: manufactured by Kyowa Chemical Industry Co., Ltd.), DHT-4A® (hydrotalcite: manufactured by Kyowa Chemical Industry Co., Ltd.) and ALCAMIZER® 4 (zinc-modified hydrotalcite: manufactured by Kyowa Chemical Industry Co., Ltd.), can be used. Examples of the above-described other organic flame retardant aid include pentaerythritol.

In addition, in the resin composition of the present invention, as required, an additive(s) normally used in thermoplastic resins, for example, a cross-linking agent, an anti-fogging agent, an anti-plate-out agent, a surface treatment agent, a plasticizer, a lubricant, a flame retardant, a fluorescent agent, an antifungal agent, an antibacterial agent, a foaming agent, a metal inactivator, a mold-release agent, a pigment, a processing aid, an antioxidant and/or a light stabilizer, may also be incorporated in such a range that does not impair the effects of the present invention.

The method of producing the resin composition of the present invention is not particularly restricted, and any commonly used method can be employed as long as the polymer compound (E), the compound (F) represented by the Formula (2) and, as required, the alkali metal salt (G) and other arbitrary components are incorporated into a thermoplastic resin. For example, such components can be mixed and kneaded into the thermoplastic resin by roll kneading or bumper kneading, or using an extruder, a kneader or the like.

The polymer compound (E) may be directly added; however, as required, the polymer compound (E) may be impregnated into a carrier before the addition. In order to impregnate the polymer compound (E) into a carrier, the polymer compound (E) and the carrier can be directly heat-mixed or, as required, a method in which the polymer compound (E) is diluted with an organic solvent before being impregnated into the carrier and the solvent is subsequently removed can be employed. As the carrier, one which is known as a filler or bulking agent of a synthetic resin, or a flame retardant or light stabilizer that is solid at normal temperature can be employed, and examples of such a carrier include calcium silicate powder, silica powder, talc powder, alumina powder, titanium oxide powder, and these carriers with chemically modified surface, as well as the below-described flame retardants and antioxidants that are solid. Thereamong, those carriers with chemically modified surface are preferred, and silica powder having a chemically modified surface is more preferred. These carriers have an average particle size of preferably 0.1 to 100 µm, more preferably 0.5 to 50 µm.

As a method of incorporating the polymer compound (E) into a resin component, the polymer compound (E) may be synthesized while kneading the block polymer (C) and the epoxy compound (D) into the resin component and, in this process, the compound (F) and, as required, the alkali metal salt (G) may also be kneaded at the same time. Alternatively, the polymer compound (E) may be incorporated using a method of obtaining a molded article by mixing the polymer compound (E), the compound (F), the resin component and, as required, the alkali metal salt (G) at the time of molding such as injection molding, or a masterbatch of the thermoplastic resin, the compound (F) and, as required, the alkali metal salt (G), which has been produced in advance, may be incorporated.

The molded article of the present invention can be obtained by molding the thermoplastic resin composition of the present invention. Since the thermoplastic resin composition of the present invention has a high crystallization temperature, the molding cycle can be shortened.

The molding method is not particularly restricted, and examples thereof include extrusion processing, calender processing, injection molding, rolling, compression molding, blow molding and rotational molding, and molded articles of various shapes, such as resin plates, sheets, films, bottles, fibers and special shape articles, can be produced by these methods.

The molded article of the present invention exhibits excellent antistaticity and has a high crystallization temperature and is, therefore, highly strong and transparent. In addition, the molded article of the present invention not only exhibits excellent antistatic performance and persistence thereof but also has resistance to wiping.

The antistatic thermoplastic resin composition of the present invention and molded articles thereof can be used in a wide range of the same industrial fields as those exemplified above for the first embodiment.

EXAMPLES

Example 1

The present invention will now be described concretely by way of examples thereof.

Production Example 1-1

(Production of Polymer Compound (E)-1-1)

To a separable flask, 420 g of 1,4-cyclohexane dimethanol as a diol, 485 g of adipic acid as an aliphatic dicarboxylic acid, 0.5 g of isophthalic acid as an aromatic dicarboxylic acid, 0.5 g of an antioxidant (tetrakis[3-(3,5-di-tert-butyl-4-hydroxyphenyl)propionyloxymethyl]methane: ADK STAB AO-60, manufactured by ADEKA Corporation) and 0.5 g of zirconium acetate were added, and these materials were allowed to polymerize for 4 hours under normal pressure with the temperature being slowly increased from 160° C. to 200° C., and then for 3 hours at 200° C. under reduced pressure, whereby a polyester (A)-1-1 was obtained. This polyester (A)-1-1 had an acid value of 56 and a number-average molecular weight (Mn) of 3,200 in terms of polystyrene.

Next, 600 g of the thus obtained polyester (A)-1-1, 400 g of polyethylene glycol ((B)-1-1) having a number-average molecular weight of 2,000 as the above-described compound (B), 0.5 g of an antioxidant (ADK STAB AO-60) and 0.5 g of zirconium acetate were added and allowed to polymerize at 200° C. for 7 hours under reduced pressure, whereby a block polymer (C)-1-1 was obtained. This block polymer (C)-1-1 had an acid value of 11 and a number-average molecular weight (Mn) of 10,000 in terms of polystyrene.

To 300 g of the thus obtained block polymer (C)-1-1, 8.5 g of epoxidized soybean oil ((D)-1-1) was added as the above-described epoxy compound (D), and the resulting mixture was allowed to polymerize at 240° C. for 3 hours under reduced pressure, whereby a polymer compound (E)-1-1 was obtained.

Production Example 1-2

(Production of Polymer Compound (E)-1-2)

To a separable flask, 490 g of 1,4-cyclohexane dimethanol as a diol, 524 g of adipic acid as an aliphatic dicarboxylic acid, 0.5 g of phthalic anhydride as an aromatic dicarboxylic acid and 0.5 g of an antioxidant (ADK STAB AO-60) were added, and these materials were allowed to polymerize for 5 hours under normal pressure with the temperature being slowly increased from 160° C. to 210° C., and then for 3 hours at 210° C. under reduced pressure, whereby a polyester (A)-1-2 was obtained. This polyester (A)-1-2 had an acid value of 28 and a number-average molecular weight (Mn) of 5,400 in terms of polystyrene.

Next, 500 g of the thus obtained polyester (A)-1-2, 250 g of polyethylene glycol ((B)-1-2) having a number-average molecular weight of 4,000 as the above-described compound (B), 0.5 g of an antioxidant (ADK STAB AO-60) and 0.7 g of zirconium octylate were added and allowed to polymerize at 210° C. for 7 hours under reduced pressure, whereby a block polymer (C)-1-2 was obtained. This block polymer (C)-1-2 had an acid value of 9 and a number-average molecular weight (Mn) of 12,000 in terms of polystyrene.

To 360 g of the thus obtained block polymer (C)-1-2, 6 g of bisphenol F diglycidyl ether ((D)-1-1) was added as a polyepoxy compound (D), and the resulting mixture was allowed to polymerize at 240° C. for 3 hours under reduced pressure, whereby a polymer compound (E)-1-2 was obtained.

Production Example 1-3

(Production of Polymer Compound (E)-1-3)

To a separable flask, 591 g of ethylene oxide adduct of bisphenol A as a diol, 235 g (1.16 mol) of sebacic acid as an aliphatic dicarboxylic acid, 8 g (0.05 mol) of isophthalic acid as an aromatic dicarboxylic acid, 300 g of polyethylene glycol ((B)-1-1) having a number-average molecular weight of 2,000 as a compound (B) having at least one ethylene oxide group and hydroxyl groups at both ends and 0.8 g of an antioxidant (ADK STAB AO-60) were added, and these materials were allowed to polymerize for 5 hours under normal pressure with the temperature being slowly increased from 180° C. to 220° C. Then, 0.6 g of tetraisopropoxytitanate was further added, and the resulting mixture was allowed to polymerize at 220° C. for 7 hours under reduced pressure, whereby a block polymer (C)-1-3 was obtained. This block polymer (C)-1-3 had an acid value of 10 and a number-average molecular weight (Mn) of 10,100 in terms of polystyrene.

To 300 g of the thus obtained block polymer (C)-1-3, 6 g of dicyclopentadiene methanol diglycidyl ether (D)-1-3 as the epoxy compound (D) and 0.5 g of zirconium acetate were added, and the resulting mixture was allowed to polymerize at 240° C. for 5 hours under reduced pressure, whereby a polymer compound (E)-1-3 was obtained.

The effects of the present invention were verified using the polymer compounds (E)-1-1 to (E)-1-3 obtained by the above-described production methods. Evaluations were carried out by the following methods.

<Test Piece Preparation Conditions>

Resin compositions, which were obtained by blending a homopolypropylene having an MFR of 8 g/10 min at 230° C. with 0.05 parts by mass of a phenolic antioxidant (trade name "ADK STAB AO-60", manufactured by ADEKA Corporation), 0.05 parts by mass of a phosphorus-based antioxidant (trade name "ADK STAB 2112", manufactured by ADEKA Corporation), 0.05 parts by mass of calcium stearate and the components according to the respective formulations shown in Tables 1 and 2 below, were each granulated using a biaxial extruder manufactured by Ikegai Corp. (trade name: PCM30, equipped with a 60-mesh screen) under the conditions of 230° C. and 9 kg/hour, whereby pellets were obtained.

Then, using a horizontal injection molding machine manufactured by Nissei Plastic Industrial Co., Ltd. (product name: NEX80), the thus obtained pellets were each molded at a resin temperature of 230° C. and a die temperature of 40° C. to prepare test pieces for the measurement of surface specific resistance (100 mm×100 mm×3 mm).

<Method for Measuring Surface Specific Resistance (SR Value)>

The thus obtained test pieces for the measurement of surface specific resistance (100 mm×100 mm×3 mm) were each molded and, immediately thereafter, stored under the conditions of a temperature of 25° C. and a humidity of 60% RH for 1 day. Then, under the same atmosphere, the surface specific resistance ($\Omega/\square$) of each molded test piece was measured using an R8340 resistance meter manufactured by Advantest Corporation at an applied voltage of 500 V for a voltage application time of 1 minute. The measurement was performed at five spots, and an average thereof was determined. The results thereof are shown in Tables 1 and 2.

an increase in the amount of the aromatic metal phosphates (H) represented by the Formula (3) or (4) further improves the antistaticity.

Example 2

The present invention will now be further described concretely by way of examples thereof. It is noted here that, in the below-described Examples and the like, "%" and "ppm" are all based on mass unless otherwise specified.

The polymer compounds (E) used in the present invention were produced in accordance with the below-described Production Examples. In the below-described Production

TABLE 1

|  |  | Example 1-1 | Example 1-2 | Example 1-3 | Example 1-4 | Example 1-5 | Example 1-6 |
|---|---|---|---|---|---|---|---|
| Polypropylene |  | 90 | 95 | 90 | 80 | 90 | 90 |
| Polymer compound (E) | (E)-1-1 | 10 |  |  |  |  |  |
|  | (E)-1-2 |  | 5 | 10 | 20 |  |  |
|  | (E)-1-3 |  |  |  |  | 10 | 10 |
| Aromatic metal phosphate (H) | (H)-1-1 | 0.1 | 0.1 | 0.1 | 0.1 | 0.05 | 0.1 |
|  | (H)-1-2 | 0.1 | 0.15 | 0.15 | 0.15 |  |  |
|  | (H)-1-3 |  |  |  |  | 0.05 | 0.05 |
| Fatty acid metal salt (I) | (I)-1-1 | 0.05 |  |  |  |  |  |
|  | (I)-1-2 |  | 0.05 | 0.05 | 0.05 | 0.05 | 0.05 |
| Alkali metal salt (G) | (G)-1-1 | 0.5 | 0.5 | 0.5 | 0.5 |  |  |
|  | (G)-1-2 |  |  |  |  | 0.5 | 0.5 |
| Surface specific resistance ($\Omega/\square$) |  | $5 \times 10^{10}$ | $1 \times 10^{12}$ | $9 \times 10^{9}$ | $3 \times 10^{9}$ | $4 \times 10^{10}$ | $1 \times 10^{10}$ |

(H)-1-1: sodium-2,2'-methylene-bis(4,6-di-tert-butylphenyl)phosphate
(H)-1-2: lithium-2,2'-methylene-bis(4,6-di-tert-butylphenyl)phosphate
(H)-1-3: aluminum hydroxy-bis[2,2'-methylene-bis(4,6-di-tert-butylphenyl)phosphate]
(I)-1-1: lithium myristate
(I)-1-2: lithium stearate
(G)-1-1: sodium dodecylbenzenesulfonate
(G)-1-2: lithium p-toluenesulfonate

TABLE 2

|  |  | Comparative Example 1-1 | Comparative Example 1-2 | Comparative Example 1-3 | Comparative Example 1-4 | Comparative Example 1-5 |
|---|---|---|---|---|---|---|
| Polypropylene |  | 100 | 95 | 95 | 95 | 95 |
| Polymer compound (E) | (E)-1-1 |  |  |  |  |  |
|  | (E)-1-2 |  | 5 | 5 | 5 | 5 |
|  | (E)-1-3 |  |  |  |  |  |
| Aromatic metal phosphate (H) | (H)-1-1 |  |  | 0.3 |  |  |
|  | (H)-1-2 |  |  |  | 0.3 | 0.2 |
|  | (H)-1-3 |  |  |  |  |  |
| Fatty acid metal salt (I) | (I)-1-1 |  |  |  |  | 0.1 |
|  | (I)-1-2 |  |  |  |  |  |
| Alkali metal salt (G) | (G)-1-1 |  | 0.5 | 0.5 | 0.5 | 0.5 |
| Surface specific resistance ($\Omega/\square$) |  | $2 \times 10^{16}$ | $8 \times 10^{12}$ | $8 \times 10^{12}$ | $8 \times 10^{12}$ | $8 \times 10^{12}$ |

From Comparative Examples 1-3 to 1-5, no effect on the antistaticity was confirmed PGP when only one aromatic metal phosphate represented by the Formula (3) was incorporated; however, according to Example 1-2, the use of two aromatic metal phosphates represented by the Formula (3) resulted in an improvement in the antistatic performance. In addition, from Examples 1-5 and 1-6, it was confirmed that Examples, the number-average molecular weight was determined by the following method of measuring the molecular weight.

<Method for Measuring Molecular Weight>

The number-average molecular weight (hereinafter, referred to as "Mn") was measured by gel permeation chromatography (GPC). The conditions of the Mn measurement were as follows.

Apparatus: GPC apparatus, manufactured by JASCO Corporation
Solvent: tetrahydrofuran
Standard substance: polystyrene
Detector: differential refractometer (RI detector)
Column stationary phase: SHODEX® KF-804L, manufactured by Showa Denko K.K.
Column temperature: 40° C.
Sample concentration: 1 mg/1 mL
Flow rate: 0.8 mL/min
Injection volume: 100 μL Production Example 2-1

To a separable flask, 656 g of 1,4-cyclohexane dimethanol, 708 g (4.85 mol) of adipic acid, 0.7 g (0.01 mol) of phthalic anhydride and 0.7 g of an antioxidant (tetrakis[3-(3,5-di-tert-butyl-4-hydroxyphenyl)propionyloxymethyl] methane: ADK STAB AO-60, manufactured by ADEKA Corporation) were added, and these materials were allowed to polymerize for 5 hours under normal pressure with the temperature being slowly increased from 160° C. to 210° C., and then for 3 hours at 210° C. under reduced pressure, whereby a polyester (A)-2-1 was obtained. This polyester (A)-2-1 had an acid value of 28 and a number-average molecular weight (Mn) of 5,400 in terms of polystyrene.

Next, 600 g of the thus obtained polyester (A)-2-1, 300 g of polyethylene glycol having a number-average molecular weight of 4,000 as a compound (B)-2-1 having hydroxyl groups at both ends, 0.5 g of an antioxidant (ADK STAB AO-60) and 0.8 g of zirconium octylate were added and allowed to polymerize at 210° C. for 7 hours under reduced pressure, whereby a block polymer (C)-2-1 having a structure comprising carboxyl groups at both ends was obtained. This block polymer (C)-2-1 having a structure comprising carboxyl groups at both ends had an acid value of 9 and a number-average molecular weight (Mn) of 12,000 in terms of polystyrene.

To 360 g of the thus obtained block polymer (C)-2-1 having a structure comprising carboxyl groups at both ends, 6 g of bisphenol F diglycidyl ether was added as an epoxy compound (D)-2-1, and the resulting mixture was allowed to polymerize at 240° C. for 3 hours under reduced pressure, whereby a polymer compound (E)-2-1 used in the present invention was obtained.

Production Example 2-2

To a separable flask, 370 g of 1,4-bis(β-hydroxyethoxy) benzene, 289 g (1.98 mol) of adipic acid, 8 g (0.05 mol) of isophthalic acid and 0.5 g of an antioxidant (ADK STAB AO-60) were added, and these materials were allowed to polymerize for 5 hours under normal pressure with the temperature being slowly increased from 180° C. to 220° C. Then, 0.5 g of tetraisopropoxytitanate was further added, and the resulting mixture was allowed to polymerize at 220° C. under reduced pressure for 5 hours, whereby a polyester (A)-2-2 was obtained. This polyester (A)-2-2 had an acid value of 56 and a number-average molecular weight (Mn) of 4,900 in terms of polystyrene.

Next, to 300 g of the thus obtained polyester (A)-2-2, 150 g of polyethylene glycol having a number-average molecular weight of 4,000 as a compound (B)-2-1 having hydroxyl groups at both ends, 0.5 g of an antioxidant (ADK STAB AO-60) and 0.5 g of zirconium acetate were added and allowed to polymerize at 220° C. for 7 hours under reduced pressure, whereby a block polymer (C)-2-2 having a structure comprising carboxyl groups at both ends was obtained. This block polymer (C)-2-2 having a structure comprising carboxyl groups at both ends had an acid value of 11 and a number-average molecular weight (Mn) of 12,300 in terms of polystyrene.

To 300 g of the thus obtained block polymer (C)-2-2, 11 g of dicyclopentadiene methanol diglycidyl ether was added as an epoxy compound (D)-2-2, and the resulting mixture was allowed to polymerize at 240° C. for 4 hours under reduced pressure, whereby a polymer compound (E)-2-2 used in the present invention was obtained.

Production Example 2-3

To a separable flask, 591 g of ethylene oxide adduct of bisphenol A, 235 g (1.16 mol) of sebacic acid, 8 g (0.05 mol) of isophthalic acid, 300 g of polyethylene glycol having a number-average molecular weight of 2,000 as a compound (B)-2-2 having hydroxyl groups at both ends and 0.8 g of an antioxidant (ADK STAB AO-60) were added, and these materials were allowed to polymerize for 5 hours under normal pressure with the temperature being slowly increased from 180° C. to 220° C. Then, 0.6 g of tetraisopropoxytitanate was further added, and the resulting mixture was allowed to polymerize at 220° C. for 7 hours under reduced pressure, whereby a block polymer (C)-2-3 having a structure comprising carboxyl groups at both ends was obtained. This block polymer (C)-2-3 having a structure comprising carboxyl groups at both ends had an acid value of 10 and a number-average molecular weight (Mn) of 10,100 in terms of polystyrene.

To 300 g of the thus obtained block polymer (C)-2-3 having a structure comprising carboxyl groups at both ends, 7 g of epoxidized soybean oil as an epoxy compound (D)-2-3 and 0.5 g of zirconium acetate were added, and the resulting mixture was allowed to polymerize at 240° C. for 5 hours under reduced pressure, whereby a polymer compound (E)-2-3 used in the present invention was obtained.

Examples 2-1 to 2-13 and Comparative Examples 2-1 to 2-12

Using resin compositions that were blended based on the respective formulations (parts by mass) shown in Tables 3 to 6 below, test pieces were obtained in accordance with the below-described test piece preparation conditions. The thus obtained test pieces were each subjected to the measurement of surface specific resistance (SR value) and the test for resistance to wiping with water as described below.

Further, pellets obtained in the test piece preparation were each subjected to the measurement of crystallization temperature as described below.

As the compound (F), compound Nos. 2, 7 and 15 having the following respective structures were used.

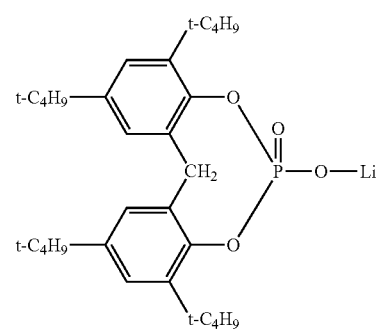

Compound No. 2

-continued

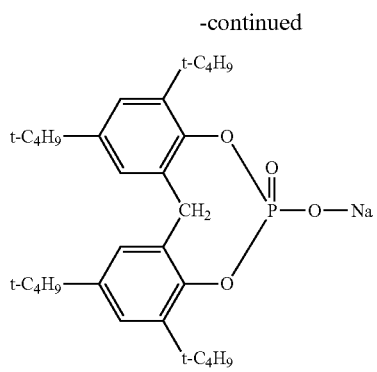

Compound No. 7

Compound No. 15

<Test Piece Preparation Conditions>

Resin compositions, which were obtained by blending 0.05 parts by mass of a phenolic antioxidant (trade name "ADK STAB AO-60", manufactured by ADEKA Corporation), 0.05 parts by mass of a phosphorus-based antioxidant (trade name "ADK STAB 2112", manufactured by ADEKA Corporation), 0.05 parts by mass of calcium stearate and the components according to the respective formulations shown in Tables 3 to 6 below, were each granulated using a biaxial extruder manufactured by Ikegai Corp. (PCM30, equipped with a 60-mesh screen) under the conditions of 230° C. and 9 kg/hour, whereby pellets were obtained. Then, using a horizontal injection molding machine (NEX80, manufactured by Nissei Plastic Industrial Co., Ltd.), the thus obtained pellets were each molded at a resin temperature of 230° C. and a die temperature of 40° C. to prepare test pieces for the measurement of surface specific resistance (100 mm×100 mm×3 mm) and test pieces for the measurement of bending modulus of elasticity, Charpy impact strength and thermal deformation temperature (80 mm×10 mm×4 mm).

<Method for Measuring Surface Specific Resistance (SR Value)>

The thus obtained test pieces for the measurement of surface specific resistance (100 mm×100 mm×3 mm) were each molded and, immediately thereafter, stored under the conditions of a temperature of 25° C. and a humidity of 60% RH. After 1 day and 30 days of storage, under the same atmosphere, the surface specific resistance ($\Omega/\square$) of each molded test piece was measured using an R8340 resistance meter manufactured by Advantest Corporation at an applied voltage of 500 V and a voltage application time of 1 minute. The measurement was performed at five spots, and an average thereof was determined.

<Test for Resistance to Wiping with Water>

The surface of each of the thus obtained test pieces was wiped with a waste cloth 50 times in running water and subsequently left to stand for 24 hours in an incubator adjusted to have a temperature of 25° C. and a humidity of 60%. Thereafter, the surface specific resistance ($\Omega/\square$) was measured using an R8340 resistance meter manufactured by Advantest Corporation at an applied voltage of 500 V and a voltage application time of 1 minute. The measurement was performed at five spots, and an average thereof was determined.

<Method for Measuring Crystallization Temperature>

Using a differential scanning calorimeter (DIAMOND, manufactured by PerkinElmer Co., Ltd.), the pellets obtained above were each heated to 230° C. at a rate of 10° C./min and, after maintaining each pellet at this temperature for 5 minutes, the pellet was cooled to 50° C. at a rate of −10° C./min to obtain a chart, in which the endothermic peak was determined as the crystallization temperature.

<Bending Modulus of Elasticity>

The bending modulus of elasticity was measured in accordance with ISO178.

<Charpy Impact Strength>

The Charpy impact strength was measured in accordance with ISO179-1 (with notch).

<Thermal Deformation Temperature>

The thermal deformation temperature was measured in accordance with ISO75-2.

TABLE 3

| | | Example | | | | | | |
|---|---|---|---|---|---|---|---|---|
| | | 2-1 | 2-2 | 2-3 | 2-4 | 2-5 | 2-6 | 2-7 |
| Polypropylene A*1 | | 100 | 100 | 100 | 100 | 100 | 100 | 100 |
| Polymer compound (E) | (E)-2-1 | 5 | 10 | 15 | 20 | 10 | 10 | 10 |
| | (E)-2-2 | | | | | | | |
| | (E)-2-3 | | | | | | | |
| Compound (F) | Compound No. 2 | 0.2 | 0.2 | 0.2 | 0.2 | 0.2 | | |
| | Compound No. 7 | | | | | | 0.2 | |
| | Compound No. 15 | | | | | | | 0.2 |
| Alkali metal salt (G) | NaDBS*2 | 0.5 | 0.5 | 0.5 | 0.5 | | 0.5 | 0.5 |
| | LiOTs*3 | | | | | | | |
| | LiS*4 | | | | | | | |
| Surface specific resistance ($\Omega/\square$) | After 1 day | $4 \times 10^{12}$ | $1 \times 10^{11}$ | $3 \times 10^{10}$ | $6 \times 10^{9}$ | $1 \times 10^{12}$ | $1 \times 10^{11}$ | $1 \times 10^{11}$ |
| | After 30 days | $4 \times 10^{12}$ | $1 \times 10^{11}$ | $4 \times 10^{10}$ | $6 \times 10^{9}$ | $1 \times 10^{12}$ | $1 \times 10^{11}$ | $1 \times 10^{11}$ |
| | Resistance to wiping with water | $4 \times 10^{12}$ | $1 \times 10^{11}$ | $4 \times 10^{10}$ | $6 \times 10^{9}$ | $1 \times 10^{12}$ | $1 \times 10^{11}$ | $1 \times 10^{11}$ |

TABLE 3-continued

| | Example | | | | | | |
|---|---|---|---|---|---|---|---|
| | 2-1 | 2-2 | 2-3 | 2-4 | 2-5 | 2-6 | 2-7 |
| Bending modulus of elasticity (MPa) | 1,820 | 1,820 | 1,800 | 1,800 | 1,820 | 1,850 | 1,740 |
| Charpy impact strength (J/m$^2$) | 1 | 1 | 1 | 1 | 1 | 1 | 1 |
| Thermal deformation temperature (° C.) | 103 | 103 | 102 | 101 | 103 | 106 | 100 |
| Crystallization temperature (° C.) | 124 | 124 | 123 | 121 | 124 | 125 | 121 |

*[1]homopolypropylene having a melt flow rate (ISO1133, 230° C. × 2.16 kg) of 8 g/10 min
*[2]sodium dodecylbenzenesulfonate
*[3]lithium p-toluenesulfonate
*[4]lithium stearate

TABLE 4

| | | Example | | | | | |
|---|---|---|---|---|---|---|---|
| | | 2-8 | 2-9 | 2-10 | 2-11 | 2-12 | 2-13 |
| | Polypropylene A*[1] | 100 | 100 | 100 | 100 | 100 | |
| | Polypropylene B*[5] | | | | | | 100 |
| Polymer compound (E) | (E)-2-1 | | | | | | 10 |
| | (E)-2-2 | 10 | 10 | 10 | | | |
| | (E)-2-3 | | | | 10 | 10 | |
| Compound (F) | Compound No. 2 | 0.2 | | | | | 0.2 |
| | Compound No. 7 | | 0.05 | 0.3 | | | |
| | Compound No. 15 | | | | 0.2 | 0.2 | |
| Alkali metal salt (G) | NaDBS*[2] | | | | | | 0.5 |
| | LiOTs*[3] | 0.5 | 0.5 | 0.5 | | | |
| | LiS*[4] | | | | 0.5 | 1.0 | |
| Surface specific resistance (Ω/□) | After 1 day | $8 \times 10^{10}$ | $8 \times 10^{10}$ | $8 \times 10^{10}$ | $6 \times 10^{10}$ | $5 \times 10^{9}$ | $1 \times 10^{11}$ |
| | After 30 days | $8 \times 10^{10}$ | $8 \times 10^{10}$ | $8 \times 10^{10}$ | $6 \times 10^{10}$ | $5 \times 10^{9}$ | $1 \times 10^{11}$ |
| | Resistance to wiping with water | $8 \times 10^{10}$ | $8 \times 10^{10}$ | $8 \times 10^{10}$ | $6 \times 10^{10}$ | $5 \times 10^{9}$ | $1 \times 10^{11}$ |
| Bending modulus of elasticity (MPa) | | 1,820 | 1,640 | 1,870 | 1,730 | 1,730 | 1,620 |
| Charpy impact strength (J/m$^2$) | | 1 | 1 | 1 | 1 | 1 | 7 |
| Thermal deformation temperature (° C.) | | 103 | 96 | 106 | 103 | 103 | 94 |
| Crystallization temperature (° C.) | | 123 | 117 | 128 | 123 | 123 | 122 |

*[5]impact copolymer polypropylene, manufactured by Japan Polypropylene Corporation: trade name "BC03B" (melt flow rate = 30 g/10 min)

TABLE 5

| | | Comparative Example | | | | | | |
|---|---|---|---|---|---|---|---|---|
| | | 2-1 | 2-2 | 2-3 | 2-4 | 2-5 | 2-6 | 2-7 |
| | Polypropylene A*[1] | 100 | 100 | 100 | 100 | 100 | 100 | 100 |
| Polymer compound (E) | (E)-2-1 | | | 10 | 10 | | | |
| | (E)-2-2 | | | | | | | |
| | (E)-2-3 | | | | | | | |
| Compound (F) | Compound No. 2 | | | | | 0.2 | 0.2 | |
| | Compound No. 7 | | | | | | | 0.2 |
| | Compound No. 15 | | | | | | | |
| Alkali metal salt (G) | NaDBS*[2] | | 0.5 | | 0.5 | | | |
| | LiOTs*[3] | | | | | | 0.5 | |
| | LiS*[4] | | | | | | | |
| Surface specific resistance (Ω/□) | After 1 day | $2 \times 10^{16}$ | $2 \times 10^{16}$ | $1 \times 10^{12}$ | $1 \times 10^{11}$ | $2 \times 10^{16}$ | $2 \times 10^{16}$ | $2 \times 10^{16}$ |
| | After 30 days | $2 \times 10^{16}$ | $2 \times 10^{16}$ | $1 \times 10^{12}$ | $1 \times 10^{11}$ | $2 \times 10^{16}$ | $2 \times 10^{16}$ | $2 \times 10^{16}$ |
| | Resistance to wiping with water | $2 \times 10^{16}$ | $2 \times 10^{16}$ | $1 \times 10^{12}$ | $1 \times 10^{11}$ | $2 \times 10^{16}$ | $2 \times 10^{16}$ | $3 \times 10^{16}$ |

TABLE 5-continued

|  | Comparative Example | | | | | | |
|---|---|---|---|---|---|---|---|
|  | 2-1 | 2-2 | 2-3 | 2-4 | 2-5 | 2-6 | 2-7 |
| Bending modulus of elasticity (MPa) | 1,460 | 1,460 | 1,460 | 1,440 | 1,820 | 1,820 | 1,850 |
| Charpy impact strength (J/m$^2$) | 1 | 1 | 1 | 1 | 1 | 1 | 1 |
| Thermal deformation temperature (° C.) | 90 | 90 | 90 | 89 | 103 | 103 | 106 |
| Crystallization temperature (° C.) | 114 | 114 | 114 | 112 | 124 | 124 | 125 |

TABLE 6

|  |  | Comparative Example | | | | |
|---|---|---|---|---|---|---|
|  |  | 2-8 | 2-9 | 2-10 | 2-11 | 2-12 |
|  | Polypropylene B*$^5$ | 100 | 100 | 100 | 100 | 100 |
| Polymer compound (E) | (E)-2-1 |  |  |  | 10 | 10 |
|  | (E)-2-2 |  |  |  |  |  |
|  | (E)-2-3 |  |  |  |  |  |
| Compound (F) | Compound No. 2 |  |  |  |  | 0.2 |
|  | Compound No. 7 |  |  |  |  |  |
|  | Compound No. 15 |  |  |  |  |  |
| Alkali metal salt (G) | NaDBS*$^2$ |  | 0.5 |  | 0.5 |  |
|  | LiOTs*$^3$ |  |  |  |  |  |
|  | LiS*$^4$ |  |  |  |  |  |
| Surface specific resistance (Ω/□) | After 1 day | 3 × 10$^{16}$ | 3 × 10$^{16}$ | 2 × 10$^{12}$ | 1 × 10$^{11}$ | 2 × 10$^{16}$ |
|  | After 30 days | 3 × 10$^{16}$ | 3 × 10$^{16}$ | 2 × 10$^{12}$ | 1 × 10$^{11}$ | 2 × 10$^{16}$ |
|  | Resistance to wiping with water | 3 × 10$^{16}$ | 3 × 10$^{16}$ | 2 × 10$^{12}$ | 1 × 10$^{11}$ | 2 × 10$^{16}$ |
| Bending modulus of elasticity (MPa) | | 1,300 | 1,300 | 1,290 | 1,290 | 1,620 |
| Charpy impact strength (J/m$^2$) | | 7 | 7 | 7 | 7 | 7 |
| Thermal deformation temperature (° C.) | | 80 | 80 | 80 | 79 | 94 |
| Crystallization temperature (° C.) | | 113 | 113 | 113 | 112 | 122 |

From the results shown in Tables above, it is seen that the resin compositions of Examples according to the present invention sustain antistatic performance over a long period of time and has excellent crystallinity and water resistance. In addition, the molded articles obtained therefrom were confirmed to have a high bending modulus of elasticity and a high thermal deformation temperature and to exhibit excellent strength.

The invention claimed is:

1. A resin additive composition comprising two or more selected from aromatic metal phosphates (H) represented by the following Formula (3) or (4) in an amount of 0.001 to 50 parts by mass with respect to 100 parts by mass of a polymer compound (E), wherein said polymer compound (E) has a structure in which a diol, an aliphatic dicarboxylic acid, an aromatic dicarboxylic acid, a compound (B) which comprises at least one group represented by the following Formula (1) and has hydroxyl groups at both ends, and an epoxy compound (D) having two or more epoxy groups are bound via ester bonds:

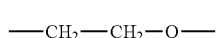 (1)

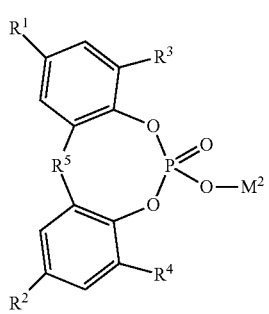 (3)

wherein R$^1$ to R$^4$ each independently represent a hydrogen atom or a linear or branched alkyl group having 1 to 9 carbon atoms; R$^5$ represents an alkylidene group having 1 to 4 carbon atoms; and M$^2$ represents an alkali metal,

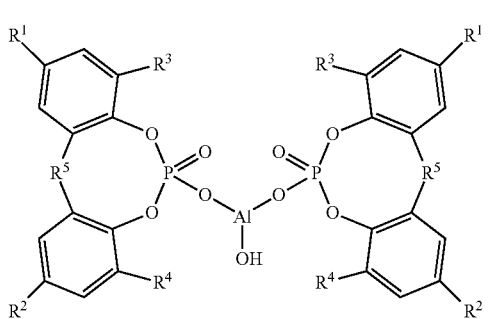

(4)

wherein $R^1$ to $R^4$ each independently represent a hydrogen atom or a linear or branched alkyl group having 1 to 9 carbon atoms; and $R^5$ represents an alkylidene group having 1 to 4 carbon atoms, wherein said aromatic metal phosphates (H) are a mixture of a sodium salt compound represented by said Formula (3) wherein $M^2$ is sodium and a lithium salt compound represented by said Formula (3) wherein $M^2$ is lithium, and wherein the mass ratio of said sodium salt compound and said lithium salt compound (sodium salt compound/ lithium salt compound) is in a range of 1/4 to 4/1.

2. The resin additive composition according to claim 1, further comprising 10 to 50 parts by mass of a fatty acid metal salt (I) represented by the following Formula (5) with respect to a total of 100 parts by mass of two or more selected from said aromatic metal phosphates (H):

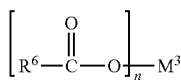

(5)

(wherein, $R^6$ represents an unsubstituted or hydroxy group-substituted aliphatic group having 1 to 40 carbon atoms; $M^3$ represents a metal atom; n is an integer of 1 to 4 and represents the valence of said metal atom $M^3$).

3. The resin additive composition according to claim 1, wherein said polymer compound (E) has a structure in which a polyester (A), which is constituted by a diol, an aliphatic dicarboxylic acid and an aromatic dicarboxylic acid, said compound (B) and said epoxy compound (D) are bound via ester bonds.

4. The resin additive composition according to claim 3, wherein said polymer compound (E) has a structure in which a block polymer (C) having carboxyl groups at both ends and said epoxy compound (D) are bound via an ester bond, said block polymer (C) comprising a block constituted by said polyester (A) and a block constituted by said compound (B) that are repeatedly and alternately bound via ester bonds.

5. The resin additive composition according to claim 3, wherein said polyester (A) has a structure comprising carboxyl groups at both ends.

6. The resin additive composition according to claim 4, wherein said block constituted by said polyester (A) has a number-average molecular weight of 800 to 8,000 in terms of polystyrene, said block constituted by said compound (B) has a number-average molecular weight of 400 to 6,000 in terms of polystyrene, and said block polymer (C) has a number-average molecular weight of 5,000 to 25,000 in terms of polystyrene.

7. The resin additive composition according to claim 1, wherein said compound (B) is a polyethylene glycol.

8. An antistatic thermoplastic resin composition comprising, with respect to 100 parts by mass of a thermoplastic resin:
3 to 60 parts by mass of at least one polymer compound (E); and
0.001 to 10 parts by mass of at least one compound (F) represented by the following Formula (2),
wherein said polymer compound (E) has a structure in which a diol, an aliphatic dicarboxylic acid, an aromatic dicarboxylic acid, a compound (B) which comprises at least one group represented by the following Formula (1) and has hydroxyl groups at both ends, and an epoxy compound (D) having two or more epoxy groups are bound via ester bonds:

(1)

(2)

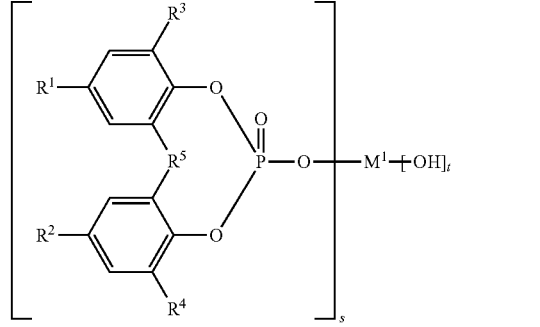

wherein $R^1$ to $R^4$ each independently represent a hydrogen atom or an alkyl group having 1 to 9 carbon atoms; $R^5$ represents an alkylidene group having 1 to 4 carbon atoms; $M^1$ represents an alkali metal atom, an alkaline earth metal atom, a beryllium atom, a magnesium atom or an aluminum atom; when $M^1$ is an alkali metal atom, s is 1 and t is 0; when $M^1$ is an alkaline earth metal atom, a beryllium atom or a magnesium atom, s is 2 and t is 0; and when $M^1$ is an aluminum atom, s is 1 or 2 and t is (3−s), wherein said compound (F) is an aromatic metal phosphate (H) represented by the following Formula (3) or (4), wherein said antistatic thermoplastic resin composition comprises 0.001 to 50 parts by mass of two or more selected from said aromatic metal phosphates (H) with respect to 100 parts by mass of said polymer compound (E):

(3)

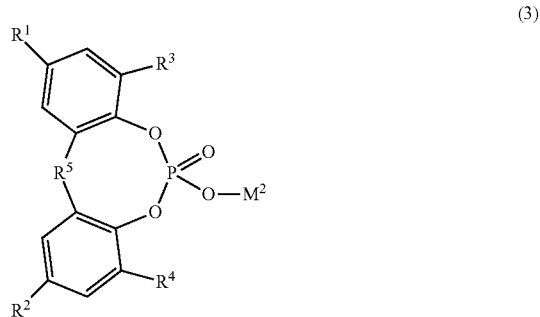

wherein R¹ to R⁴ each independently represent the same as in said Formula (2); R⁵ represents the same as in said Formula (2); and M² represents an alkali metal,

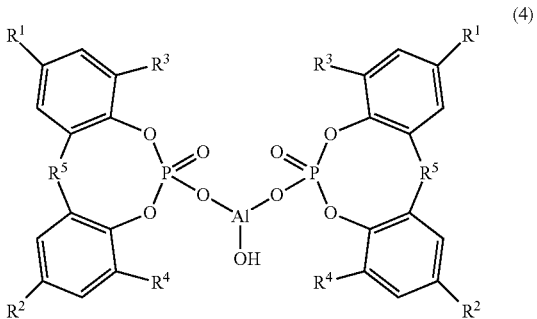

wherein R¹ to R⁵ represent the same as in said Formula (3), wherein said aromatic metal phosphates (H) are a mixture of a sodium salt compound represented by said Formula (3) wherein M² is sodium and a lithium salt compound represented by said Formula (3) wherein M² is lithium, and wherein the mass ratio of said sodium salt compound and said lithium salt compound (sodium salt compound/lithium salt compound) is in a range of 1/4 to 4/1.

9. The antistatic thermoplastic resin composition according to claim 8, further comprising 10 to 50 parts by mass of a fatty acid metal salt (I) represented by the following Formula (5) with respect to a total of 100 parts by mass of two or more selected from said aromatic metal phosphates (H):

wherein R⁶ represents an unsubstituted or hydroxy group-substituted aliphatic group having 1 to 40 carbon atoms; M³ represents a metal atom; n is an integer of 1 to 4 and represents the valence of said metal atom M³.

10. The antistatic thermoplastic resin composition according to claim 8, wherein said polymer compound (E) has a structure in which a polyester (A), which is constituted by a diol, an aliphatic dicarboxylic acid and an aromatic dicarboxylic acid, said compound (B) and said epoxy compound (D) are bound via ester bonds.

11. The antistatic thermoplastic resin composition according to claim 10, wherein said polymer compound (E) has a structure in which a block polymer (C) having carboxyl groups at both ends and said epoxy compound (D) are bound via an ester bond, said block polymer (C) comprising a block constituted by said polyester (A) and a block constituted by said compound (B) that are repeatedly and alternately bound via ester bonds.

12. The antistatic thermoplastic resin composition according to claim 10, wherein said polyester (A) constituting said polymer compound (E) has a structure comprising carboxyl groups at both ends.

13. The antistatic thermoplastic resin composition according to claim 11, wherein, in said polymer compound (E), said block constituted by said polyester (A) has a number-average molecular weight of 800 to 8,000 in terms of polystyrene, said block constituted by said compound (B) has a number-average molecular weight of 400 to 6,000 in terms of polystyrene, and said block polymer (C) has a number-average molecular weight of 5,000 to 25,000 in terms of polystyrene.

14. The antistatic thermoplastic resin composition according to claim 8, wherein said compound (B) constituting said polymer compound (E) is a polyethylene glycol.

15. The antistatic thermoplastic resin composition according to claim 8, further comprising 0.01 to 5 parts by mass of at least one alkali metal salt (G) with respect to 100 parts by mass of said thermoplastic resin.

16. The antistatic thermoplastic resin composition according to claim 11, further comprising 0.01 to 5 parts by mass of at least one alkali metal salt (G) with respect to 100 parts by mass of said thermoplastic resin.

17. The antistatic thermoplastic resin composition according to claim 8, wherein said thermoplastic resin is a polyolefin resin.

18. A molded article obtained by molding the antistatic thermoplastic resin composition according to claim 10.

19. A molded article obtained by molding the antistatic thermoplastic resin composition according to claim 11.

20. A molded article obtained by molding the antistatic thermoplastic resin composition according to claim 15.

* * * * *